US009695238B2

(12) United States Patent
Gao et al.

(10) Patent No.: US 9,695,238 B2
(45) Date of Patent: Jul. 4, 2017

(54) SCREENING METHOD FOR INHIBITORS OF BINDING OF ZBR7R1 TO CD155

(71) Applicant: ZYMOGENETICS, INC., Princeton, NJ (US)

(72) Inventors: Zeren Gao, Redmond, WA (US); Steven D. Levin, Seattle, WA (US); Janine M. Bilsborough, Simi Valley, CA (US); James W. West, San Mateo, CA (US); Cameron S. Brandt, Seattle, WA (US); Eric M. Chadwick, Bellevue, WA (US)

( * ) Notice: Subject to any disclaimer, the term of this patent is extended or adjusted under 35 U.S.C. 154(b) by 0 days.

(21) Appl. No.: 15/069,065

(22) Filed: Mar. 14, 2016

(65) Prior Publication Data

US 2016/0185863 A1 Jun. 30, 2016

Related U.S. Application Data

(60) Continuation of application No. 14/300,724, filed on Jun. 10, 2014, now abandoned, which is a division of application No. 13/417,587, filed on Mar. 12, 2012, now abandoned, which is a continuation of application No. 12/828,575, filed on Jul. 1, 2010, now abandoned, which is a division of application No. 12/270,775, filed on Nov. 13, 2008, now abandoned, which is a division of application No. 11/433,276, filed on May 12, 2006, now abandoned.

(60) Provisional application No. 60/795,005, filed on Apr. 26, 2006, provisional application No. 60/791,626, filed on Apr. 13, 2006, provisional application No. 60/680,374, filed on May 12, 2005.

(51) Int. Cl.

| | |
|---|---|
| *C07K 16/28* | (2006.01) |
| *C07K 14/47* | (2006.01) |
| *C07K 14/705* | (2006.01) |
| *G01N 33/50* | (2006.01) |
| *C12Q 1/66* | (2006.01) |
| *G01N 33/569* | (2006.01) |
| *A61K 38/00* | (2006.01) |
| *A61K 39/00* | (2006.01) |

(52) U.S. Cl.

CPC .......... *C07K 16/2827* (2013.01); *C07K 14/47* (2013.01); *C07K 14/70532* (2013.01); *C07K 16/2803* (2013.01); *C07K 16/2818* (2013.01); *C12Q 1/66* (2013.01); *G01N 33/505* (2013.01); *G01N 33/56972* (2013.01); *A61K 38/00* (2013.01); *A61K 2039/507* (2013.01); *C07K 2317/34* (2013.01); *C07K 2317/73* (2013.01); *C07K 2317/75* (2013.01); *C07K 2317/76* (2013.01); *C07K 2319/00* (2013.01); *C07K 2319/30* (2013.01); *G01N 2333/70532* (2013.01)

(58) Field of Classification Search
None
See application file for complete search history.

(56) References Cited

U.S. PATENT DOCUMENTS

| | | | |
|---|---|---|---|
| 5,869,337 | A | 2/1999 | Crabtree et al. |
| 6,518,033 | B1 | 2/2003 | Gromeier et al. |
| 7,193,069 | B2 | 3/2007 | Isogai et al. |
| 2004/0121370 | A1 | 6/2004 | Baldwin et al. |
| 2004/0219131 | A1 | 11/2004 | Patten et al. |

FOREIGN PATENT DOCUMENTS

| | | |
|---|---|---|
| WO | 00/58334 | 10/2000 |
| WO | 01/74853 | 10/2001 |
| WO | 01/94413 | 12/2001 |
| WO | 03/054152 | 7/2003 |
| WO | 03/068943 | 8/2003 |
| WO | 2004/024068 | 3/2004 |
| WO | 2004/024072 | 3/2004 |
| WO | WO 2004/050870 | 6/2004 |
| WO | 2006/124667 | 11/2006 |

OTHER PUBLICATIONS

Pende et al., *Mol. Immunol.* 42(4):463-9, 2005.
Castriconi et al., *Cancer Res.* 64(24):9180-4, 2004.
Bachelet et al., *J. Biol. Chem.* 281(37):27190-6, 2006.
Oda et al., *Biochem. Biophys. Res. Commun.* 319(4):1253-64, 2004.
Lehr-Mason et al., Database accession No. ADA21139, 2003.
Bodary et al., Database accession No. ADL91492, 2004.
Nobis et al., *J. of General Virology* 66(12):2563-2670, 1985.
Seth et al., Immunobiology 210(6-8):542, 2005 XP009074924.
Chambers et al., Ann. Rev. Immunol. 19:565-594, 2001.
Egen et al., Nature Immunol. 3:611-618, 2002.
Abbas et al., Nat. Med. 5:1345-6,1999.
Coyle et al., Nat. Immonol. 2:203-9, 2001.
Carreno et al., Anna. Rev. Immunol. 20:29-53, 2002.
Liang et al., Curr. Opin. Immunol. 14:384-90, 2002.
Swallow et al., Immunity 11: 423-32, 1999.
Yoshinaga et al., Nature 402: 827-32, 1999.
Ling, et al., J. Immunol. 164:1653-7, 2000.
Wang et al., Blood 96:2808-13, 2000.
Brodie et al., Curr. Biol. 10:333-6, 2000.
Freeman et al., J. Exp. Med. 192: 1027-34, 2000.
Dong et al., Nat. Med. 5:1365-9, 1999.
Latchman et al, Nat. Immunol. 2: 261-8, 2001.
Tseng et al., J. Exp. Med. 193:839-46, 2001.
Chapoval et al., Nat. Immunol. 2:269-74 2001.
Sun et al., J. Immunol. 168:6294-7, 2002.

(Continued)

*Primary Examiner* — Elly-Gerald Stoica
(74) *Attorney, Agent, or Firm* — Gregory R. Bellomy

(57) ABSTRACT

The present invention provides a newly identified B7 receptor, zB7R1 that functions as lymphocyte inhibitory receptor, which is a PD-1-like molecule and is expressed on T cells. The present invention also provides the discovery of zB7R1's ability to bind to CD155. Methods and compositions for modulating zB7R1-mediated negative signaling and interfering with the interaction of its counter-receptor for therapeutic, diagnostic and research purposes are also provided.

14 Claims, No Drawings

(56) References Cited

OTHER PUBLICATIONS

Dudley et al., Science 298:850-854, 2002.
Pardoll, Nature Biotech. 20:1207-1208, 2002.
Kuhnel et al., The VASP Tetramerization Domain Is a Right-Handed Coiled Coil Based on a 15-Residue Repeat, PNAS 101:17027-17032, 2004.
Zimermann et al., Relaxation, Equilibrium Oligomerization, and Molecular Symmetry of the VASP (336-380) EVH2 Tetramer, Biochemistry, 41: 11143-11151, 2002.
Baury, et al., "Identification of secreted CD155 isoforms", Biochem. Biophys. Res. Comm., vol. 309 (1), pp. 175-182 (2003).
Wahl, et al., "Interaction of B7RP-1 with ICOS Negatively Regulates Antigen Presentation by B Cells", Inflammation, vol. 27 (4), pp. 191-200 (2003).

SCREENING METHOD FOR INHIBITORS OF BINDING OF ZBR7R1 TO CD155

REFERENCE TO RELATED INVENTIONS

This application is a continuation of U.S. application Ser. No. 14/300,724, filed Jun. 10, 2014, pending, which is a divisional of U.S. application Ser. No. 13/417,587, filed Mar. 12, 2012, now abandoned, which is a continuation of U.S. application Ser. No. 12/828,575, filed Jul. 1, 2010, now abandoned, which is a divisional of U.S. application Ser. No. 12/270,775, filed Nov. 13, 2008, now abandoned, which is a divisional of U.S. application Ser. No. 11/433,276, filed May 12, 2006, now abandoned, which claims the benefit of U.S. Provisional Application Ser. No. 60/680,374, filed May 12, 2005, U.S. Provisional Application Ser. No. 60/791,626, filed Apr. 13, 2006, and U.S. Provisional Application Ser. No. 60/795,005, filed Apr. 26, 2006 all of which are incorporated in their entirety herein by reference.

SEQUENCE LISTING

The Sequence Listing filed electronically herewith is also hereby incorporated by reference in its entirety (File Name: 20160314_SEQT_Z00512USCNT2.txt; Date Created: 10 Mar. 2016; File Size: 89.5 KB).

BACKGROUND OF THE INVENTION

Positive and negative costimulatory signals play critical roles in the modulation of T cell activity, and the molecules that mediate these signals have proven to be effective targets for immunomodulatory agents. Positive costimulation, in addition to T cell receptor (TCR) engagement, is required for optimal activation of naive T cells, whereas negative costimulation is believed to be required for the acquisition of immunologic tolerance to self, as well as the termination of effector T cell functions. Upon interaction with B7-1 or B7-2 on the surface of antigen-presenting cells (APC), CD28, the prototypic T cell costimulatory molecule, emits signals that promote T cell proliferation and differentiation in response to TCR engagement, while the CD28 homologue cytotoxic T lymphocyte antigen-4 (CTLA-4) mediates inhibition of T cell proliferation and effector functions (Chambers et al., Ann. Rev. Immunol., 19:565-594, 2001; Egen et al., Nature Immunol., 3:611-618, 2002).

Several new molecules with homology to the B7 family have been discovered (Abbas et al., Nat. Med., 5:1345-6, 1999; Coyle et al., Nat. Immunol., 2: 203-9, 2001; Carreno et al., Annu. Rev. Immunol., 20: 29-53, 2002; Liang et al., Curr. Opin. Immunol., 14: 384-90, 2002), and their role in T cell activation is just beginning to be elucidated. These new costimulatory counter-receptors include B7h2, PD-L1, PD-L2, B7-H3 and B7-H4.

B7h2 (Swallow et al., Immunity, 11: 423-32, 1999), also known as B7RP-1 (Yoshinaga et al., Nature, 402: 827-32, 1999), GL50 (Ling, et al., J. Immunol., 164:1653-7, 2000), B7H2 (Wang et al., Blood, 96: 2808-13, 2000), and LICOS (Brodie et al., Curr. Biol., 10: 333-6, 2000), binds to inducible costimulator (ICOS) on activated T cells, and costimulates T cell proliferation and production of cytokines such as interleukin 4 (IL-4) and IL-10.

PD-L1 (Freeman et al., J. Exp. Med., 192: 1027-34, 2000), also known as B7-H1 in humans (Dong et al., Nat. Med., 5, 1365-9, 1999), and PD-L2 (Latchman et al., Nat. Immunol., 2: 261-8, 2001), also known as B7-DC (Tseng et al., J. Exp. Med., 193, 839-46, 2001) bind to programmed death 1 (PD-1) receptor on T and B cells, although at present the function of these interactions is controversial. Some reports have demonstrated that PD-L 1 and PD-L2 have inhibitory effects on T cell responses (Freeman et al., J. Exp. Med., 192: 1027-34, 2000; Latchman et al., Nat. Immunol., 2: 261-8, 2001), while others have shown that both counter-receptors (B7-R1 and B7-DC) positively regulate T cell proliferation and specifically enhance IL-10 or interferon gamma (IFN-.gamma.) production (Dong et al., Nat. Med., 5, 1365-9, 1999; Tseng et al., J. Exp. Med., 193, 839-46, 2001).

Finally, B7-H3 and B7-H4, both newly identified B7 homologues, bind an as yet currently unknown counter-receptor(s) on activated T cells, and are reported to enhance proliferation of CD4+ T helper (Th) cells and CD8+ cytotoxic T lymphocytes (CTLs or Tcs) and selectively enhance IFN-.gamma. expression (Chapoval et al., Nat. Immunol., 2, 269-74, 2001; Sun et al., J. Immunol., 168, 6294-7, 2002).

With the exception of PD-1 counter-receptors, which show some expression on non-lymphoid tissues, the expression of known B7 family members is largely restricted to lymphoid cells. Collectively, these studies have revealed that B7 family members are counter-receptors on lymphoid cells that interact with cognate receptors on lymphocytes to provide positive or negative costimulatory signals that play critical roles in the regulation of cell-mediated immune responses.

In particular, many autoimmune disorders are known to involve autoreactive T cells and autoantibodies. Agents that are capable of inhibiting or eliminating autoreactive lymphocytes without compromising the immune system's ability to defend against pathogens are highly desirable. Conversely, many cancer immunotherapies, such as adoptive immunotherapy, expand tumor-specific T cell populations and direct them to attack and kill tumor cells (Dudley et al., Science 298:850-854, 2002; Pardoll, Nature Biotech., 20:1207-1208, 2002; Egen et al., Nature Immunol., 3:611-618, 2002). Agents capable of augmenting tumor attack are highly desirable. In addition, immune responses to many different antigens (e.g., microbial antigens or tumor antigens), while detectable, are frequently of insufficient magnitude to afford protection against a disease process mediated by agents (e.g., infectious microorganisms or tumor cells) expressing those antigens. It is often desirable to administer to the subject, in conjunction with the antigen, an adjuvant that serves to enhance the immune response to the antigen in the subject. It is also desirable to inhibit normal immune responses to antigen under certain circumstances. For example, the suppression of normal immune responses in a patient receiving a transplant is desirable, and agents that exhibit such immunosuppressive activity are highly desirable.

Costimulatory signals, particularly positive costimulatory signals, also play a role in the modulation of B cell activity. For example, B cell activation and the survival of germinal center B cells require T cell-derived signals in addition to stimulation by antigen. CD40 counter-receptor present on the surface of helper T cells interacts with CD40 on the surface of B cells, and mediates many such T-cell dependent effects in B cells. Interestingly, negative costimulatory receptors analogous to CTLA-4 have not been identified on B cells. This suggests fundamental differences may exist in the way T cells and B cells are induced to respond to antigen, which has implications for mechanisms of self-tolerance as well as the inhibition of B cell effector functions, such as antibody production. Were a functional CTLA-like molecule to be found on B cells, the finding would dramatically shift our understanding of the mechanisms of B cell stimulation. Further, the identification of such receptors could provide for the development of novel therapeutic agents capable of modulating B cell activation and antibody production, and useful in the modulation of immunologic responses.

Accordingly, there is a need in the art for the identification of additional B7 family members, their counter-receptors and molecules derived therefrom, that have either or both a T cell costimulatory activity and/or a B cell costimulatory activity. This need is based largely on their fundamental biological importance and the therapeutic potential of agents capable of affecting their activity. Such agents capable of modulating costimulatory signals would find significant use in the modulation of immune responses, and are highly desirable.

The present invention provides such polypeptides for these and other uses that should be apparent to those skilled in the art from the teachings herein.

DETAILED DESCRIPTION OF THE INVENTION

1. Overview

The present invention is directed to the identification and characterization of zB7R1, a novel inhibitory lymphocytic receptor, and the discovery of its ability to bind to CD155 (PVR). Thus, the present invention provides a newly identified B7 receptor that is a PD-1-like molecule and is expressed in T lymphocytes. The novel receptor of the present invention is denominated "zB7R1" and is distinct from CD28, CTLA-4, ICOS, PD-1 and B7H1. Methods and compositions for modulating zB7R1-mediated lymphocyte signaling such as, e.g., modulating the natural interaction of zB7R1 and its counter-receptor are also provided, having multiple therapeutic applications for immunological tolerance, autoimmunity, immunosuppression, and immunotherapy including cancer immunotherapy.

As disclosed for the first time herein, zB7R1 acts a negative regulator of T lymphocyte activity, wherein signaling mediated by zB7R1 results in the inhibition of zB7R1-positive lymphocyte activity. In zB7R1-positive T cells zB7R1 signaling could, for instance, inhibit TCR-induced T cell responses, such as cell cycle progression, proliferation, differentiation, survival, cytokine production and cytolytic activation. Further, in zB7R1-positive B cells, zB7R1 signaling could an inhibit B cell antigen receptor-induced B cell responses, such as cell cycle progression, proliferation, differentiation, survival, antigen presentation and antibody production. These findings enable the use of therapeutic agents capable of interfering with the interaction of zB7R1 and its counter-receptor to modulate lymphocyte activity for the purpose of treating, among other conditions, cancer and autoimmune diseases.

CD155 (PVR) was identified as the counterstructure for ZB7r1. CD155 has been reported to be the counterstructure for at least 2 other receptors including CD226 (DNAM-1) and CD96 (Tactile). CD226 and CD96 have been shown to be activating receptors expressed on T cells and NK cells and CD155 can trigger activation through these molecules. CD155 has been reported to be widely expressed in non-hematopoietic tissues and may be overexpressed in a large number of tumors and transformed cell types. The role of CD155 on T cell responses to these tumors is mostly CD155's engagement of zB7R1 which suppresses T and NK cell responses to the tumor. Thus, a reagent that blocks zB7R1-CD155 interaction, including blocking antibodies to either molecule, or soluble forms of either protein, will facilitate T and NK cell responses to the tumor by eliminating or minimizing the inhibitory signal through ZB7r1. Because of the demonstrated inhibitory effect of engaging zB7R1 on T cells with agonistic antibodies as shown herein, agonistic anti-ZB7r1 antibodies or soluble receptors are suitable candidates to suppress T cell responses in T cell mediated inflammatory and autoimmune diseases.

Accordingly, the present invention provides novel uses for zB7R1 modulators, such as zB7R1 agonists or antagonists. These modulators could be a soluble receptor or antibodies to zB7R1 or its counter-receptor, i.e. CD155. The present invention also provides soluble zB7R1 polypeptide fragments and fusion proteins, for use in human inflammatory and autoimmune diseases. The zB7R1 antibodies, and soluble zB7R1 receptors of the present invention, can be used to modulate, agonize, block, increase, inhibit, reduce, antagonize or neutralize the activity of either zB7R1 or its counter-receptor(s) (i.e. CD155) in the treatment of specific human diseases such as cancer, rheumatoid arthritis, psoriasis, psoriatic arthritis, arthritis, endotoxemia, inflammatory bowel disease (IBD), colitis, and other inflammatory conditions disclosed herein.

An illustrative nucleotide sequence that encodes human zB7R1 (also interchangeably known as zB7R1×1 is provided by SEQ ID NO:1; the encoded polypeptide is shown in SEQ ID NO:2. zB7R1 is a B7 receptor that binds to yet another B7 family member, or counter-receptor. Analysis of a human cDNA clone encoding zB7R1 (SEQ ID NO:1) revealed an open reading frame encoding 244 amino acids (SEQ ID NO:2) comprising an extracellular domain of approximately 125 amino acid residues (residues 16-140 of SEQ ID NO:2; SEQ ID NO:3), a transmembrane domain of approximately 23 amino acid residues (residues 141-163 of SEQ ID NO:2), and an intracellular domain of approximately 81 amino acid residues (residues 164 to 244 of SEQ ID NO:2). zB7R1 also has an IgV domain of approximately 96 amino acid residues (residues 32-127 of SEQ ID NO:2).

Within zB7R1, there are two ITIM domains, YFNV (amino acid residues 225-228 of SEQ ID NO:2) and YRSL (amino acid residues 231-234). The presence of an ITIM domain is an indication that zB7R1 can have an inhibitory effect. Within zB7R1, there are also two SH-3-kinase binding domains, PSAP (amino acid residues 191-194 of SEQ ID NO:2) and PSPP (amino acid residues 194-197).

zB7R1 also has a polymorphism at polynucleotide 289 of SEQ ID NO:1, indicated as n, where n can be either C or T. zB7R1 also has at least a second polymorphism at polynucleotide 359 of SEQ ID NO:1, indicated as n, where n can be either A or G, and where the conversion of A to G leads to a change in the amino acid residue 117 of SEQ ID NO:2 (indicated as Xaa) from Thr to Ala.

An another illustrative nucleotide sequence that encodes a variant human zB7R1 (also interchangeably known as zB7R1×2) is provided by SEQ ID NO:5; the encoded polypeptide is shown in SEQ ID NO:6. zB7R1×2 is a B7 receptor that binds to yet another B7 family member, or counter-receptor. Analysis of a human cDNA clone encoding zB7R1×2 (SEQ ID NO:5) revealed an open reading frame encoding 311 amino acids (SEQ ID NO:6) comprising an extracellular domain of approximately 182 amino acid residues (residues 27-208 of SEQ ID NO:6; SEQ ID NO:7), a transmembrane domain of approximately 22 amino acid residues (residues 209-230 of SEQ ID NO:6), and an intracellular domain of approximately 81 amino acid residues (residues 231 to 311 of SEQ ID NO:6).

An illustrative nucleotide sequence that encodes a murine zB7R1 is provided by SEQ ID NO:8; the encoded polypeptide is shown in SEQ ID NO:9. The extracellular domain is shown in SEQ ID NO:10.

An illustrative nucleotide sequence that encodes human CD155 (also interchangeably known as PVR) is provided by SEQ ID NO:17; the encoded polypeptide is shown in SEQ ID NO:18. CD155 has been shown to bind to zB7R1 and thus is a counter-receptor for this B7 family member. Analysis of a human cDNA clone encoding zB7R1 (SEQ ID NO:17) revealed an open reading frame encoding 417 amino acids (SEQ ID NO:18) comprising an extracellular domain of approximately 316 amino acid residues (residues 28-343 of SEQ ID NO:18; SEQ ID NO:19), a transmembrane domain of approximately 24 amino acid residues (residues 344-367 of SEQ ID NO:18), and an intracellular domain of approximately 50 amino acid residues (residues 368-417 of SEQ ID NO:18).

An illustrative nucleotide sequence that encodes a murine CD155 is provided by SEQ ID NO:20; the encoded polypeptide is shown in SEQ ID NO:21. The extracellular domain is shown in SEQ ID NO:22. Analysis of a cDNA clone encoding murine CD155 revealed an open reading frame encoding 408 amino acids (SEQ ID NO:21) comprising an extracellular domain of approximately 319 amino acid residues (residues 29-347 of SEQ ID NO:21; SEQ ID NO:22), a transmembrane domain of approximately 20 amino acid residues (residues 348-367 of SEQ ID NO:21), and an intracellular domain of approximately 40 amino acid residues (residues 368-408 of SEQ ID NO:21)

Accordingly, in one aspect of the present invention, the present invention provides nucleic acid sequences encoding zB7R1 polypeptides, which are useful in the modulation of T lymphocyte activity and in the treatment of immune disorders, including autoimmune diseases, inflammation, psoriasis, IBD, ulcerative colitis and SLE.

The present invention also provides isolated polypeptides and epitopes comprising at least 15 contiguous amino acid residues of an amino acid sequence of SEQ ID NO:2 or 3. Illustrative polypeptides include polypeptides that either comprise, or consist of SEQ ID NO:3, an antigenic epitope thereof, or a functional zB7R1 binding fragment thereof. Moreover, the present invention also provides isolated polypeptides as disclosed above that agonize, bind to, block, inhibit, reduce, increase, antagonize or neutralize the activity of zB7R1.

The present invention further provides antibodies and antibody fragments that specifically bind with such polypeptides. Exemplary antibodies include agonist antibodies, neutralizing antibodies, polyclonal antibodies, murine monoclonal antibodies, humanized antibodies derived from murine monoclonal antibodies, and human monoclonal antibodies. Illustrative antibody fragments include F(ab')$_2$, F(ab)$_2$, Fab', Fab, Fv, scFv, and minimal recognition units. Neutralizing antibodies preferably bind zB7R1 such that its interaction with its counter-receptor or counter-receptors is blocked, inhibited, reduced, antagonized or neutralized; anti-zB7R1 neutralizing antibodies such that its interaction with its counter-receptor or counter-receptors is blocked, inhibited, reduced, antagonized or neutralized are also encompassed by the present invention. The present invention further includes compositions comprising a carrier and a peptide, polypeptide, or antibody described herein.

Thus, in one embodiment, antagonists of zB7R1 signaling are provided for increasing T cell activation, and possibly B cell activation. In a preferred embodiment, such antagonists comprise blocking agents capable of interfering with the natural interaction of zB7R1 with its counter-receptor or counter-receptors, thereby inhibiting zB7R1-mediated negative signaling and resulting in an increase in lymphocyte activation and proliferation and effector function.

In an alternative embodiment, agonists of zB7R1 signaling are provided for inhibiting T cell activation, and possibly B cell activation. In a preferred embodiment, such bioactive agents comprise mimicking agents capable of binding to zB7R1 and mimicking and/or augmenting the natural interaction of zB7R1 with its counter-receptor or counter-receptors, thereby resulting in inhibition of T cell activation (and possibly B cell) and proliferation and effector function.

In one embodiment, bioactive agents and methods for increasing and/or up-regulating B and T cell activity are provided. In a preferred embodiment, such bioactive agents comprise antagonists of zB7R1-mediated signaling. In a particularly preferred embodiment, such bioactive agents comprise blocking agents as described herein, and in a specific embodiment, such blocking agents are capable of interfering with the interaction of zB7R1 and Its counter-receptor. In a further embodiment, adjuvant compositions are provided utilizing zB7R1 and/or Its counter-receptor blocking agents and other antagonists of zB7R1-mediated signaling.

In an alternative embodiment, bioactive agents and methods for inhibiting and/or down-regulating B and T cell activity are provided. In a preferred embodiment, such bioactive agents comprise agonists of zB7R1-mediated signaling. In a particularly preferred embodiment, such bioactive agents comprise mimicking agents as described herein, and in a specific embodiment, such mimicking agents are capable of replacing and/or augmenting the interaction of zB7R1 and Its counter-receptor. In a further embodiment, immunosuppressive compositions are provided utilizing zB7R1 and/or Its counter-receptor mimicking agents and other agonists of zB7R1-mediated signaling.

In a further embodiment, methods and compositions for modulating immunoglobulin production by B cells is provided.

The methods and compositions described herein will find advantageous use in immunotherapy, including, e.g., autoimmunity, immune suppression, cancer immunotherapy and immune adjuvants.

In addition, the present invention also provides pharmaceutical compositions comprising a pharmaceutically acceptable carrier and at least one of such an expression vector or recombinant virus comprising such expression vectors. The present invention further includes pharmaceutical compositions, comprising a pharmaceutically acceptable carrier and a polypeptide or antibody described herein.

The present invention also contemplates anti-idiotype antibodies, or anti-idiotype antibody fragments, that specifically bind an antibody or antibody fragment that specifically binds a polypeptide comprising the amino acid sequence of SEQ ID NO:2 or 6 or a fragment thereof. An exemplary anti-idiotype antibody binds with an antibody that specifically binds a polypeptide consisting of SEQ ID NO:3 or 7.

The present invention also provides fusion proteins, comprising a zB7R1 polypeptide and an immunoglobulin moiety. In such fusion proteins, the immunoglobulin moiety may be an immunoglobulin heavy chain constant region, such as a human $F_c$ fragment. The present invention further includes isolated nucleic acid molecules that encode such fusion proteins.

The present invention relates to a multimeric zB7R1 protein, as well as a method of preparing such a multimeric protein, preferably a tetrameric protein, comprising culturing a host cell transformed or transfected with an expression vector encoding a fusion protein comprising a vasodialator-stimulated phosphoprotein (VASP) domain and a heterologous protein, such as zB7R1 or CD155. Specifically, the portion of zB7R1 or CD155 that is included in the fusion protein is the extracellular domain of that protein (i.e. SEQ ID NO:3 or 7 for zB7R1, or SEQ ID NO:22 for CD155), and the resulting fusion protein is soluble. In a further embodiment, the fusion protein comprises a linker sequence. In still another embodiment of the present invention, the VASP domain can be used to identify sequences having similar protein structure patterns and those similar domains are used to make a fusion protein that multimerizes a heterologous protein or protein domain.

A further embodiment of the present invention is a method of preparing a soluble, homo- or hetero-tetrameric zB7R1 or CD155 protein by culturing a host cell transformed or transfected with at least one, but up to four different expression vectors encoding a fusion protein comprising a VASP domain and a heterologous protein such as zB7R1 or CD155 or protein domain thereof. In this embodiment, the four VASP domains preferentially form a homo- or hetero-tetramer. This culturing can occur in the same or different host cells. The VASP domains can be the same or different and the fusion protein can further comprise a linker sequence. The present invention also encompasses DNA sequences, expression vectors, and transformed host cells utilized in the present method and fusion proteins produced by the present method.

The present invention also provides polyclonal and monoclonal antibodies that bind to polypeptides comprising a zB7R1 extracellular domain such as monomeric, homodimeric, heterodimeric and multimeric receptors, including soluble receptors.

In another aspect, methods for modulating lymphocyte activity are provided comprising contacting a B and/or T lymphocyte with a bioactive agent capable of modulating zB7R1 activity. In one embodiment, the bioactive agent comprises an antagonist of zB7R1 activity such as, e.g., a zB7R1 or a zB7R1 counter-receptor blocking agent (i.e. CD155) resulting in an upregulation or increase in lymphocyte activity by preventing negative zB7R1-mediated signaling. In an alternative embodiment, the bioactive agent comprises an agonist of zB7R1 activity such as, e.g., a zB7R1 or a zB7R1 counter-receptor mimicking agent, resulting in down-regulation of lymphocyte activity by replacing or augmenting zB7R1-mediated negative signaling.

In a further aspect, methods for modulating lymphocyte activity are provided comprising contacting a B and/or T lymphocyte with a bioactive agent capable of modulating the interaction of zB7R1 with a zB7R1 counter-receptor. In one embodiment, a bioactive agent capable of interfering with the natural interaction of zB7R1 and a zB7R1 counter-receptor (i.e. CD155) is employed to increase lymphocyte activity and proliferation such as, e.g., a zB7R1 antagonist such as a soluble zB7R1 counter-receptor or a zB7R1 blocking agent. In an alternative embodiment, a bioactive agent capable augmenting or replacing the natural interaction of zB7R1 and a zB7R1 counter-receptor (i.e. CD155) is employed to inhibit lymphocyte activity and proliferation.

Suitable zB7R1 blocking agents may be selected from the group comprising or consisting of soluble zB7R1 polypeptides and fusion proteins, anti-zB7R1 antibodies capable of binding to at least a portion of the extracellular domain of zB7R1 and interfering with zB7R1-mediated signaling, small molecule inhibitors of zB7R1 receptor interaction with its ligands, and the like. Alternative zB7R1 antagonists further include antisense oligonucleotides directed to the zB7R1 nucleic acid sequence, inhibitory RNA sequences, small molecule inhibitors of zB7R1 expression and/or intracellular signaling, and the like.

Similarly, suitable zB7R1 counter-receptor blocking agents or antagonists may be selected from the group comprising or consisting of anti-zB7R1 counter-receptor antibodies capable of binding to at least a portion of the extracellular domain of a zB7R1 counter-receptor (i.e. CD155; SEQ ID NO:22) and interfering with the interaction of a zB7R1 counter-receptor and zB7R1, small molecule inhibitors of the interaction between a zB7R1 counter-receptor and zB7R1, soluble a zB7R1 counter-receptor polypeptides and fusion proteins having modified a zB7R1 counter-receptor amino acid sequences so as to interfere with the interaction of a zB7R1 counter-receptor and zB7R1 and incapable of activating zB7R1-mediated signaling, and the like. Alternative a zB7R1 counter-receptor antagonists include antisense oligonucleotides directed to the zB7R1 counter-receptor nucleic acid sequence (i.e. CD155; SEQ ID NO:20), inhibitory RNA molecules, small molecule inhibitors of a zB7R1 counter-receptor expression, and the like.

Suitable zB7R1 mimicking agents or agonists may be selected from the group comprising or consisting of function-activating anti-zB7R1 antibodies ("agonistic antibodies") capable of binding to at least a portion of the extracellular domain of zB7R1 (SEQ ID NO:3 or 7) and stimulating zB7R1-mediated signaling, gene therapy vectors capable of recombinantly producing functional zB7R1 molecules intracellularly, small molecule enhancers of zB7R1 expression and/or zB7R1-mediated signaling, and the like. Similarly, suitable a zB7R1 counter-receptor mimicking agents may be selected from the group comprising or consisting of soluble a zB7R1 counter-receptor polypeptides, such as CD155, and fusion proteins capable of activating zB7R1-mediated signaling, small molecule enhancers of the interaction between a zB7R1 counter-receptor and zB7R1 as well as enhancers of a zB7R1 counter-receptor expression, gene therapy vectors capable of recombinantly producing functional a zB7R1 counter-receptor molecules intracellularly, and the like.

Thus, in a more specific embodiment methods for stimulating, augmenting and/or increasing lymphocyte activity are provided comprising contacting a B or T lymphocyte with an antagonist of zB7R1-mediated signaling, said antagonist comprising at least one bioactive agent selected from the group consisting of soluble zB7R1 polypeptides, soluble zB7R1 fusion proteins, anti-zB7R1 antibodies capable of binding to at least a portion of the extracellular domain of zB7R1 and interfering with zB7R1-mediated signaling, small molecule inhibitors of zB7R1 expression and/or zB7R1-mediated signaling, anti-zB7R1 counter-receptor antibodies capable of binding to at least a portion of the extracellular domain of a zB7R1 counter-receptor and interfering with the interaction of a zB7R1 counter-receptor and zB7R1, small molecule inhibitors of the interaction between a zB7R1 counter-receptor and zB7R1, soluble a zB7R1 counter-receptor polypeptides and a zB7R1 counter-receptor fusion proteins incapable of activating zB7R1-mediated signaling, and interfering RNA sequences.

In a particularly preferred embodiment, methods for increasing a host immune response to antigenic stimulation are provided, comprising the administration to the host of at least one of the aforementioned antagonists of zB7R1- mediated signaling. Desirably, the antigenic stimulation may be from pathogen antigens, vaccine antigens and/or tumor antigens.

In a specific embodiment, methods for stimulating a cellular immune response against tumor antigens other than a zB7R1 counter-receptor are provided, comprising administering to a cancer patient at least one of the subject antagonists or blocking agents to inhibit zB7R1-mediated negative signaling and thereby increase the T cell response directed against tumor antigens other than a zB7R1 counter-receptor present in the cancerous tissue.

In a further specific embodiment methods for inhibiting, attenuating and/or decreasing lymphocyte activity are provided comprising contacting a B or T lymphocyte with an agonist of zB7R1-mediated signaling, said agonist selected from the group consisting of soluble a zB7R1 counter-receptor polypeptides and a zB7R1 counter-receptor fusion proteins capable of activating zB7R1-mediated signaling, function-activating anti-zB7R1 antibodies capable of binding to at least a portion of the extracellular domain of zB7R1 and stimulating zB7R1-mediated signaling, gene therapy vectors capable of recombinantly producing functional zB7R1 molecules intracellularly, small molecule enhancers of zB7R1 expression and/or zB7R1-mediated signaling, small molecule enhancers of the interaction between a zB7R1 counter-receptor and zB7R1, small molecule enhancers of a zB7R1 counter-receptor expression, and gene therapy vectors capable of recombinantly producing functional a zB7R1 counter-receptor molecules intracellularly.

In a particularly preferred embodiment, methods for suppressing a host immune response to antigenic stimulation are provided, comprising the administration to the host of at least one of the aforementioned agonists of zB7R1-mediated signaling. Desirably, the antigenic stimulation may be from self antigens in the context of autoimmune disease, or from donor antigens present in transplanted organs and tissues.

In an alternative aspect, the present invention provides bioactive agents and methods for modulating the interaction of a zB7R1 counter-receptor-expressing cell and a zB7R1-expressing lymphocyte. In a preferred embodiment, bioactive agents and methods for interfering with the interaction of a zB7R1 counter-receptor—positive tumor cells with T cells are provided, resulting in inhibition of negative zB7R1-mediated signaling. In an especially preferred embodiment, the T cell is a CD4+ cell or a CD8+ cell. In a further embodiment, the CD4+ T cell is a Th1 cell.

In another preferred embodiment, bioactive agents and methods for mimicking or enhancing the interaction of a zB7R1 counter-receptor/CD155-positive non-tumor non-lymphoid cells with zB7R1-positive T cells are provided, thereby decreasing T cell activity. In an especially preferred embodiment, the T cell is a CD4+ T cell or a CD8+ T cell. In a further embodiment, the CD4+ T cell is a Th1 cell.

In a further aspect, methods for treating cancers characterized by the presence of a zB7R1 counter-receptor—expressing tumor cells are provided. In one embodiment, these methods comprise administering to a mammalian subject at least one of the antagonists of zB7R1-mediated signaling disclosed herein, either alone or in conjunction with alternative cancer immunotherapy, chemotherapy and/or radiotherapy protocols. In a preferred embodiment, at least one zB7R1 antagonist or CD155 antagonist is administered to a subject having a zB7R1 counter-receptor—positive tumor cells, wherein said blocking agent is capable of interfering with the interaction of zB7R1 and a zB7R1 counter-receptor and inhibiting zB7R1-mediated signaling. Preferably, administration of said blocking agents is effective to increase T cell activity directed against tumor antigens other than a zB7R1 counter-receptor on the tumor cells, and in particular, to increase cytotoxic T cell activity. Still more preferably, administration of the subject antagonists is effective to inhibit the growth of the a zB7R1 counter-receptor—expressing tumor cells.

It is also contemplated that the subject zB7R1 and/or a zB7R1 counter-receptor/CD155 blockade provided herein may find synergistic combination with CTLA-4 blockade as described in U.S. Pat. Nos. 5,855,887; 5,811,097; and 6,051,227, and International Publication WO 00/32231, the disclosures of which are expressly incorporated herein by reference.

In a further aspect, methods for treating autoimmune disorders characterized by the absent or aberrant expression of a zB7R1 counter-receptor in non-tumor non-lymphoid host cells subjected to autoimmune attack are provided. In one embodiment, these methods comprise administering to a mammalian subject at least one of the agonists of zB7R1-mediated signaling disclosed herein, either alone or in conjunction with alternative immunotherapy and/or immunosuppressive protocols. In a preferred embodiment, at least one zB7R1 or CD15 agonist is administered to a subject having autoreactive zB7R1-positive lymphocytes, wherein said agonist is capable of replacing and/or augmenting the interaction of zB7R1 and CD155 and replacing or increasing zB7R1-mediated signaling. Preferably, administration of said agonists is effective in decreasing autoreactive lymphocyte activity directed against non-tumor non-lymphoid host cells, and particularly autoreactive CD8+CTL and CD4+ Th1 activity, and B cell activity.

In a still further aspect, methods for improving the outcome of organ and tissue transplantation and prolonging graft survival are provided. In one embodiment, these methods comprise administering to a transplant recipient at least one agent of the agonists or antagonists of zB7R1-mediated signaling disclosed herein, either alone or in conjunction with alternative immunotherapy and/or immunosuppressive protocols. In a preferred embodiment, at least one zB7R1 mimicking agent (for instance a soluble receptor that blocks binding a cell-surface zB7R1 to its counter-receptor, or an agonist antibody that binds to zB7R1 and induces signaling) is administered to the transplant recipient, wherein said mimicking agent is capable of replacing and/or augmenting the interaction of zB7R1 and a zB7R1 counter-receptor and replacing or increasing zB7R1-mediated signaling. Preferably, administration of said mimicking agents is effective to decrease the recipient immune response against donor antigens present in the graft, particularly the cytolytic CTL response and the B cell response. Still more preferably, administration of the subject mimicking agents is effective to bias to T helper cell response from an unfavorable Th-1 type response to a more favorable Th-2 type response, as described in more detail herein.

Treatment of Autoimmune Disease

The present invention also provides compositions and methods for inhibiting autoimmune responses. In a preferred embodiment, compositions and methods for inhibiting the activity of autoreactive T and B cells that specifically recognize autoantigens are provided. Desirably, these compositions and methods may be used to inhibit killing of non-tumor cells mediated by one or more autoantigens.

Preferred compositions for use in the treatment of autoimmune disease comprise agents that mediate zB7R1 signaling described herein including, e.g., the above-described mimicking agents, agonists or antagonists. Especially preferred agents include zB7R1 protein fragments comprising the zB7R1 extracellular domain (SEQ ID NO:3 or 7), or a portion thereof; zB7R1-Ig fusion proteins comprising the zB7R1 extracellular domain (SEQ ID NO:3), or a portion thereof; function-activating anti-zB7R1 or CD155 antibodies; peptides that mimic zB7R1 or its counter-receptor, CD155 (mimetics); and small molecule chemical compositions that mimic the natural interaction of zB7R1 with its counter-receptor. Also preferred are compositions capable of binding to zB7R1, either in a cross-linking fashion or as polyclonal mixtures.

Also contemplated in the present invention are genetic approaches to autoimmune disease. Particularly, gene therapy may be used to increase the level of zB7R1 expression on T cells, and/or increase the level of expression of its counter-receptor on non-lymphoid cells that are subject to attack by autoreactive lymphocytes. The use of isoforms or variants of zB7R1 that exhibit elevated specific activity is also contemplated, the object of each method being to potentiate signaling that is suppressive to T cell activation.

The present invention also provides compositions and methods for treating cancer, and in particular, for increasing the activity of zB7R1-positive lymphocytes against B7-positive tumor cells. Desirably, these compositions and methods may be used to inhibit the growth of tumor cells capable of expressing a B7 family member.

Preferred compositions for use in the treatment of cancer are the antagonists of zB7R1-mediated signaling described herein including, e.g., zB7R1 blocking agents. Especially preferred agents include anti-zB7R1 antibodies; protein fragments comprising the zB7R1 extracellular domain, or a portion thereof; zB7R1-Ig fusion proteins comprising the BTLA extracellular domain, or a portion thereof; function-blocking anti-zB7R1 antibody; peptides that mimic zB7R1 (mimetics); and small molecule chemical compositions that interfere with the natural interaction of zB7R1 and its counter-receptor.

Also contemplated in the present invention are genetic approaches to the treatment of cancer. Particularly, gene therapy may be used to decrease the level of zB7R1 expression on T cells, and/or decrease the level of expression of zB7R1 or its counter-receptor (i.e. CD155) on tumor cells. The use of isoforms of zB7R1 that exhibit dominant negative activity is also contemplated, the object of each method being to inhibit signaling that is normally suppressive to T cell activation. Genetic approaches may involve the use of tissue and cell specific promoters to target expression of zB7R1 dominant negative variants, antisense nucleic acids, or small inhibitory RNAs to T cells and tumor cells, respectively. The methods may additionally involve the use of tumor-targeted viruses, or other delivery vehicles that specifically recognize tumor cells. The methods may additionally involve the use of T cell-targeted viruses, or other delivery vehicles that specifically recognize T cells.

Particularly preferred are agents that may be selectively targeted to tumor cells, and effect a decrease in zB7R1 expression in tumor cells without reducing the level of zB7R1 expression in non-tumor cells to deleterious levels. Highly preferred are agents that have a precursor form. These "prodrugs" are converted to their active form in the vicinity of tumor tissue typically by an enzymatic activity that is restricted in its distribution to the vicinity of the tumor.

Also highly preferred are agents that can be combined with targeting moieties that selectively deliver the agent to a tumor. These targeting moieties provide a high local concentration of the agent in the vicinity of the tumor tissue, and reduce the amount of agent that must be administered to effect the desired response.

Also contemplated in the present invention is the use of combination therapy to treat cancer, as described above.

In a preferred embodiment, immunization is done to promote a tumor-specific T cell immune response. In this embodiment, a bioactive agent that inhibits zB7R1 activation is administered in combination with a tumor-associated antigen. The combination of a tumor-associated antigen and a zB7R1-inhibitory/counter-receptor functional-mimetic promotes a tumor specific T cell response, in which T cells encounter a lower level of inhibition than exerted by the tumor tissue in the absence of the bioactive agent.

In one aspect, the present invention provides a medicament for the treatment of cancer.

The present invention also provides compositions and methods for modulating normal but undesired immune responses involving T and B cell activity. In a preferred embodiment, compositions and methods for inhibiting the host lymphocyte response to transplanted tissue and organs are provided. Desirably, these compositions and methods may be used to prolong the survival of grafted tissue. Preferred compositions for use in the prevention of acute and/or chronic graft rejection comprise the agonists of zB7R1-mediated signaling described herein including, e.g., the above-described mimicking agents. Especially preferred agents include zB7R1 polypeptides comprising the zB7R1 extracellular domain (SEQ ID NO:3 or 7), or a portion thereof; zB7R1-Ig fusion proteins comprising the zB7R1 extracellular domain (SEQ ID NO:3 or 7), or a portion thereof; function-activating anti-BTLA antibodies; peptides that mimic its counter-receptor (i.e. CD155) (mimetics); and small molecule chemical compositions that mimic the natural interaction of zB7R1 and its counter-receptor. In addition to their utility in general immunosuppressive strategies, the subject agonists of zB7R1-mediated signaling described herein may also have important implications for tolerance induction in tissue and organ transplantation, by biasing the recipient T helper cell immune response away from an unfavorable Th-l-type response and towards a more favorable Th-2 type response.

In one aspect, the present invention provides a medicament for use in transplantation and immune suppression.

Also provided are adjuvant compositions comprising at least one of the above-described zB7R1 and/or CD155 or other zB7R1 counter-receptor blocking agents as well as other antagonists of zB7R1-mediated signaling. Also provided are immunosuppressant compositions comprising at least one of the above-described zB7R1 and/or a zB7R1 counter-receptor mimicking agents as well as other agonists of zB7R1-mediated signaling.

It is further contemplated that the subject compositions and methods may be synergistically combined with immunotherapies based on modulation of other T cell costimulatory pathways, and with ICOS, PD-1, CTLA-4 and/or BTLA modulation in particular.

In an alternative aspect, the present invention provides methods of screening for bioactive agents that are useful for modulating T cell activation. Bioactive agents identified by the screening methods provided herein may be used to react with a zB7R1 counter-receptor-expressing cells or zB7R1-expressing cells in order to interfere with the interaction between zB7R1-expressing B and/or T cells and a zB7R1 counter-receptor—expressing non-lymphoid cells, and thereby antagonize the function of the zB7R1/a zB7R1 counter-receptor interaction. Alternatively, bioactive agents may be used to react with a zB7R1 counter-receptor-expressing cells or zB7R1-expressing cells in order to mimic the a zB7R1 counter-receptor/zB7R1 interaction, effecting T cell inhibition in the absence of a zB7R1/zB7R1 counter-receptor interaction. Alternatively, bioactive agents may be used to modify the natural zB7R1/CD155 (or zB7R1 with another zB7R1 counter-receptor) interaction in some way, for example, to increase the association and augment the inhibitory signal.

In an alternative aspect, the invention provides expression vectors comprising the isolated zB7R1 and/or a zB7R1 counter-receptor nucleic acid sequences disclosed herein (i.e. CD155; SEQ ID NO:20), recombinant host cells comprising the recombinant nucleic acid molecules disclosed herein, and methods for producing zB7R1 and/or zB7R1 counter-receptor polypeptides comprising culturing the host cells and optionally isolating the polypeptide produced thereby.

In a further aspect, transgenic non-human mammals are provided comprising a nucleic acid encoding a zB7R1, a CD155 and/or another zB7R1 counter-receptor protein as disclosed herein. The zB7R1, CD155 or other zB7R1 counter-receptor nucleotides are introduced into the animal in a manner that allows for increased expression of levels of a zB7R1 or a zB7R1 counter-receptor polypeptide, which may include increased circulating levels. Alternatively, the zB7R1, Cd155 or a zB7R1 counter-receptor nucleic acid fragments may be used to target endogenous zB7R1, CD155 or a zB7R1 counter-receptor alleles in order to prevent expression of endogenous zB7R1 or a zB7R1 counter-receptor nucleic acids (i.e. generates a transgenic animal possessing a zB7R1 or a zB7R1 counter-receptor protein gene knockout). The transgenic animal is preferably a mammal, and more preferably a rodent, such as a rat or a mouse.

These and other aspects of the invention will become evident upon reference to the following detailed description. In addition, various references are identified below and are incorporated by reference in their entirety.

2. Definitions

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J Biol. Chem.* 267:19938 (1992)), AP2 (Ye et al., *J Biol. Chem.* 269:25728 (1994)), SP1, cAMP response element binding protein (CREB; Loeken, *Gene Expr.* 3:253 (1993))

and octamer factors (see, in general, Watson et al., eds., *Molecular Biology of the Gene,* 4th ed. (The Benjamin/Cummings Publishing Company, Inc. 1987), and Lemaigre and Rousseau, *Biochem.* 1 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces zB7R1 from an expression vector. In contrast, zB7R1 can be produced by a cell that is a "natural source" of zB7R1, and that lacks an expression vector.

"Integrative transformants" are recombinant host cells, in which heterologous DNA has become integrated into the genomic DNA of the cells.

A "fusion protein" is a hybrid protein expressed by a nucleic acid molecule comprising nucleotide sequences of at least two genes. For example, a fusion protein can comprise at least part of a zB7R1 polypeptide fused with a polypeptide that binds an affinity matrix. Such a fusion protein provides a means to isolate large quantities of zB7R1 using affinity chromatography.

The term "receptor" denotes a cell-associated protein that binds to a bioactive molecule termed a "counter-receptor." This interaction mediates the effect of the counter-receptor on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular counter-receptor-binding domain and an intracellular effector domain that is typically involved in signal transduction. In certain membrane-bound receptors, the extracellular counter-receptor-binding domain and the intracellular effector domain are located in separate polypeptides that comprise the complete functional receptor.

In general, the binding of counter-receptor to receptor results in a conformational change in the receptor that causes an interaction between the effector domain and other molecule(s) in the cell, which in turn leads to an alteration in the metabolism of the cell. Metabolic events that are often linked to receptor-counter-receptor interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

A "soluble receptor" is a receptor polypeptide that is not bound to a cell membrane. Soluble receptors are most commonly counter-receptor-binding polypeptides that lack transmembrane and cytoplasmic domains, and other linkage to the cell membrane such as via glycophosphoinositol (gpi). Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis or translated from alternatively spliced mRNAs.

Soluble receptors can be monomeric, homodimeric, heterodimeric, or multimeric, with multimeric receptors generally not comprising more than 9 subunits, preferably not comprising more than 6 subunits, and most preferably not comprising more than 3 subunits. Receptor polypeptides are said to be substantially free of transmembrane and intracellular polypeptide segments when they lack sufficient portions of these segments to provide membrane anchoring or signal transduction, respectively. For example, representative soluble receptors for zB7R1 include, for instance the soluble receptor as shown in SEQ ID NO:3 or 7. It is well within the level of one of skill in the art to delineate what sequences of a known B7 family member comprise the extracellular domain free of a transmembrane domain and intracellular domain. Moreover, one of skill in the art using the genetic code can readily determine polynucleotides that encode such soluble receptor polypeptides.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, such as 96%, 97%, or 98% or more pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

As used herein, the term "immunomodulator" includes cytokines, stem cell growth factors, lymphotoxins, co-stimulatory molecules, hematopoietic factors, and the like, and synthetic analogs of these molecules.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/counter-receptor pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9$ $M^{-1}$.

An "anti-idiotype antibody" is an antibody that binds with the variable region domain of an immunoglobulin. In the present context, an anti-idiotype antibody binds with the variable region of an anti-zB7R1 antibody, and thus, an anti-idiotype antibody mimics an epitope of zB7R1.

An "antibody fragment" is a portion of an antibody such as $F(ab')_2$, $F(ab)_2$, Fab', Fab, and the like. Regardless of structure, an antibody fragment binds with the same antigen that is recognized by the intact antibody. For example, an anti-zB7R1 monoclonal antibody fragment binds with an epitope of zB7R1.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A "chimeric antibody" is a recombinant protein that contains the variable domains and complementary determining regions derived from a rodent antibody, while the remainder of the antibody molecule is derived from a human antibody.

"Humanized antibodies" are recombinant proteins in which murine complementarity determining regions of a monoclonal antibody have been transferred from heavy and light variable chains of the murine immunoglobulin into a human variable domain. Construction of humanized antibodies for therapeutic use in humans that are derived from murine antibodies, such as those that bind to or neutralize a human protein, is within the skill of one in the art.

As used herein, a "therapeutic agent" is a molecule or atom which is conjugated to an antibody moiety to produce a conjugate which is useful for therapy. Examples of therapeutic agents include drugs, toxins, immunomodulators, chelators, boron compounds, photoactive agents or dyes, and radioisotopes.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO 1* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). DNA molecules encoding affinity tags are available from commercial suppliers (e.g., Pharmacia Biotech, Piscataway, N.J.).

A "naked antibody" is an entire antibody, as opposed to an antibody fragment, which is not conjugated with a therapeutic agent. Naked antibodies include both polyclonal and monoclonal antibodies, as well as certain recombinant antibodies, such as chimeric and humanized antibodies.

As used herein, the term "antibody component" includes both an entire antibody and an antibody fragment.

An "immunoconjugate" is a conjugate of an antibody component with a therapeutic agent or a detectable label.

As used herein, the term "antibody fusion protein" refers to a recombinant molecule that comprises an antibody component and a zB7R1 polypeptide component. Examples of an antibody fusion protein include a protein that comprises a zB7R1 extracellular domain, and either an Fc domain or an antigen-binding region.

A "target polypeptide" or a "target peptide" is an amino acid sequence that comprises at least one epitope, and that is expressed on a target cell, such as a tumor cell, or a cell that carries an infectious agent antigen. T cells recognize peptide epitopes presented by a major histocompatibility complex molecule to a target polypeptide or target peptide and typically lyse the target cell or recruit other immune cells to the site of the target cell, thereby killing the target cell.

An "antigenic peptide" is a peptide which will bind a major histocompatibility complex molecule to form an MHC-peptide complex which is recognized by a T cell, thereby inducing a cytotoxic lymphocyte response upon presentation to the T cell. Thus, antigenic peptides are capable of binding to an appropriate major histocompatibility complex molecule and inducing a cytotoxic T cells response, such as cell lysis or specific cytokine release against the target cell which binds or expresses the antigen. The antigenic peptide can be bound in the context of a class I or class II major histocompatibility complex molecule, on an antigen presenting cell or on a target cell.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

An "anti-sense oligonucleotide specific for zB7R1" or a "zB7R1 anti-sense oligonucleotide" is an oligonucleotide having a sequence (a) capable of forming a stable triplex with a portion of the zB7R1 gene, or (b) capable of forming a stable duplex with a portion of an mRNA transcript of the zB7R1 gene.

A "ribozyme" is a nucleic acid molecule that contains a catalytic center. The term includes RNA enzymes, self-splicing RNAs, self-cleaving RNAs, and nucleic acid molecules that perform these catalytic functions. A nucleic acid molecule that encodes a ribozyme is termed a "ribozyme gene."

An "external guide sequence" is a nucleic acid molecule that directs the endogenous ribozyme, RNase P, to a particular species of intracellular mRNA, resulting in the cleavage of the mRNA by RNase P. A nucleic acid molecule that encodes an external guide sequence is termed an "external guide sequence gene."

The term "variant zB7R1 gene" refers to nucleic acid molecules that encode a polypeptide having an amino acid sequence that is a modification of SEQ ID NO:2 (i.e. SEQ ID NO:6). Such variants include naturally-occurring polymorphisms of zB7R1 genes, as well as synthetic genes that contain conservative amino acid substitutions of the amino acid sequence of SEQ ID NO:2. Additional variant forms of zB7R1 genes are nucleic acid molecules that contain insertions or deletions of the nucleotide sequences described herein. A variant zB7R1 gene can be identified, for example, by determining whether the gene hybridizes with a nucleic acid molecule having the nucleotide sequence of SEQ ID NO:1, or its complement, under stringent conditions.

Alternatively, variant zB7R1 genes can be identified by sequence comparison. Two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using standard software programs such as those included in the LASER-GENE bioinformatics computing suite, which is produced by DNASTAR (Madison, Wis.). Other methods for comparing two nucleotide or amino acid sequences by determining optimal alignment are well-known to those of skill in the art (see, for example, Peruski and Peruski, *The Internet and the New Biology: Tools for Genomic and Molecular Research* (ASM Press, Inc. 1997), Wu et al. (eds.), "Information Superhighway and Computer Databases of Nucleic Acids and Proteins," in *Methods in Gene Biotechnology*, pages 123-151 (CRC Press, Inc. 1997), and Bishop (ed.), *Guide to Human Genome Computing*, 2nd Edition (Academic Press, Inc. 1998)). Particular methods for determining sequence identity are described below.

Regardless of the particular method used to identify a variant zB7R1 gene or variant zB7R1 polypeptide, a variant gene or polypeptide encoded by a variant gene may be functionally characterized the ability to bind specifically to an anti-zB7R1 antibody. A variant zB7R1 gene or variant zB7R1 polypeptide may also be functionally characterized the ability to bind to its counter-receptor or counter-receptors, using a biological or biochemical assay described herein.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

As used herein, the term "immune response" includes both T and/or B cell responses, i.e., cellular and/or humoral immune responses. In one embodiment, the compositions and methods disclosed herein can be used to reduce or enhance helper T cell (Th) responses, and more preferably, Th1 cell responses. In another embodiment, the compositions and methods disclosed herein can be used to reduce or, enhance cytotoxic T cell (Tc) responses. The claimed methods can be used to reduce or enhance both primary and secondary immune responses and effector function (e.g., cytolytic activity, cytokine and antibody production, and antigen presentation). The immune response of a subject can be readily determined by the skilled artisan using methods well known in the art, for example, by assaying for antibody production, immune cell proliferation, the release of cytokines, the expression of cell surface markers, cytotoxicity, etc.

By "zB7R1 signaling", "zB7R1-mediated signaling", "zB7R1-mediated negative signaling" and variations thereof is meant intracellular signaling in lymphocytes caused by the binding and/or activation of the zB7R1 receptor by its corresponding ligand(s) resulting in attenuation and/or down-regulation of lymphocyte activity. In one aspect, zB7R1-mediated signaling comprises activation of SHP-1 and/or SHP-2.

"Lymphocyte activity" as used herein refers to the immunological processes of B and T cell activation, proliferation, differentiation and survival, as well as associated effector immune functions in lymphocytic cells including cytolytic activity (Tc cells), cytokine production (Th cells), antibody production (B cells), and antigen presentation (B cells). As noted above, there are numerous assays well known to the skilled artisan for detecting and/or monitoring such processes, including but not limited to the assays described in the examples provided herein.

As used herein, the phrase "interaction of zB7R1 and its counter-receptor" or "interaction of zB7R1 and CD155) refers to direct physical interaction (e.g. binding) and/or other indirect interaction of a functional zB7R1 counter-receptor (i.e. CD155) molecule with a functional zB7R1 receptor on a lymphocyte, resulting in stimulation of the zB7R1 receptor and associated intracellular zB7R1 signaling. Similarly, the phrase "natural interaction of zB7R1 and its counter-receptor" refers to direct physical interaction (e.g. binding) and/or other indirect interaction of a functional and endogenously expressed counter-receptor such as CD155, with a functional and endogenously expressed zB7R1 receptor on a lymphocyte, resulting in stimulation of the zB7R1 receptor and associated intracellular zB7R1 signaling.

As used herein, the term "blocking agent" includes those agents that interfere with the interaction of zB7R1 and its counter-receptor, and/or that interfere with the ability of the counter-receptor to inhibit lymphocyte activity, e.g., as measured by cytokine production and/or proliferation. The term "blocking agent" further includes agents that inhibit the ability of zB7R1 to bind a natural ligand, and/or that interfere with the ability of zB7R1 to inhibit T cell activity. Exemplary agents include function-blocking antibodies, as well as peptides that block the binding zB7R1 with its counter-receptor but which fail to stimulate zB7R1-mediated signaling in a lymphocyte (e.g., zB7R1 fusion proteins), peptidomimetics, small molecules, and the like. Preferred blocking agents include agents capable of inhibiting the inducible association of zB7R1 with SHP-1 and/or SHP-2, or the signal transduction that derives from the interaction of SHP-1 and/or SHP-2 with zB7R1.

As used herein, the term "mimicking agent" includes those agents that mimic the interaction of zB7R1 and its counter-receptor, and/or that augment, enhance or increase the ability of zB7R1 and/or its counter-receptor to inhibit lymphocyte activity. Exemplary agents include function-activating antibodies, as well as peptides that augment or enhance the ability of zB7R1 to bind with its counter-receptor or substitute for the counter-receptor's role in stimulating zB7R1-mediated signaling (e.g., Its counter-receptor fusion proteins), peptidomimetics, small molecules, and the like.

The present invention includes functional fragments of zB7R1 genes. Within the context of this invention, a "functional fragment" of a zB7R1 gene refers to a nucleic acid molecule that encodes a portion of a zB7R1 polypeptide which is a domain described herein or at least specifically binds with an anti-zB7R1 antibody.

Due to the imprecision of standard analytical methods, molecular weights and lengths of polymers are understood to be approximate values. When such a value is expressed as "about" X or "approximately" X, the stated value of X will be understood to be accurate to ±10%.

3. Production of zB7R1 Polynucleotides or Genes

Nucleic acid molecules encoding a human zB7R1 gene can be obtained by screening a human cDNA or genomic library using polynucleotide probes based upon SEQ ID NO:1 or 5. These techniques are standard and well-established, and may be accomplished using cloning kits available by commercial suppliers. See, for example, Ausubel et al. (eds.), *Short Protocols in Molecular Biology*, 3$^{rd}$ Edition, John Wiley & Sons 1995; Wu et al., *Methods in Gene Biotechnology*, CRC Press, Inc. 1997; Aviv and Leder, *Proc. Nat'l Acad. Sci. USA* 69:1408 (1972); Huynh et al., "Constructing and Screening cDNA Libraries in λgt10 and λgt11," in *DNA Cloning: A Practical Approach* Vol. I, Glover (ed.), page 49 (IRL Press, 1985); Wu (1997) at pages 47-52.

Nucleic acid molecules that encode a human zB7R1 gene can also be obtained using the polymerase chain reaction (PCR) with oligonucleotide primers having nucleotide sequences that are based upon the nucleotide sequences of the zB7R1 gene or cDNA. General methods for screening libraries with PCR are provided by, for example, Yu et al., "Use of the Polymerase Chain Reaction to Screen Phage Libraries," in *Methods in Molecular Biology*, Vol. 15: *PCR Protocols: Current Methods and Applications*, White (ed.), Humana Press, Inc., 1993. Moreover, techniques for using PCR to isolate related genes are described by, for example, Preston, "Use of Degenerate Oligonucleotide Primers and the Polymerase Chain Reaction to Clone Gene Family Members," in *Methods in Molecular Biology*, Vol. 15: *PCR Protocols: Current Methods and Applications*, White (ed.), Humana Press, Inc. 1993. As an alternative, a zB7R1 gene can be obtained by synthesizing nucleic acid molecules using mutually priming long oligonucleotides and the nucleotide sequences described herein (see, for example, Ausubel (1995)). Established techniques using the polymerase chain reaction provide the ability to synthesize DNA molecules at least two kilobases in length (Adang et al., *Plant Molec. Biol.* 21:1131 (1993), Bambot et al., *PCR Methods and Applications* 2:266 (1993), Dillon et al., "Use of the Polymerase Chain Reaction for the Rapid Construction of Synthetic Genes," in *Methods in Molecular Biology*, Vol. 15: *PCR Protocols: Current Methods and Applications*, White (ed.), pages 263-268, (Humana Press, Inc. 1993), and Holowachuk et al., *PCR Methods Appl.* 4:299 (1995)). For reviews on polynucleotide synthesis, see, for example, Glick and Pasternak, *Molecular Biotechnology, Principles and Applications of Recombinant DNA* (ASM Press 1994), Itakura et al., *Annu. Rev. Biochem.* 53:323 (1984), and Climie et al., *Proc. Nat'l Acad. Sci. USA* 87:633 (1990).

4. Production of zB7R1 and CD155 Polynucleotides and Gene Variants

The present invention provides a variety of nucleic acid molecules, including DNA and RNA molecules, that encode the zB7R1 polypeptides disclosed herein. Those skilled in the art will readily recognize that, in view of the degeneracy of the genetic code, considerable sequence variation is possible among these polynucleotide molecules. Moreover, the present invention also provides isolated soluble monomeric, homodimeric, heterodimeric and multimeric receptor polypeptides that comprise at least one zB7R1 receptor subunit that is substantially homologous to the receptor polypeptide of SEQ ID NO:2 or 5. Thus, the present invention contemplates zB7R1 polypeptide-encoding nucleic acid molecules comprising degenerate nucleotides of SEQ ID NO:1, and their RNA equivalents.

Table 1 sets forth the one-letter codes to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding an amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequences of SEQ ID NO:2. Variant sequences can be readily tested for functionality as described herein.

Different species can exhibit "preferential codon usage." In general, see, Grantham et al., *Nucl. Acids Res.* 8:1893 (1980), Haas et al. *Curr. Biol.* 6:315 (1996), Wain-Hobson et al., *Gene* 13:355 (1981), Grosjean and Fiers, *Gene* 18:199 (1982), Holm, *Nuc. Acids Res.* 14:3075 (1986), Ikemura, *J. Mol. Biol.* 158:573 (1982), Sharp and Matassi, *Curr. Opin. Genet. Dev.* 4:851 (1994), Kane, *Curr. Opin. Biotechnol.* 6:494 (1995), and Makrides, *Microbiol. Rev.* 60:512 (1996). As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequences disclosed herein serve as a template for optimizing expression of polynucleotides in various cell types and species commonly used in the art and disclosed herein. Sequences containing preferential codons can be tested and optimized for expression in various species, and tested for functionality as disclosed herein.

A zB7R1-encoding cDNA can be isolated by a variety of methods, such as by probing with a complete or partial human cDNA or with one or more sets of degenerate probes based on the disclosed sequences. A cDNA can also be cloned using the polymerase chain reaction with primers designed from the representative human zB7R1 sequences disclosed herein. In addition, a cDNA library can be used to transform or transfect host cells, and expression of the cDNA of interest can be detected with an antibody to zB7R1 polypeptide.

Those skilled in the art will recognize that the sequence disclosed in SEQ ID NO:1 represents a single allele of human zB7R1, and that allelic variation and alternative splicing are expected to occur (i.e. SEQ ID NO:5). Allelic variants of this sequence can be cloned by probing cDNA or genomic libraries from different individuals according to standard procedures. Allelic variants of the nucleotide sequences disclosed herein, including those containing silent mutations and those in which mutations result in amino acid sequence changes, are within the scope of the present invention, as are proteins which are allelic variants of the amino acid sequences disclosed herein. cDNA molecules generated from alternatively spliced mRNAs, which retain the properties of the zB7R1 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

Using the methods discussed above, one of ordinary skill in the art can prepare a variety of polypeptides that comprise a soluble zB7R1 receptor that is substantially homologous to SEQ ID NO:2 or 5, or that encodes amino acids of SEQ ID NO:3, 4 or 6, or allelic variants thereof and retain the counter-receptor-binding properties of the wild-type zB7R1 receptor. Such polypeptides may also include additional polypeptide segments as generally disclosed herein.

Within certain embodiments of the invention, the isolated nucleic acid molecules can hybridize under stringent conditions to nucleic acid molecules comprising nucleotide sequences disclosed herein. For example, such nucleic acid molecules can hybridize under stringent conditions to nucleic acid molecules comprising the nucleotide sequence of SEQ ID NO:1, or to nucleic acid molecules comprising a nucleotide sequence complementary to SEQ ID NO:1, or fragments thereof.

In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Following hybridization, the nucleic acid molecules can be washed to remove non-hybridized nucleic acid molecules under stringent conditions, or under highly stringent conditions. See, for example, Sambrook et al., *Molecular Cloning: A Laboratory Manual*, Second Edition (Cold Spring Harbor Press 1989); Ausubel et al., (eds.), *Current Protocols in Molecular Biology* (*John* Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and *Primer Premier* 4.0 (Premier Biosoft International; Palo Alto, Calif.), as well as sites on the Internet, are available tools for analyzing a given sequence and calculating $T_m$ based on user-defined criteria. It is well within the abilities of one skilled in the art to adapt hybridization and wash conditions for use with a particular polynucleotide hybrid.

The present invention also provides isolated zB7R1 polypeptides that have a substantially similar sequence identity to the polypeptides of SEQ ID NO:2, 3, 6 or 7, or their orthologs. The term "substantially similar sequence identity" is used herein to denote polypeptides having at least 70%, at least 80%, at least 90%, at least 95%, such as 96%, 97%, 98%, or greater than 95% sequence identity to the sequences shown in SEQ ID NO:3, or their orthologs. For example, variant and orthologous zB7R1 receptors can be used to generate an immune response and raise cross-reactive antibodies to human zB7R1. Such antibodies can be humanized, and modified as described herein, and used therapeutically to treat psoriasis, psoriatic arthritis, IBD, colitis, endotoxemia as well as in other therapeutic applications described herein.

The present invention also contemplates zB7R1 variant nucleic acid molecules that can be identified using two criteria: a determination of the similarity between the encoded polypeptide with the amino acid sequence of SEQ ID NO:2, and a hybridization assay. Such zB7R1 variants include nucleic acid molecules (1) that remain hybridized with a nucleic acid molecule having the nucleotide sequence of SEQ ID NO:1 (or its complement) under stringent washing conditions, in which the wash stringency is equivalent to 0.5×-2×SSC with 0.1% SDS at 55-65° C., and (2) that encode a polypeptide having at least 70%, at least 80%, at least 90%, at least 95%, or greater than 95% such as 96%, 97%, 98%, or 99%, sequence identity to the amino acid sequence of SEQ ID NO:3. Alternatively, zB7R1 variants can be characterized as nucleic acid molecules (1) that remain hybridized with a nucleic acid molecule having the nucleotide sequence of SEQ ID NO:1 (or its complement) under highly stringent washing conditions, in which the wash stringency is equivalent to 0.1×-0.2×SSC with 0.1% SDS at 50-65° C., and (2) that encode a polypeptide having at least 70%, at least 80%, at least 90%, at least 95% or greater than 95%, such as 96%, 97%, 98%, or 99% or greater, sequence identity to the amino acid sequence of SEQ ID NO:2.

Percent sequence identity is determined by conventional methods. See, for example, Altschul et al., Bull. Math. Bio. 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 3 (amino acids are indicated by the standard one-letter codes). The percent identity is then calculated as: ([Total number of identical matches]/[length of the longer sequence plus the number of gaps introduced into the longer sequence in order to align the two sequences])(100).

can range between one to six, preferably from three to six, most preferably three, with other parameters set as described above.

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative zB7R1 variant. The FASTA algorithm is described by Pearson and Lipman, Proc. Nat'l Acad. Sci. USA 85:2444 (1988), and by Pearson, Meth. Enzymol. 183:63 (1990). Briefly, FASTA first characterizes sequence similarity by identifying regions shared by the query sequence (e.g., SEQ ID NO:2 or SEQ ID NO:3) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, J. Mol. Biol. 48:444 (1970); Sellers, SIAM J. Appl. Math. 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, Meth. Enzymol. 183:63 (1990).

FASTA can also be used to determine the sequence identity of nucleic acid molecules using a ratio as disclosed above. For nucleotide sequence comparisons, the ktup value The present invention includes nucleic acid molecules that encode a polypeptide having a conservative amino acid change, compared with an amino acid sequence disclosed herein. For example, variants can be obtained that contain one or more amino acid substitutions of SEQ ID NO:2, in which an alkyl amino acid is substituted for an alkyl amino acid in a zB7R1 amino acid sequence, an aromatic amino acid is substituted for an aromatic amino acid in a zB7R1 amino acid sequence, a sulfur-containing amino acid is substituted for a sulfur-containing amino acid in a zB7R1 amino acid sequence, a hydroxy-containing amino acid is substituted for a hydroxy-containing amino acid in a zB7R1 amino acid sequence, an acidic amino acid is substituted for an acidic amino acid in a zB7R1 amino acid sequence, a basic amino acid is substituted for a basic amino acid in a zB7R1 amino acid sequence, or a dibasic monocarboxylic amino acid is substituted for a dibasic monocarboxylic amino acid in a zB7R1 amino acid sequence. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff and Henikoff, Proc. Nat'l Acad. Sci. USA 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3). Particular variants of zB7R1 are characterized by having at least 70%, at least 80%, at least 90%, at least 95% or greater than 95% such as 96%, 97%, 98%, or 99% or greater sequence identity to the corresponding amino acid sequence (e.g., SEQ ID NO:2, 3, 6 or 7), wherein the variation in amino acid sequence is due to one or more conservative amino acid substitutions.

Conservative amino acid changes in a zB7R1 gene can be introduced, for example, by substituting nucleotides for the nucleotides recited in SEQ ID NO:1 or 5. Such "conservative amino acid" variants can be obtained by oligonucleotide-directed mutagenesis, linker-scanning mutagenesis, mutagenesis using the polymerase chain reaction, and the like (see Ausubel (1995); and McPherson (ed.), *Directed Mutagenesis: A Practical Approach* (IRL Press 1991)). A variant zB7R1 polypeptide can be identified by the ability to specifically bind anti-zB7R1 antibodies.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., *J. Am. Chem. Soc.* 113:2722 (1991), Ellman et al., *Methods Enzymol.* 202:301 (1991), Chung et al., *Science* 259:806 (1993), and Chung et al., *Proc. Nat'l Acad. Sci. USA* 90:10145 (1993).

In a second method, translation is carried out in *Xenopus* oocytes by microinjection of mutated mRNA and chemically aminoacylated suppressor tRNAs (Turcatti et al., *J. Biol. Chem.* 271:19991 (1996)). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395 (1993)).

A limited number of non-conservative amino acids, amino acids that are not encoded by the genetic code, non-naturally occurring amino acids, and unnatural amino acids may be substituted for zB7R1 amino acid residues.

Essential amino acids in the polypeptides of the present invention can be identified according to procedures known in the art, such as site-directed mutagenesis or alanine-scanning mutagenesis (Cunningham and Wells, *Science* 244:1081 (1989), Bass et al., *Proc. Nat'l Acad. Sci. USA* 88:4498 (1991), Coombs and Corey, "Site-Directed Mutagenesis and Protein Engineering," in *Proteins: Analysis and Design*, Angeletti (ed.), pages 259-311 (Academic Press, Inc. 1998)). In the latter technique, single alanine mutations are introduced at every residue in the molecule, and the resultant mutant molecules are tested for biological activity to identify amino acid residues that are critical to the activity of the molecule. See also, Hilton et al., *J. Biol. Chem.* 271:4699 (1996).

Although sequence analysis can be used to further define the zB7R1 counter-receptor binding region, amino acids that play a role in zB7R1 binding activity (such as binding of zB7R1 to its counter-receptor or counter-receptors, or to an anti-zB7R1 antibody) can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306 (1992), Smith et al., *J. Mol. Biol.* 224:899 (1992), and Wlodaver et al., *FEBS Lett.* 309:59 (1992).

Multiple amino acid substitutions can be made and tested using known methods of mutagenesis and screening, such as those disclosed by Reidhaar-Olson and Sauer (*Science* 241:53 (1988)) or Bowie and Sauer (*Proc. Nat'l Acad. Sci. USA* 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832 (1991), Ladner et al., U.S. Pat. No. 5,223,409, Huse, international publication No. WO 92/06204, and region-directed mutagenesis (Derbyshire et al., *Gene* 46:145 (1986), and Ner et al., *DNA* 7:127, (1988)). Moreover, zB7R1 labeled with biotin or FITC can be used for expression cloning of zB7R1 counter-receptors.

Variants of the disclosed zB7R1 nucleotide and polypeptide sequences can also be generated through DNA shuffling as disclosed by Stemmer, *Nature* 370:389 (1994), Stemmer, *Proc. Nat'l Acad. Sci. USA* 91:10747 (1994), and international publication No. WO 97/20078. Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-zB7R1 antibodies, can be recovered from the host cells and rapidly sequenced using modern equipment. These methods allow the rapid determination of the importance of individual amino acid residues in a polypeptide of interest, and can be applied to polypeptides of unknown structure.

The present invention also includes "functional fragments" of zB7R1 polypeptides and nucleic acid molecules encoding such functional fragments. Routine deletion analyses of nucleic acid molecules can be performed to obtain functional fragments of a nucleic acid molecule that encodes a zB7R1 polypeptide. As an illustration, DNA molecules having the nucleotide sequence of SEQ ID NO:1 or 5 can be digested with Bal31 nuclease to obtain a series of nested deletions. The fragments are then inserted into expression vectors in proper reading frame, and the expressed polypeptides are isolated and tested for the ability to bind anti-zB7R1 antibodies. One alternative to exonuclease digestion is to use oligonucleotide-directed mutagenesis to introduce deletions or stop codons to specify production of a desired fragment. Alternatively, particular fragments of a zB7R1 gene can be synthesized using the polymerase chain reaction.

This general approach is exemplified by studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 *kDa* 2-5A synthetase induced by human interferon," in *Biological Interferon Systems, Proceedings of ISIR-TNO Meeting on Interferon Systems*, Cantell (ed.), pages 65-72 (Nijhoff 1987), Herschman, "The EGF Receptor," in *Control of Animal Cell Proliferation*, Vol. 1, Boynton et al., (eds.) pages 169-199 (Academic Press 1985), Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995), and Meisel et al., *Plant Molec. Biol.* 30:1 (1996).

The present invention also contemplates functional fragments of a zB7R1 gene that have amino acid changes, compared with an amino acid sequence disclosed herein. A variant zB7R1 gene can be identified on the basis of structure by determining the level of identity with disclosed nucleotide and amino acid sequences, as discussed above. An alternative approach to identifying a variant gene on the basis of structure is to determine whether a nucleic acid molecule encoding a potential variant zB7R1 gene can hybridize to a nucleic acid molecule comprising a nucleotide sequence, such as SEQ ID NO:1 or 5.

The present invention also includes using functional fragments of zB7R1 polypeptides, antigenic epitopes, epitope-bearing portions of zB7R1 polypeptides, and nucleic acid molecules that encode such functional fragments, antigenic epitopes, epitope-bearing portions of zB7R1 polypeptides. Such fragments are used to generate polypeptides for use in generating antibodies and binding partners that agonize, bind, block, inhibit, increase, reduce, antagonize or neutralize activity of a B7 receptor. A "functional" zB7R1 polypeptide or fragment thereof as defined herein is characterized by its ability to bind a zB7R1 counter-receptor such as CD155, or block, inhibit, reduce, antagonize or neutralize zB7R1-mediated signaling or inflammatory, proliferative or differentiating activity; or by its ability to induce or inhibit specialized cell functions; or by its ability to bind specifically to an anti-zB7R1 antibody, cell, or B7 counter-receptor. As previously described herein, zB7R1 is characterized as a B7 family member by its receptor structure and domains as described herein. Thus, the present invention further contemplates using fusion proteins encompassing: (a) polypeptide molecules comprising one or more of the domains described above; and (b) functional fragments comprising one or more of these domains. The other polypeptide portion of the fusion protein may be contributed by another B7 family receptor, such as CD28, CTLA-4, ICOS, PD-1, HHLA2, or BTLA, or by a non-native and/or an unrelated secretory signal peptide that facilitates secretion of the fusion protein.

The present invention also provides polypeptide fragments or peptides comprising an epitope-bearing portion of a zB7R1 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219: 660 (1983)). Accordingly, antigenic epitope-bearing peptides, antigenic peptides, epitopes, and polypeptides of the present invention are useful to raise antibodies that bind with the polypeptides described herein, as well as to identify and screen anti-zB7R1 monoclonal antibodies that are neutralizing, and that may agonize, bind, block, inhibit, reduce, antagonize or neutralize the activity of its counter-receptor. Such neutralizing monoclonal antibodies of the present invention can bind to a zB7R1 antigenic epitope. Hopp/Woods hydrophilicity profiles can be used to determine regions that have the most antigenic potential within SEQ ID NO:3 (Hopp et al., *Proc. Natl. Acad. Sci.* 78:3824-3828, 1981; Hopp, *J. Immun. Meth.* 88:1-18, 1986 and Triquier et al., *Protein Engineering* 11:153-169, 1998). The profile is based on a sliding six-residue window. Buried G, S, and T residues and exposed H, Y, and W residues were ignored. In zB7R1 these regions can be determined by one of skill in the art. Moreover, zB7R1 antigenic epitopes within SEQ ID NO:2 as predicted by a Jameson-Wolf plot, e.g., using DNASTAR Protean program (DNASTAR, Inc., Madison, Wis.) serve as preferred antigenic epitopes, and can be determined by one of skill in the art. Such antigenic epitopes include (1) amino acid residues 80 to 86 of SEQ ID NO:2; (2) amino acid residues 163 to 170 of SEQ ID NO:2; (3) amino acid residues 163 to 190 of SEQ ID NO:2; (4) amino acid residues 175 to 190 of SEQ ID NO:2; and (5) amino acid residues 211 to 221 of SEQ ID NO:2. In preferred embodiments, antigenic epitopes to which neutralizing antibodies of the present invention bind would contain residues of SEQ ID NO:2 (and corresponding residues of SEQ ID NO:3) that are important to counter-receptor-receptor binding.

Antigenic epitope-bearing peptides and polypeptides can contain at least four to ten amino acids, at least ten to fifteen amino acids, or about 15 to about 30 amino acids of an amino acid sequence disclosed herein. Such epitope-bearing peptides and polypeptides can be produced by fragmenting a zB7R1 polypeptide, or by chemical peptide synthesis, as described herein. Moreover, epitopes can be selected by phage display of random peptide libraries (see, for example, Lane and Stephen, *Curr. Opin. Immunol.* 5:268 (1993), and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology*, Vol. 10, Manson (ed.), pages 105-116 (The Humana Press, Inc. 1992), Price, "Production and Characterization of Synthetic Peptide-Derived Antibodies," in *Monoclonal Antibodies: Production, Engineering, and Clinical Application*, Ritter and Ladyman (eds.), pages 60-84 (Cambridge University Press 1995), and Coligan et al. (eds.), *Current Protocols in Immunology, pages* 9.3.1-9.3.5 and pages 9.4.1-9.4.11 (John Wiley & Sons 1997).

For any zB7R1 polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise zB7R1 variants based upon the nucleotide and amino acid sequences described herein.

5. Production of zB7R1 and CD155 Polypeptides

The polypeptides of the present invention, including full-length polypeptides; soluble monomeric, homodimeric, heterodimeric and multimeric receptors; full-length receptors; receptor fragments (e.g. counter-receptor-binding fragments and antigenic epitopes), functional fragments, and fusion proteins, can be produced in recombinant host cells following conventional techniques. To express a zB7R1 or CD155 gene, a nucleic acid molecule encoding the polypeptide must be operably linked to regulatory sequences that control transcriptional expression in an expression vector and then, introduced into a host cell. In addition to transcriptional regulatory sequences, such as promoters and enhancers, expression vectors can include translational regulatory sequences and a marker gene which is suitable for selection of cells that carry the expression vector.

Expression vectors that are suitable for production of a foreign protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. As discussed above, expression vectors can also include nucleotide sequences encoding a secretory sequence that directs the heterologous polypeptide into the secretory pathway of a host cell. For example, a zB7R1 expression vector may comprise a zB7R1 gene and a secretory sequence derived from any secreted gene.

zB7R1 or CD155 proteins of the present invention may be expressed in mammalian cells. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 (Chasin et al., *Som. Cell. Molec. Genet.* 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

For a mammalian host, the transcriptional and translational regulatory signals may be derived from mammalian viral sources, for example, adenovirus, bovine papilloma virus, simian virus, or the like, in which the regulatory signals are associated with a particular gene which has a high level of expression. Suitable transcriptional and translational regulatory sequences also can be obtained from mammalian genes, for example, actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1:273 (1982)), the TK promoter of Herpes virus (McKnight, *Cell* 31:355 (1982)), the SV40 early promoter (Benoist et al., *Nature* 290:304 (1981)), the Rous sarcoma virus promoter (Gorman et al., *Proc. Nat'l Acad. Sci. USA* 79:6777 (1982)), the cytomegalovirus promoter (Foecking et al., *Gene* 45:101 (1980)), and the mouse mammary tumor virus promoter (see, generally, Etcheverry, "Expression of Engineered Proteins in Mammalian Cell Culture," in *Protein Engineering: Principles and Practice*, Cleland et al. (eds.), pages 163-181 (John Wiley & Sons, Inc. 1996)).

Alternatively, a prokaryotic promoter, such as the bacteriophage T3 RNA polymerase promoter, can be used to control zB7R1 gene expression in mammalian cells if the prokaryotic promoter is regulated by a eukaryotic promoter (Zhou et al., *Mol. Cell. Biol.* 10:4529 (1990), and Kaufman et al., *Nucl. Acids Res.* 19:4485 (1991)).

In certain embodiments, a DNA sequence encoding a zB7R1 soluble receptor polypeptide, a fragment of zB7R1 polypeptide, a CD155 soluble receptor or a fragment of a CD155 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers. Multiple components of a soluble receptor complex can be co-transfected on individual expression vectors or be contained in a single expression vector. Such techniques of expressing multiple components of protein complexes are well known in the art.

An expression vector can be introduced into host cells using a variety of standard techniques including calcium phosphate transfection, liposome-mediated transfection, microprojectile-mediated delivery, electroporation, and the like. The transfected cells can be selected and propagated to provide recombinant host cells that comprise the expression vector stably integrated in the host cell genome. Techniques for introducing vectors into eukaryotic cells and techniques for selecting such stable transformants using a dominant selectable marker are described, for example, by Ausubel (1995) and by Murray (ed.), *Gene Transfer and Expression Protocols* (Humana Press 1991).

For example, one suitable selectable marker is a gene that provides resistance to the antibiotic neomycin. In this case, selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A suitable amplifiable selectable marker is dihydrofolate reductase (DHFR), which confers resistance to methotrexate. Other drug resistance genes (e.g., hygromycin resistance, multi-drug resistance, puromycin acetyltransferase) can also be used. Alternatively, markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

zB7R1 polypeptides can also be produced by cultured mammalian cells using a viral delivery system. Exemplary viruses for this purpose include adenovirus, retroviruses, herpesvirus, vaccinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161 (1994), and Douglas and Curiel, *Science & Medicine* 4:44 (1997)). Advantages of the adenovirus system include the accommodation of relatively large DNA inserts, the ability to grow to high-titer, the ability to infect a broad range of mammalian cell types, and flexibility that allows use with a large number of available vectors containing different promoters.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. An option is to delete the essential E1 gene from the viral vector, which results in the inability to replicate unless the E1 gene is provided by the host cell. Adenovirus vector-infected human 293 cells (ATCC Nos. CRL-1573, 45504, 45505), for example, can be grown as adherent cells or in suspension culture at relatively high cell density to produce significant amounts of protein (see Garnier et al., *Cytotechnol.* 15:145 (1994)).

zB7R1 or CD155 can also be expressed in other higher eukaryotic cells, such as avian, fungal, insect, yeast, or plant cells. The baculovirus system provides an efficient means to introduce cloned zB7R1 genes into insect cells. Suitable expression vectors are based upon the *Autographa californica* multiple nuclear polyhedrosis virus (AcMNPV), and contain well-known promoters such as *Drosophila* heat shock protein (hsp) 70 promoter, *Autographa californica* nuclear polyhedrosis virus immediate-early gene promoter (ie-1) and the delayed early 39K promoter, baculovirus p10 promoter, and the *Drosophila metallothionein* promoter. A second method of making recombinant baculovirus utilizes a transposon-based system described by Luckow (Luckow, et al., *J. Virol.* 67:4566 (1993)). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the DNA encoding the zB7R1 polypeptide into a baculovirus genome maintained in *E. coli* as a large plasmid called a "bacmid." See, Hill-Perkins and Possee, *J. Gen. Virol.* 71:971 (1990), Bonning, et al., *J. Gen. Virol.* 75:1551 (1994), and Chazenbalk, and Rapoport, *J. Biol. Chem.* 270:1543 (1995). In addition, transfer vectors can include an in-frame fusion with DNA encoding an epitope tag at the C- or N-terminus of the expressed zB7R1 polypeptide, for example, a Glu-Glu epitope tag (Grussenmeyer et al., *Proc. Nat'l Acad. Sci.* 82:7952 (1985)). Using a technique known in the art, a transfer vector containing a zB7R1 gene is transformed into *E. coli*, and screened for bacmids which contain an interrupted lacZ gene indicative of recombinant baculovirus. The bacmid DNA containing the recombinant baculovirus genome is then isolated using common techniques.

The illustrative PFASTBAC vector can be modified to a considerable degree. For example, the polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins (see, for example, Hill-Perkins and Possee, *J. Gen. Virol.* 71:971 (1990), Bonning, et al., *J. Gen. Virol.* 75:1551 (1994), and Chazenbalk and Rapoport, *J. Biol. Chem.* 270:1543 (1995). In such transfer vector constructs, a short or long version of the basic protein promoter can be used. Moreover, transfer vectors can be constructed which replace the native zB7R1 secretory signal sequences with secretory signal sequences derived from insect proteins. For example, a secretory signal sequence from Ecdysteroid Glucosyltransferase (EGT), honey bee Melittin (Invitrogen Corporation; Carlsbad, Calif.), or baculovirus gp67 (PharMingen: San Diego, Calif.) can be used in constructs to replace the native zB7R1 secretory signal sequence.

The recombinant virus or bacmid is used to transfect host cells. Suitable insect host cells include cell lines derived from IPLB-Sf-21, a *Spodoptera frupperda* pupal ovarian cell line, such as Sf9 (ATCC CRL 1711), Sf21AE, and Sf21 (Invitrogen Corporation; San Diego, Calif.), as well as *Drosophila* Schneider-2 cells, and the HIGH FIVEO cell line (Invitrogen) derived from *Trichoplusia ni* (U.S. Pat. No. 5,300,435). Commercially available serum-free media can be used to grow and to maintain the cells. Suitable media are S1900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T ni* cells. When recombinant virus is used, the cells are typically grown up from an inoculation density of approximately $2-5 \times 10^5$ cells to a density of $1-2 \times 10^6$ cells at which time a recombinant viral stock is added at a multiplicity of infection (MOI) of 0.1 to 10, more typically near 3.

Established techniques for producing recombinant proteins in baculovirus systems are provided by Bailey et al., "Manipulation of Baculovirus Vectors," in *Methods in Molecular Biology*, Volume 7: *Gene Transfer and Expression Protocols*, Murray (ed.), pages 147-168 (The Humana Press, Inc. 1991), by Patel et al., "The baculovirus expression system," in *DNA Cloning 2: Expression Systems,* 2nd Edition, Glover et al. (eds.), pages 205-244 (Oxford University Press 1995), by Ausubel (1995) at pages 16-37 to 16-57, by Richardson (ed.), *Baculovirus Expression Protocols* (The Humana Press, Inc. 1995), and by Lucknow, "Insect Cell Expression Technology," in *Protein Engineering: Principles and Practice*, Cleland et al. (eds.), pages 183-218 (John Wiley & Sons, Inc. 1996).

Fungal cells, including yeast cells, can also be used to express the genes described herein. Yeast species of particular interest in this regard include *Saccharomyces cerevisiae, Pichia pastoris,* and *Pichia methanolica*. Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include YIp-based vectors, such as YIp5, YRp vectors, such as YRp17, YEp vectors such as YEp13 and YCp vectors, such as YCp19. Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat. No. 4,931,373, Brake, U.S. Pat. No. 4,870,008, Welch et al., U.S. Pat. No. 5,037,743, and Murray et al., U.S. Pat. No. 4,845,075. Transformed cells are selected by phenotype determined by the selectable marker, commonly drug resistance or the ability to grow in the absence of a particular nutrient (e.g., leucine). A suitable vector system for use in *Saccharomyces cerevisiae* is the POT1 vector system disclosed by Kawasaki et al. (U.S. Pat. No. 4,931,373), which allows transformed cells to be selected by growth in glucose-containing media. Additional suitable promoters and terminators for use in yeast include those from glycolytic enzyme genes (see, e.g., Kawasaki, U.S. Pat. No. 4,599,311, Kingsman et al., U.S. Pat. No. 4,615,974, and Bitter, U.S. Pat. No. 4,977,092) and alcohol dehydrogenase genes. See also U.S. Pat. Nos. 4,990,446, 5,063,154, 5,139,936, and 4,661,454.

Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459 (1986), and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., *Yeast* 14:11-23 (1998), and in international publication Nos. WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, the promoter and terminator in the plasmid can be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A suitable selectable marker for use in *Pichia methanolica* is a *P. methanolica* ADE2 gene, which encodes phosphoribosyl-5-aminoimidazole carboxylase (AIRC; EC 4.1.1.21), and which allows ade2 host cells to grow in the absence of adenine. For large-scale, industrial processes where it is desirable to minimize the use of methanol, host cells can be used in which both methanol utilization genes (AUG1 and AUG2) are deleted. For production of secreted proteins, host cells can be deficient in vacuolar protease genes (PEP4 and PRB1). Electroporation is used to facilitate the introduction of a plasmid containing DNA encoding a polypeptide of interest into *P. methanolica* cells. *P. methanolica* cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Expression vectors can also be introduced into plant protoplasts, intact plant tissues, or isolated plant cells. Methods for introducing expression vectors into plant tissue include the direct infection or co-cultivation of plant tissue with *Agrobacterium tumefaciens*, microprojectile-mediated delivery, DNA injection, electroporation, and the like. See, for example, Horsch et al., *Science* 227:1229 (1985), Klein et al., *Biotechnology* 10:268 (1992), and Mild et al., "Procedures for Introducing Foreign DNA into Plants," in *Methods in Plant Molecular Biology and Biotechnology*, Glick et al. (eds.), pages 67-88 (CRC Press, 1993).

Alternatively, zB7R1 genes can be expressed in prokaryotic host cells. Suitable promoters that can be used to express zB7R1 polypeptides in a prokaryotic host are well-known to those of skill in the art and include promoters capable of recognizing the T4, T3, Sp6 and T7 polymerases, the PR and PL promoters of bacteriophage lambda, the trp, recA, heat shock, lacUV5, tac, lpp-lacSpr, phoA, and lacZ promoters of *E. coli*, promoters of *B. subtilis*, the promoters of the bacteriophages of *Bacillus, Streptomyces* promoters, the int promoter of bacteriophage lambda, the bla promoter of pBR322, and the CAT promoter of the chloramphenicol acetyl transferase gene. Prokaryotic promoters have been reviewed by Glick, *J. Ind. Microbiol.* 1:277 (1987), Watson et al., *Molecular Biology of the Gene*, 4th Ed. (Benjamin Cummins 1987), and by Ausubel et al. (1995).

Suitable prokaryotic hosts include *E. coli* and *Bacillus subtilus*. Suitable strains of *E. coli* include BL21(DE3), BL21(DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), *Molecular Biology Labfax* (Academic Press 1991)). Suitable strains of *Bacillus subtilus* include BR151, YB886, MI119, MI120, and B170 (see, for example, Hardy, "*Bacillus* Cloning Methods," in *DNA Cloning: A Practical Approach*, Glover (ed.) (IRL Press 1985)).

When expressing a zB7R1 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Methods for expressing proteins in prokaryotic hosts are well-known to those of skill in the art (see, for example, Williams et al., "Expression of foreign proteins in *E. coli* using plasmid vectors and purification of specific polyclonal antibodies," in *DNA Cloning 2: Expression Systems*, 2nd Edition, Glover et al. (eds.), page 15 (Oxford University Press 1995), Ward et al., "Genetic Manipulation and Expression of Antibodies," in *Monoclonal Antibodies: Principles and Applications*, page 137 (Wiley-Liss, Inc. 1995), and Georgiou, "Expression of Proteins in Bacteria," in *Protein Engineering: Principles and Practice*, Cleland et al. (eds.), page 101 (John Wiley & Sons, Inc. 1996)).

Standard methods for introducing expression vectors into bacterial, yeast, insect, and plant cells are provided, for example, by Ausubel (1995).

General methods for expressing and recovering foreign protein produced by a mammalian cell system are provided by, for example, Etcheverry, "Expression of Engineered Proteins in Mammalian Cell Culture," in *Protein Engineering: Principles and Practice*, Cleland et al. (eds.), pages 163 (Wiley-Liss, Inc. 1996). Standard techniques for recovering protein produced by a bacterial system is provided by, for example, Grisshammer et al., "Purification of over-produced proteins from *E. coli* cells," in *DNA Cloning 2: Expression Systems*, 2nd Edition, Glover et al. (eds.), pages 59-92 (Oxford University Press 1995). Established methods for isolating recombinant proteins from a baculovirus system are described by Richardson (ed.), *Baculovirus Expression Protocols* (The Humana Press, Inc. 1995).

As an alternative, polypeptides of the present invention can be synthesized by exclusive solid phase synthesis, partial solid phase methods, fragment condensation or classical solution synthesis. These synthesis methods are well-known to those of skill in the art (see, for example, Merrifield, *J. Am. Chem. Soc.* 85:2149 (1963), Stewart et al., "Solid Phase Peptide Synthesis" (2nd Edition), (Pierce Chemical Co. 1984), Bayer and Rapp, *Chem. Pept. Prot.* 3:3 (1986), Atherton et al., *Solid Phase Peptide Synthesis: A Practical Approach* (IRL Press 1989), Fields and Colowick, "Solid-Phase Peptide Synthesis," *Methods in Enzymology* Volume 289 (Academic Press 1997), and Lloyd-Williams et al., *Chemical Approaches to the Synthesis of Peptides and Proteins* (CRC Press, Inc. 1997)). Variations in total chemical synthesis strategies, such as "native chemical ligation" and "expressed protein ligation" are also standard (see, for example, Dawson et al., *Science* 266:776 (1994), Hackeng et al., *Proc. Nat'l Acad. Sci. USA* 94:7845 (1997), Dawson, *Methods Enzymol.* 287: 34 (1997), Muir et al, *Proc. Nat'l Acad. Sci. USA* 95:6705 (1998), and Severinov and Muir, *J. Biol. Chem.* 273:16205 (1998)).

Peptides and polypeptides of the present invention comprise at least six, at least nine, or at least 15 contiguous amino acid residues of SEQ ID NO:2. As an illustration, polypeptides can comprise at least six, at least nine, or at least 15 contiguous amino acid residues of SEQ ID NO:2. Within certain embodiments of the invention, the polypeptides comprise 20, 30, 40, 50, 100, or more contiguous residues of these amino acid sequences. Nucleic acid molecules encoding such peptides and polypeptides are useful as polymerase chain reaction primers and probes.

Moreover, zB7R1 or CD155 polypeptides and fragments thereof can be expressed as monomers, homodimers, heterodimers, tetramers (discussed below) or multimers within higher eukaryotic cells. Such cells can be used to produce zB7R1 or CD15 monomeric, homodimeric, heterodimeric, tetrameric and multimeric receptor polypeptides that comprise at least one zB7R1 or CD155 polypeptide ("zB7R1-comprising receptors," "zB7R1-comprising receptor polypeptides," "CD155-comprising receptors" or "CD155-comprising receptor polypeptides"), or can be used as assay cells in screening systems. Within one aspect of the present invention, a polypeptide of the present invention comprising the zB7R1 extracellular domain (SEQ ID NO:3 or 7) is produced by a cultured cell, and the cell is used to screen for counter-receptors for the receptor, including a natural counter-receptor, as well as agonists and antagonists of the natural counter-receptor. To summarize this approach, a cDNA or gene encoding the receptor is combined with other genetic elements required for its expression (e.g., a transcription promoter), and the resulting expression vector is inserted into a host cell. Cells that express the DNA and produce functional receptor are selected and used within a variety of screening systems. Each component of the monomeric, homodimeric, heterodimeric and multimeric receptor complex can be expressed in the same cell. Moreover, the components of the monomeric, homodimeric, heterodimeric and multimeric receptor complex can also be fused to a transmembrane domain or other membrane fusion moiety to allow complex assembly and screening of transfectants as described above.

6. zB7R1 and CD155 Tetrameric Polynucleotides, Polypeptides and Methods of Making the Same The present invention also encompasses methods of producing a multimeric, preferably tetrameric, zB7R1 or CD155 polypeptides. These proteins are described in more detail in U.S. Provisional Patent Application No. 60/60/791,626, filed Apr. 13, 2006, and incorporated herein in its entirety. These fusion proteins comprise a VASP domain and a herterologous protein domain, such as zB7R1 or CD155. VASP domains are derived from the VASP gene present in many species. Sequences are selected for their anticipated ability to form coiled-coil protein structure, as this structure is important for the ability to form multimeric protein forms. Particularly desired for the present invention is the ability of coiled-coil proteins to produce tetrameric protein structures. A particularly preferred embodiment utilizes amino acids 343 to 376 of the human VASP sequence (amino acids 5 to 38 of SEQ ID NO:23). The full length DNA sequence of this protein is SEQ ID NO: 24 and the full length polypeptide sequence of this protein is SEQ ID NO:25.

Work with other types of multimerizing sequences, for examples, the leucine zipper, has shown that a limited number of conservative amino acid substitutions (even at the d residue) can be often be tolerated in zipper sequences without the loss of the ability of the molecules to multimerize (Landschultz et al., (1989), supra). Thus, conservative changes from the native sequence for the VASP domain are contemplated within the scope of the invention. Table 4 shows the conservative changes that are anticipated to tolerated by the coiled-coil structure.

TABLE 4

| Conservative amino acid substitutions | | | |
|---|---|---|---|
| Basic: | arginine | Aromatic: | phenylalanine |
| | lysine | | tryptophan |
| | histidine | | tyrosine |
| Acidic: | glutamic acid | Small: | glycine |
| | aspartic acid | | alanine |
| Polar: | glutamine | | serine |
| | asparagine | | threonine |
| Hydrophobic: | leucine | | methionine |
| | isoleucine | | |
| | valine | | |
| | methionine | | |

If more than one fusion protein is being used to produce hetero-multimeric proteins, for example, heterotetramers, the VASP domain that is used can be the same domain for both fusion proteins or different VASP domains, as long as the domains have the ability to associate with each other and form multimeric proteins.

The VASP domain can be put at either the N or C terminus of the heterologous protein of interest, based on considerations of function (i.e., whether the heterologous protein is a type I or type II membrane protein) and ease of construction of the construct. Additionally, the VASP domain can be located in the middle of the protein, effectively creating a double fusion protein with one heterologous sequence, a VASP domain, and a second heterologous sequence. The two heterologous sequences for the double fusion protein can be the same or different.

Specifically, zB7R1 or CD155 may be linked directly to another protein to form a fusion protein; alternatively, the proteins maybe separated by a distance sufficient to ensure the proteins form proper secondary and tertiary structure needed for biological activity. Suitable linker sequences will adopt a flexible extended confirmation and will not exhibit a propensity for developing an ordered secondary structure which could interact with the function domains of the fusions proteins, and will have minimal hydrophobic or charged character which could also interfere with the function of fusion domains. Linker sequences should be constructed with the 15 residue repeat in mind, as it may not be in the best interest of producing a biologically active protein to tightly constrict the N or C terminus of the heterologous sequence. Beyond these considerations, the length of the linker sequence may vary without significantly affecting the biological activity of the fusion protein. Linker sequences can be used between any and all components of the fusion protein (or expression construct) including affinity tags and signal peptides. An example linker is the GSGG sequence (SEQ ID NO: 26).

A further component of the fusion protein can be an affinity tag. Such tags do not alter the biological activity of fusion proteins, are highly antigenic, and provides an epitope that can be reversibly bound by a specific binding molecule, such as a monoclonal antibody, enabling repaid detection and purification of an expressed fusion protein. Affinity tags can also convey resistance to intracellular degradation if proteins are produced in bacteria, like *E. coli*. An exemplary affinity tag is the FLAG Tag (SEQ ID NO: 27) or the $HIS_6$ Tag (SEQ ID NO: 28). Methods of producing fusion proteins utilizing this affinity tag for purification are described in U.S. Pat. No. 5,011,912.

A still further component of the fusion protein can be a signal sequence or leader sequence. These sequences are generally utilized to allow for secretion of the fusion protein from the host cell during expression and are also known as a leader sequence, prepro sequence or pre sequence. The secretory signal sequence may be that of the heterologous protein being produced, if it has such a sequence, or may be derived from another secreted protein (e.g., t-PA) or synthesized de novo. The secretory signal sequence is operably linked to fusion protein DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Thus, the nucleic acid compositions of the present invention find use in the preparation of all or a portion of the VASP-zB7R1 or VASP-CD155 fusion proteins, as described above. The subject polynucleotides (including cDNA or the full-length gene) can be used to express a partial or complete gene product. Constructs comprising the subject polynucleotides can be generated synthetically. Alternatively, single-step assembly of a gene and entire plasmid from large numbers of oligodeoxyribonucleotides is described by, e.g., Stemmer et al., *Gene (Amsterdam)* (1995) 164(1):49-53. In this method, assembly PCR (the synthesis of long DNA sequences from large numbers of oligodeoxyribonucleotides (oligos)) is described. The method is derived from DNA shuffling (Stemmer, *Nature* (1994) 370:389-391), and does not rely on DNA ligase, but instead relies on DNA polymerase to build increasingly longer DNA fragments during the assembly process. Appropriate polynucleotide constructs are purified using standard recombinant DNA techniques as described in, for example, Sambrook et al., *Molecular Cloning: A Laboratory Manual*, 2nd Ed., (1989) Cold Spring Harbor Press, Cold Spring Harbor, N.Y., and under current regulations described in United States Dept. of HHS, National Institute of Health (NIH) Guidelines for Recombinant DNA Research.

Polynucleotide molecules comprising a polynucleotide sequence provided herein are propagated by placing the molecule in a vector. Viral and non-viral vectors are used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

For expression, an expression cassette or system may be employed. The gene product encoded by a polynucleotide of the invention is expressed in any convenient expression system, including, for example, bacterial, yeast, insect, amphibian and mammalian systems. Suitable vectors and host cells are described in U.S. Pat. No. 5,654,173. In the expression vector, the heterologous protein encoding polynucleotide (such as the extracellular domain of zB7R1; i.e. SEQ ID NO:3 or 7) is linked to a regulatory sequence as appropriate to obtain the desired expression properties. These can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the DNA encoding the VASP-heterologous fusion protein, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

VASP-Heterologous fusion proteins may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, HEK 293, CHO, *Xenopus* Oocytes, etc., may be used as the expression host cells. In some situations, it is desirable to express a polymorphic VASP nucleic acid molecule in eukaryotic cells, where the polymorphic VASP protein will benefit from native folding and post-translational modifications. Small peptides can also be synthesized in the laboratory. Polypeptides that are subsets of the complete VASP sequence may be used to identify and investigate parts of the protein important for function.

Specific expression systems of interest include bacterial, yeast, insect cell and mammalian cell derived expression systems. Representative systems from each of these categories is are provided below: Bacteria. Expression systems in bacteria include those described in Chang et al., *Nature* (1978) 275:615; Goeddel et al., *Nature* (1979) 281:544; Goeddel et al., *Nucleic Acids Res.* (1980) 8:4057; EP 0 036,776; U.S. Pat. No. 4,551,433; DeBoer et al., *Proc. Natl. Acad. Sci.* (USA) (1983) 80:21-25; and Siebenlist et al., *Cell* (1980) 20:269. Yeast. Expression systems in yeast include those described in Hinnen et al., *Proc. Natl. Acad. Sci.* (USA) (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459; Roggenkamp et al., *Mol. Gen. Genet.* (1986) 202:302; Das et al., *J. Bacteriol.* (1984) 158:1165; De Louvencourt et al., *J. Bacteriol.* (1983) 154:737; Van den Berg et al., *Bio/Technology* (1990) 8:135; Kunze et al., *J. Basic Microbiol.* (1985) 25:141; Cregg et al., *Mol. Cell. Biol.* (1985) 5:3376; U.S. Pat. Nos. 4,837,148 and 4,929,555; Beach and Nurse, *Nature* (1981) 300:706; Davidow et al., *Curr. Genet.* (1985) 10:380; Gaillardin et al., *Curr. Genet.* (1985) 10:49; Ballance et al., *Biochem. Biophys. Res. Commun.* (1983) 112:284-289; Tilburn et al., *Gene* (1983) 26:205-221; Yelton et al., *Proc. Natl. Acad. Sci.* (USA) (1984) 81:1470-1474; Kelly and Hynes, *EMBO 1* (1985) 4:475479; EP 0 244,234; and WO 91/00357. Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J. Gen. Virol.* (1988) 69:765-776; Miller et al., *Ann. Rev. Microbiol.* (1988) 42:177; Carbonell et al., *Gene* (1988) 73:409; Maeda et al., *Nature* (1985) 315:592-594; Lebacq-Verheyden et al., *Mol. Cell. Biol.* (1988) 8:3129; Smith et al., *Proc. Natl. Acad. Sci.* (USA) (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47-55, Miller et al., *Generic Engineering* (1986) 8:277-279, and Maeda et al., *Nature* (1985) 315:592-594. Mammalian Cells. Mammalian expression is accomplished as described in Dijkema et al., *EMBO 1* (1985) 4:761, Gorman et al., *Proc. Natl. Acad. Sci.* (USA) (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927, 762, 4,560,655, WO 90/103430, WO 87/00195, and U.S. Pat. No. RE 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to a selected polynucleotide is identified, its expression can be regulated-in the cell to which the gene is native. For example, an endogenous gene of a cell can be regulated by an exogenous regulatory sequence inserted into the genome of the cell at location sufficient to at least enhance expressed of the gene in the cell. The regulatory sequence may be designed to integrate into the genome via homologous recombination, as disclosed in U.S. Pat. Nos. 5,641,670 and 5,733,761, the disclosures of which are herein incorporated by reference, or may be designed to integrate into the genome via non-homologous recombination, as described in WO 99/15650, the disclosure of which is herein incorporated by reference.

The invention further provides recombinant vectors and host cells comprising polynucleotides of the invention. In general, recombinant vectors and host cells of the invention are isolated; however, a host cell comprising a polynucleotide of the invention may be part of a genetically modified animal.

The present invention further provides recombinant vectors ("constructs") comprising a polynucleotide of the invention. Recombinant vectors include vectors used for propagation of a polynucleotide of the invention, and expression vectors. Vectors useful for introduction of the polynucleotide include plasmids and viral vectors, e.g. retroviral-based vectors, adenovirus vectors, etc. that are maintained transiently or stably in mammalian cells. A wide variety of vectors can be employed for transfection and/or integration of the gene into the genome of the cells. Alternatively, micro-injection may be employed, fusion, or the like for introduction of genes into a suitable host cell.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, at least about 25 amino acids, at least about 45 amino acids, and up to the complete open reading frame of the gene. After introduction of the DNA, the cells containing the construct may be selected by means of a selectable marker, the cells expanded and then used for expression.

The expression cassettes may be introduced into a variety of vectors, e.g. plasmid, BAC, YAC, bacteriophage such as lambda, P1, M13, etc., animal or plant viruses, and the like, where the vectors are normally characterized by the ability to provide selection of cells comprising the expression vectors. The vectors may provide for extrachromosomal maintenance, particularly as plasmids or viruses, or for integration into the host chromosome. Where extrachromosomal maintenance is desired, an origin sequence is provided for the replication of the plasmid, which may be low- or high copy-number. A wide variety of markers are available for selection, particularly those which protect against toxins, more particularly against antibiotics. The particular marker that is chosen is selected in accordance with the nature of the host, where in some cases, complementation may be employed with auxotrophic hosts. Introduction of the DNA construct may use any convenient method, e.g. conjugation, bacterial transformation, calcium-precipitated DNA, electroporation, fusion, transfection, infection with viral vectors, biolistics, etc.

The present invention further provides host cells, which may be isolated host cells, comprising polymorphic VASP nucleic acid molecules of the invention. Suitable host cells include prokaryotes such as E. coli, B. subtilis, eukaryotes, including insect cells in combination with baculovirus vectors, yeast cells, such as Saccharomyces cerevisiae, or cells of a higher organism such as vertebrates, including amphibians (e.g., Xenopus laevis oocytes), and mammals, particularly humans, e.g. COS cells, CHO cells, HEK293 cells, and the like, may be used as the host cells. Host cells can be used for the purposes of propagating a polymorphic VASP nucleic acid molecule, for production of a polymorphic VASP polypeptide, or in cell-based methods for identifying agents which modulate a level of VASP mRNA and/or protein and/or biological activity in a cell.

Primary or cloned cells and cell lines may be modified by the introduction of vectors comprising a DNA encoding the VASP-heterologous fusion protein polymorphism(s). The isolated polymorphic VASP nucleic acid molecule may comprise one or more variant sequences, e.g., a haplotype of commonly occurring combinations. In one embodiment of the invention, a panel of two or more genetically modified cell lines, each cell line comprising a VASP polymorphism, are provided for substrate and/or expression assays. The panel may further comprise cells genetically modified with other genetic sequences, including polymorphisms, particularly other sequences of interest for pharmacogenetic screening, e.g. other genes/gene mutations associated with obesity, a number of which are known in the art.

The subject nucleic acids can be used to generate genetically modified non-human animals or site specific gene modifications in cell lines. The term "transgenic" is intended to encompass genetically modified animals having the addition of DNA encoding the VASP-heterologous fusion protein or having an exogenous DNA encoding the VASP-heterologous fusion protein that is stably transmitted in the host cells. Transgenic animals may be made through homologous recombination. Alternatively, a nucleic acid construct is randomly integrated into the genome. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

DNA constructs for homologous recombination will comprise at least a portion of the DNA encoding the VASP-heterologous fusion protein and will include regions of homology to the target locus. Conveniently, markers for positive and negative selection are included. Methods for generating cells having targeted gene modifications through homologous recombination are known in the-art. For various techniques for transfecting mammalian cells, see Known et al. (1990) *Methods in Enzymology* 185:527-537.

For embryonic stem (ES) cells, an ES cell line may be employed, or ES cells may be obtained freshly from a host, e.g. mouse, rat, guinea pig, etc. Such cells are grown on an appropriate fibroblast-feeder layer or grown in the presence of leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination. Those colonies that show homologous recombination may then be used for embryo manipulation and blastocyst injection. Blastocysts are obtained from. 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected. The chimeric animals are screened for the presence of the DNA encoding the VASP-heterologous fusion protein and males and females having the modification are mated to produce homozygous progeny. The transgenic animals may be any non-human mammal, such as laboratory animals, domestic animals, etc. The transgenic animals may be used to determine the effect of a candidate drug in an in vivo environment.

The present invention is a method of preparing a soluble, homo- or hetero-trimeric protein by culturing a host cell transformed or transfected with at least one or up to four different expression vectors encoding a fusion protein comprising a VASP domain and a heterologous protein. In order to produce a biologically functioning protein, the four VASP domains preferentially form a homo- or hetero-tetramers. The culturing can also occur in the same host cell, if efficient production can be maintained, and homo- or hetero-tetrameric proteins are then isolated from the medium. Ideally, the four heterologous proteins are differentially labeled with various tag sequences (i.e., His tag, FLAG tag, and Glu-Glu tag) to allow analysis of the composition or purification of the resulting molecules. Alternatively, the four components can be produced separately and combined in deliberate ratios to result in the hetero-tetrameric molecules desired. The VASP domains utilized in making these hetero-trimeric molecules can be the same or different and the fusion protein(s) can further comprise a linker sequence. In one particular embodiment, the heterologous proteins used to form the homo-tetrameric protein is the soluble domain of zB7R1.

One result of the use of the VASP tetramerization domain of the present invention is the ability to increase the affinity and avidity of the heterologous protein for its ligand or binding partner through the formation of the tetrameric form. By avidity, it is meant the strength of binding of multiple molecules to a larger molecule, a situation exemplified but not limited to the binding of a complex antigen by an antibody. Such a characteristic would be improved or formed for many heterologous proteins, for example, by the formation of multiple binding sites for its ligand or ligands through the tetramerization of the heterologous receptor using the VASP domain. By affinity, it is meant the strength of binding of a simple receptor-ligand system. Such a characteristic would be improved for a subset of heterologous proteins using the tetramerization domain of the present invention, for example, by forming a binding site with better binding characteristics for a single ligand through the tetramerization of the receptor. Avidity and affinity can be measured using standard assays well known to one of ordinary skill, for example, the methods described in the examples below. An improvement in affinity or avidity occurs when the affinity or avidity value (for example, affinity constant or Ka) for the tetramerization domain-heterologous protein fusion and its ligand is higher than for the heterologous protein alone and its ligand. An alternative means of measuring these characteristics is the equilibrium constant (Kd) where a decrease would be observed with the improvement in affinity or avidity using the VASP tetramerization domain of the present invention.

Biological activity of recombinant VASP-heterologous fusion proteins is mediated by binding of the recombinant fusion protein to a cognate molecule, such as a receptor or cross-receptor. A cognate molecule is defined as a molecule which binds the recombinant fusion protein in a non-covalent interaction based upon the proper conformation of the recombinant fusion protein and the cognate molecule. For example, for a recombinant fusion protein comprising an extracellular region of a receptor, the cognate molecule comprises a ligand which binds the extracellular region of the receptor. Conversely, for a recombinant soluble fusion protein comprising a ligand, the cognate molecule comprises a receptor (or binding protein) which binds the ligand.

Binding of a recombinant fusion protein to a cognate molecule is a marker for biological activity. Such binding activity may be determined, for example, by competition for binding to the binding domain of the cognate molecule (i.e. competitive binding assays). One configuration of a competitive binding assay for a recombinant fusion protein comprising a ligand uses a radiolabeled, soluble receptor, and intact cells expressing a native form of the ligand. Similarly, a competitive assay for a recombinant fusion protein comprising a receptor uses a radiolabeled, soluble ligand, and intact cells expressing a native form of the receptor. Such an assay is described in Example 3. Instead of intact cells expressing a native form of the cognate molecule, one could substitute purified cognate molecule bound to a solid phase. Competitive binding assays can be performed using standard methodology. Qualitative or semi-quantitative results can be obtained by competitive autoradiographic plate binding assays, or fluorescence activated cell sorting, or Scatchard plots may be utilized to generate quantitative results.

Biological activity may also be measured using bioassays that are known in the art, such as a cell proliferation assay. An exemplary bioassay is described in Example 4. The type of cell proliferation assay used will depend upon the recombinant soluble fusion protein. For example, a bioassay for a recombinant soluble fusion protein that in its native form acts upon T cells will utilize purified T cells obtained by methods that are known in the art. Such bioassays include costimulation assays in which the purified T cells are incubated in the presence of the recombinant soluble fusion protein and a suboptimal level of a mitogen such as Con A or PHA. Similarly, purified B cells will be used for a recombinant soluble fusion protein that in its native form acts upon B cells. Other types of cells may also be selected based upon the cell type upon which the native form of the recombinant soluble fusion protein acts. Proliferation is determined by measuring the incorporation of a radiolabeled substance, such as $^3$H thymidine, according to standard methods.

Yet another type assay for determining biological activity is induction of secretion of secondary molecules. For example, certain proteins induce secretion of cytokines by T cells. T cells are purified and stimulated with a recombinant soluble fusion protein under the conditions required to induce cytokine secretion (for example, in the presence of a comitogen). Induction of cytokine secretion is determined by bioassay, measuring the proliferation of a cytokine dependent cell line. Similarly, induction of immunoglobulin secretion is determined by measuring the amount of immunoglobulin secreted by purified B cells stimulated with a recombinant soluble fusion protein that acts on B cells in its native form, using a quantitative (or semi-quantitative) assay such as an enzyme immunoassay.

If the binding partner for a particular heterologous protein is unknown, the VASP-fusion protein can be used in a binding assay to seek out that binding partner. One method of doing this, called a secretion trap assay, is described in Example 5, although other methods of using a VASP-fusion protein to identify binding partners are well known to one of ordinary skill.

To assay the zB7R1 agonist and/or antagonist polypeptides and antibodies of the present invention, mammalian cells suitable for use in expressing zB7R1-comprising receptors and transducing a receptor-mediated signal include cells that express other receptor subunits that may form a functional complex with zB7R1 (or zB7R1RA). Within a preferred embodiment, the cell is dependent upon an exogenously supplied hematopoietic growth factor for its proliferation. Preferred cell lines of this type are the human TF-1 cell line (ATCC number CRL-2003) and the AML-193 cell line (ATCC number CRL-9589), which are GM-CSF-dependent human leukemic cell lines and BaF3 (Palacios and Steinmetz, Cell 41: 727-734, (1985)) which is an IL-3 dependent murine pre-B cell line. Other cell lines include BHK, COS-1 and CHO cells. Suitable host cells can be engineered to produce the necessary receptor subunits or other cellular component needed for the desired cellular response. This approach is advantageous because cell lines can be engineered to express receptor subunits from any species, thereby overcoming potential limitations arising from species specificity. Species orthologs of the human receptor cDNA can be cloned and used within cell lines from the same species, such as a mouse cDNA in the BaF3 cell line.

Cells expressing functional receptor are used within screening assays. A variety of suitable assays are known in the art. These assays are based on the detection of a biological response in a target cell. One such assay is a cell proliferation assay. Cells are cultured in the presence or absence of a test compound, and cell proliferation is detected by, for example, measuring incorporation of tritiated thymidine or by colorimetric assay based on the metabolic breakdown of 3-(4,5-dimethylthiazol-2-yl)-2,5-diphenyl tetrazolium bromide (MTT) (Mosman, *J. Immunol. Meth.* 65: 55-63, (1983)). An alternative assay format uses cells that are further engineered to express a reporter gene. The reporter gene is linked to a promoter element that is responsive to the receptor-linked pathway, and the assay detects activation of transcription of the reporter gene. A preferred promoter element in this regard is a serum response element, or SRE. See, e.g., Shaw et al., *Cell* 56:563-572, (1989). A preferred such reporter gene is a luciferase gene (de Wet et al., *Mol. Cell. Biol.* 7:725, (1987)). Expression of the luciferase gene is detected by luminescence using methods known in the art (e.g., Baumgartner et al., *J. Biol. Chem.* 269:29094-29101, (1994); Schenborn and Goiffin, *Promega_Notes* 41:11, 1993). Luciferase activity assay kits are commercially available from, for example, Promega Corp., Madison, Wis. Target cell lines of this type can be used to screen libraries of chemicals, cell-conditioned culture media, fungal broths, soil samples, water samples, and the like. For example, a bank of cell-conditioned media samples can be assayed on a target cell to identify cells that produce counter-receptor. Positive cells are then used to produce a cDNA library in a mammalian expression vector, which is divided into pools, transfected into host cells, and expressed. Media samples from the transfected cells are then assayed, with subsequent division of pools, re-transfection, subculturing, and re-assay of positive cells to isolate a cloned cDNA encoding the counter-receptor.

Several zB7R1 responsive cell lines are known in the art or can be constructed, for example, the Baf3/DIRS1/cytoR11 cell line (WIPO Publication No. WO 02/072607). Moreover several IL-22 responsive cell lines are known (Dumontier et al., *J. Immunol.* 164:1814-1819, 2000; Dumoutier, L. et al., *Proc. Nat'l. Acad. Sci.* 97:10144-10149, 2000; Xie M H et al., *J. Biol. Chem.* 275: 31335-31339, 2000; Kotenko S V et al., *J. Biol. Chem.* 276:2725-2732, 2001), as well as those that express the IL-22 receptor subunit zB7R1. For example, the following cells are responsive to IL-22: TK-10 (Xie M H et al., supra.) (human renal carcinoma); SW480 (ATCC No. CCL-228) (human colon adenocarcinoma); HepG2 (ATCC No. HB-8065) (human hepatoma); PC12 (ATCC No. CRL-1721) (murine neuronal cell model; rat pheochromocytoma); and MES13 (ATCC No. CRL-1927) (murine kidney mesangial cell line). In addition, some cell lines express zB7R1 (IL-22 receptor) are also candidates for responsive cell lines to IL-22: A549 (ATCC No. CCL-185) (human lung carcinoma); G-361 (ATCC No. CRL-1424) (human melanoma); and Caki-1 (ATCC No. HTB-46) (human renal carcinoma). In addition, IL-22-responsive cell lines can be constructed, for example, the Baf3/cytoR11/CRF2-4 cell line described herein (WIPO Publication No. WO 02/12345). These cells can be used in assays to assess the functionality of zB7R1 as an zB7R1 or IL-22 antagonist or anti-inflammatory factor.

7. Production of zB7R1 or CD155 Fusion Proteins and Conjugates

One general class of zB7R1 or CD155 analogs are variants having an amino acid sequence that is a mutation of the amino acid sequence disclosed herein. Another general class of zB7R1 or CD155 analogs is provided by anti-idiotype antibodies, and fragments thereof, as described below. Moreover, recombinant antibodies comprising anti-idiotype variable domains can be used as analogs (see, for example, Monfardini et al., *Proc. Assoc. Am. Physicians* 108:420 (1996)). Since the variable domains of anti-idiotype zB7R1 antibodies mimic zB7R1, these domains can provide zB7R1 binding activity. Methods of producing anti-idiotypic catalytic antibodies are known to those of skill in the art (see, for example, Joron et al., *Ann. N Y Acad. Sci.* 672:216 (1992), Friboulet et al., *Appl. Biochem. Biotechnol.* 47:229 (1994), and Avalle et al., *Ann. N Y Acad. Sci.* 864:118 (1998)).

Another approach to identifying zB7R1 or Cd155 analogs is provided by the use of combinatorial libraries. Methods for constructing and screening phage display and other combinatorial libraries are provided, for example, by Kay et al., *Phage Display of Peptides and Proteins* (Academic Press 1996), Verdine, U.S. Pat. No. 5,783,384, Kay, et. al., U.S. Pat. No. 5,747,334, and Kauffman et al., U.S. Pat. No. 5,723,323.

zB7R1 and CD155 polypeptides have both in vivo and in vitro uses. As an illustration, a soluble form of zB7R1 can be added to cell culture medium to inhibit the effects of the zB7R1 counter-receptor produced by the cultured cells.

Fusion proteins of zB7R1 can be used to express zB7R1 in a recombinant host, and to isolate the produced zB7R1. As described below, particular zB7R1 fusion proteins also have uses in diagnosis and therapy. One type of fusion protein comprises a peptide that guides a zB7R1 polypeptide from a recombinant host cell. To direct a zB7R1 polypeptide into the secretory pathway of a eukaryotic host cell, a secretory signal sequence (also known as a signal peptide, a leader sequence, prepro sequence or pre sequence) is provided in the zB7R1 expression vector. While the secretory signal sequence may be derived from zB7R1, a suitable signal sequence may also be derived from another secreted protein or synthesized de novo. The secretory signal sequence is operably linked to a zB7R1-encoding sequence such that the two sequences are joined in the correct reading frame and positioned to direct the newly synthesized polypeptide into the secretory pathway of the host cell. Secretory signal sequences are commonly positioned 5' to the nucleotide sequence encoding the polypeptide of interest, although certain secretory signal sequences may be positioned elsewhere in the nucleotide sequence of interest (see, e.g., Welch et al., U.S. Pat. No. 5,037,743; Holland et al., U.S. Pat. No. 5,143,830).

Although the secretory signal sequence of zB7R1 or another protein produced by mammalian cells (e.g., tissue-type plasminogen activator signal sequence, as described, for example, in U.S. Pat. No. 5,641,655) is useful for expression of zB7R1 in recombinant mammalian hosts, a yeast signal sequence is preferred for expression in yeast cells. Examples of suitable yeast signal sequences are those derived from yeast mating phermone α-factor (encoded by the MFα1 gene), invertase (encoded by the SUC2 gene), or acid phosphatase (encoded by the PHOS gene). See, for example, Romanos et al., "Expression of Cloned Genes in Yeast," in *DNA Cloning 2: A Practical Approach, 2nd Edition*, Glover and Hames (eds.), pages 123-167 (Oxford University Press 1995).

zB7R1 soluble receptor polypeptides can be prepared by expressing a truncated DNA encoding the extracellular domain, for example, a polypeptide which contains SEQ ID NO:2 or 5, or the corresponding region of a non-human receptor. It is preferred that the extracellular domain polypeptides be prepared in a form substantially free of transmembrane and intracellular polypeptide segments. To direct the export of the receptor domain from the host cell, the receptor DNA is linked to a second DNA segment encoding a secretory peptide, such as a t-PA secretory peptide. To facilitate purification of the secreted receptor domain, a C-terminal extension, such as a poly-histidine tag, substance P, Flag™ peptide (Hopp et al., *Biotechnology* 6:1204-1210, (1988); available from Eastman Kodak Co., New Haven, Conn.) or another polypeptide or protein for which an antibody or other specific binding agent is available, can be fused to the receptor polypeptide. Moreover, zB7R1 antigenic epitopes from the extracellular cytokine binding domains are also prepared as described above.

In an alternative approach, a receptor extracellular domain of zB7R1 or other B7 receptor component can be expressed as a fusion with immunoglobulin heavy chain constant regions, typically an $F_c$ fragment, which contains two constant region domains and a hinge region but lacks the variable region (See, Sledziewski, A Z et al., U.S. Pat. Nos. 6,018,026 and 5,750,375). The soluble zB7R1 polypeptides of the present invention include such fusions. Such fusions are typically secreted as multimeric molecules wherein the Fc portions are disulfide bonded to each other and two other receptor polypeptides are arrayed in closed proximity to each other. Fusions of this type can be used to affinity purify the cognate counter-receptor from solution, as an in vitro assay tool, to block, inhibit or reduce signals in vitro by specifically titrating out counter-receptor, and as antagonists in vivo by administering them parenterally to bind circulating counter-receptor and clear it from the circulation. To purify counter-receptor, a zB7R1-Ig chimera is added to a sample containing the counter-receptor (e.g., cell-conditioned culture media or tissue extracts) under conditions that facilitate receptor-counter-receptor binding (typically near-physiological temperature, pH, and ionic strength). The chimera-counter-receptor complex is then separated by the mixture using protein A, which is immobilized on a solid support (e.g., insoluble resin beads). The counter-receptor is then eluted using conventional chemical techniques, such as with a salt or pH gradient. In the alternative, the chimera itself can be bound to a solid support, with binding and elution carried out as above. The chimeras may be used in vivo to regulate inflammatory responses including acute phase responses such as serum amyloid A (SAA), C-reactive protein (CRP), and the like. Chimeras with high binding affinity are administered parenterally (e.g., by intramuscular, subcutaneous or intravenous injection). Circulating molecules bind counter-receptor and are cleared from circulation by normal physiological processes. For use in assays, the chimeras are bound to a support via the $F_c$ region and used in an ELISA format.

To assist in isolating anti-zB7R1 and binding partners of the present invention, an assay system that uses a counter-receptor-binding receptor (or an antibody, one member of a complement/anti-complement pair) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229-40, 1991 and Cunningham and Wells, *J. Mol. Biol.* 234:554-63, 1993. A receptor, antibody, member or fragment is covalently attached, using amine or sulfhydryl chemistry, to dextran fibers that are attached to gold film within the flow cell. A test sample is passed through the cell. If a counter-receptor, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding. Alternatively, counter-receptor/receptor binding can be analyzed using SELDI™ technology (Ciphergen, Inc., Palo Alto, Calif.). Moreover, BIACORE technology, described above, can be used to be used in competition experiments to determine if different monoclonal antibodies bind the same or different epitopes on the zB7R1 polypeptide, and as such, be used to aid in epitope mapping of antibodies of the present invention.

Counter-receptor-binding polypeptides (i.e. CD155) can also be used within other assay systems known in the art. Such systems include Scatchard analysis for determination of binding affinity (see Scatchard, *Ann. NY Acad. Sci.* 51: 660-72, 1949) and calorimetric assays (Cunningham et al., *Science* 253:545-48, 1991; Cunningham et al., *Science* 245: 821-25, 1991).

The present invention further provides a variety of other polypeptide fusions and related multimeric proteins comprising one or more polypeptide fusions. For example, a soluble zB7R1 receptor can be prepared as a fusion to a dimerizing protein as disclosed in U.S. Pat. Nos. 5,155,027 and 5,567,584. Preferred dimerizing proteins in this regard include immunoglobulin constant region domains, e.g., IgGγ1, and the human κ light chain. Immunoglobulin-soluble zB7R1 fusions can be expressed in genetically engineered cells to produce a variety of multimeric zB7R1 receptor analogs. Auxiliary domains can be fused to soluble zB7R1 receptor to target them to specific cells, tissues, or macromolecules (e.g., collagen, or cells expressing the zB7R1 counter-receptors). A zB7R1 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1-9, 1996.

In bacterial cells, it is often desirable to express a heterologous protein as a fusion protein to decrease toxicity, increase stability, and to enhance recovery of the expressed protein. For example, zB7R1 can be expressed as a fusion protein comprising a glutathione S-transferase polypeptide. Glutathione S-transferease fusion proteins are typically soluble, and easily purifiable from *E. coli* lysates on immobilized glutathione columns. In similar approaches, a zB7R1 fusion protein comprising a maltose binding protein polypeptide can be isolated with an amylose resin column, while a fusion protein comprising the C-terminal end of a truncated Protein A gene can be purified using IgG-Sepharose. Established techniques for expressing a heterologous polypeptide as a fusion protein in a bacterial cell are described, for example, by Williams et al., "Expression of Foreign Proteins in *E. coli* Using Plasmid Vectors and Purification of Specific Polyclonal Antibodies," in *DNA Cloning 2: A Practical Approach*, $2^{nd}$ Edition, Glover and Hames (Eds.), pages 15-58 (Oxford University Press 1995). In addition, commercially available expression systems are available. For example, the PINPOINT Xa protein purification system (Promega Corporation; Madison, Wis.) provides a method for isolating a fusion protein comprising a polypeptide that becomes biotinylated during expression with a resin that comprises avidin.

Peptide tags that are useful for isolating heterologous polypeptides expressed by either prokaryotic or eukaryotic cells include polyHistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., *Arch. Biochem. Biophys.* 329:215 (1996), Morganti et al., *Biotechnol. Appl. Biochem.* 23:67 (1996), and Zheng et al., *Gene* 186:55 (1997). Nucleic acid molecules encoding such peptide tags are available, for example, from Sigma-Aldrich Corporation (St. Louis, Mo.).

Another form of fusion protein comprises a zB7R1 polypeptide and an immunoglobulin heavy chain constant region, typically an $F_c$ fragment, which contains two or three constant region domains and a hinge region but lacks the variable region. As an illustration, Chang et al., U.S. Pat. No. 5,723,125, describe a fusion protein comprising a human interferon and a human immunoglobulin Fc fragment. The C-terminal of the interferon is linked to the N-terminal of the Fc fragment by a peptide linker moiety. An example of a peptide linker is a peptide comprising primarily a T cell inert sequence, which is immunologically inert. In this fusion protein, an illustrative Fc moiety is a human γ4 chain, which is stable in solution and has little or no complement activating activity. Accordingly, the present invention contemplates a zB7R1 fusion protein that comprises a zB7R1 moiety and a human Fc fragment, wherein the C-terminus of the zB7R1 moiety is attached to the N-terminus of the Fc fragment via a peptide linker. The zB7R1 moiety can be a zB7R1 molecule or a fragment thereof. For example, a fusion protein can comprise the amino acid of SEQ ID NO:3 and an Fc fragment (e.g., a human Fc fragment).

In another variation, a zB7R1 fusion protein comprises an IgG sequence, a zB7R1 moiety covalently joined to the aminoterminal end of the IgG sequence, and a signal peptide that is covalently joined to the aminoterminal of the zB7R1 moiety, wherein the IgG sequence consists of the following elements in the following order: a hinge region, a $CH_2$ domain, and a $CH_3$ domain. Accordingly, the IgG sequence lacks a $CH_1$ domain. The zB7R1 moiety displays a zB7R1 activity, as described herein, such as the ability to bind with a zB7R1 counter-receptor. This general approach to producing fusion proteins that comprise both antibody and nonantibody portions has been described by LaRochelle et al., EP 742830 (WO 95/21258).

Fusion proteins comprising a zB7R1 moiety and an Fc moiety can be used, for example, as an in vitro assay tool. For example, the presence of a zB7R1 counter-receptor in a biological sample can be detected using a zB7R1-immunoglobulin fusion protein, in which the zB7R1 moiety is used to bind the counter-receptor, and a macromolecule, such as Protein A or anti-Fc antibody, is used to bind the fusion protein to a solid support. Such systems can be used to identify agonists and antagonists that interfere with the binding of zB7R1 to its counter-receptor.

Other examples of antibody fusion proteins include polypeptides that comprise an antigen-binding domain and a zB7R1 fragment that contains a zB7R1 extracellular domain. Such molecules can be used to target particular tissues for the benefit of zB7R1 binding activity.

The present invention further provides a variety of other polypeptide fusions. For example, part or all of a domain(s) conferring a biological function can be swapped between zB7R1 of the present invention with the functionally equivalent domain(s) from another member of the cytokine receptor family. Polypeptide fusions can be expressed in recombinant host cells to produce a variety of zB7R1 fusion analogs. A zB7R1 polypeptide can be fused to two or more moieties or domains, such as an affinity tag for purification and a targeting domain. Polypeptide fusions can also comprise one or more cleavage sites, particularly between domains. See, for example, Tuan et al., *Connective Tissue Research* 34:1 (1996).

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. General methods for enzymatic and chemical cleavage of fusion proteins are described, for example, by Ausubel (1995) at pages 16-19 to 16-25.

zB7R1 binding domains can be further characterized by physical analysis of structure, as determined by such techniques as nuclear magnetic resonance, crystallography, electron diffraction or photoaffinity labeling, in conjunction with mutation of putative contact site amino acids of zB7R1 counter-receptor agonists. See, for example, de Vos et al., *Science* 255:306 (1992), Smith et al., *J. Mol. Biol.* 224:899 (1992), and Wlodaver et al., *FEBS Lett.* 309:59 (1992).

The present invention also contemplates chemically modified zB7R1 compositions, in which a zB7R1 polypeptide is linked with a polymer. Illustrative zB7R1 polypeptides are soluble polypeptides that lack a functional transmembrane domain, such as a polypeptide consisting of amino acid residues SEQ ID NO:3. Typically, the polymer is water soluble so that the zB7R1 conjugate does not precipitate in an aqueous environment, such as a physiological environment. An example of a suitable polymer is one that has been modified to have a single reactive group, such as an active ester for acylation, or an aldehyde for alkylation. In this way, the degree of polymerization can be controlled. An example of a reactive aldehyde is polyethylene glycol propionaldehyde, or mono-(C1-C10) alkoxy, or aryloxy derivatives thereof (see, for example, Harris, et al., U.S. Pat. No. 5,252,714). The polymer may be branched or unbranched. Moreover, a mixture of polymers can be used to produce zB7R1 conjugates.

zB7R1 conjugates used for therapy can comprise pharmaceutically acceptable water-soluble polymer moieties. Suitable water-soluble polymers include polyethylene glycol (PEG), monomethoxy-PEG, mono-(C1-C10)alkoxy-PEG, aryloxy-PEG, poly-(N-vinyl pyrrolidone) PEG, tresyl monomethoxy PEG, PEG propionaldehyde, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A zB7R1 conjugate can also comprise a mixture of such water-soluble polymers.

One example of a zB7R1 conjugate comprises a zB7R1 moiety and a polyalkyl oxide moiety attached to the N-terminus of the zB7R1 moiety. PEG is one suitable polyalkyl oxide. As an illustration, zB7R1 can be modified with PEG, a process known as "PEGylation." PEGylation of zB7R1 can be carried out by any of the PEGylation reactions known in the art (see, for example, EP 0 154 316, Delgado et al., *Critical Reviews in Therapeutic Drug Carrier Systems* 9:249 (1992), Duncan and Spreafico, *Clin. Pharmacokinet.* 27:290 (1994), and Francis et al., *Int J Hematol* 68:1 (1998)). For example, PEGylation can be performed by an acylation reaction or by an alkylation reaction with a reactive polyethylene glycol molecule. In an alternative approach, zB7R1 conjugates are formed by condensing activated PEG, in which a terminal hydroxy or amino group of PEG has been replaced by an activated linker (see, for example, Karasiewicz et al., U.S. Pat. No. 5,382,657).

PEGylation by acylation typically requires reacting an active ester derivative of PEG with a zB7R1 polypeptide. An example of an activated PEG ester is PEG esterified to N-hydroxysuccinimide. As used herein, the term "acylation" includes the following types of linkages between zB7R1 and a water soluble polymer: amide, carbamate, urethane, and the like. Methods for preparing PEGylated zB7R1 by acylation will typically comprise the steps of (a) reacting a zB7R1 polypeptide with PEG (such as a reactive ester of an aldehyde derivative of PEG) under conditions whereby one or more PEG groups attach to zB7R1, and (b) obtaining the reaction product(s). Generally, the optimal reaction conditions for acylation reactions will be determined based upon known parameters and desired results. For example, the larger the ratio of PEG:zB7R1, the greater the percentage of polyPEGylated zB7R1 product.

The product of PEGylation by acylation is typically a polyPEGylated zB7R1 product, wherein the lysine ε-amino groups are PEGylated via an acyl linking group. An example of a connecting linkage is an amide. Typically, the resulting zB7R1 will be at least 95% mono-, di-, or tri-pegylated, although some species with higher degrees of PEGylation may be formed depending upon the reaction conditions. PEGylated species can be separated from unconjugated zB7R1 polypeptides using standard purification methods, such as dialysis, ultrafiltration, ion exchange chromatography, affinity chromatography, and the like.

PEGylation by alkylation generally involves reacting a terminal aldehyde derivative of PEG with zB7R1 in the presence of a reducing agent. PEG groups can be attached to the polypeptide via a —$CH_2$—NH group.

Moreover, anti-zB7R1 antibodies or antibody fragments of the present invention can be PEGylated using methods in the art and described herein.

Derivatization via reductive alkylation to produce a monoPEGylated product takes advantage of the differential reactivity of different types of primary amino groups available for derivatization. Typically, the reaction is performed at a pH that allows one to take advantage of the pKa differences between the ε-amino groups of the lysine residues and the α-amino group of the N-terminal residue of the protein. By such selective derivatization, attachment of a water-soluble polymer that contains a reactive group such as an aldehyde, to a protein is controlled. The conjugation with the polymer occurs predominantly at the N-terminus of the protein without significant modification of other reactive groups such as the lysine side chain amino groups. The present invention provides a substantially homogenous preparation of zB7R1 monopolymer conjugates.

Reductive alkylation to produce a substantially homogenous population of monopolymer zB7R1 conjugate molecule can comprise the steps of: (a) reacting a zB7R1 polypeptide with a reactive PEG under reductive alkylation conditions at a pH suitable to permit selective modification of the α-amino group at the amino terminus of the zB7R1, and (b) obtaining the reaction product(s). The reducing agent used for reductive alkylation should be stable in aqueous solution and able to reduce only the Schiff base formed in the initial process of reductive alkylation. Illustrative reducing agents include sodium borohydride, sodium cyanoborohydride, dimethylamine borane, trimethylamine borane, and pyridine borane.

For a substantially homogenous population of monopolymer zB7R1 conjugates, the reductive alkylation reaction conditions are those that permit the selective attachment of the water-soluble polymer moiety to the N-terminus of zB7R1. Such reaction conditions generally provide for pKa differences between the lysine amino groups and the α-amino group at the N-terminus. The pH also affects the ratio of polymer to protein to be used. In general, if the pH is lower, a larger excess of polymer to protein will be desired because the less reactive the N-terminal α-group, the more polymer is needed to achieve optimal conditions. If the pH is higher, the polymer:zB7R1 need not be as large because more reactive groups are available. Typically, the pH will fall within the range of 3 to 9, or 3 to 6. This method can be employed for making zB7R1-comprising homodimeric, heterodimeric or multimeric soluble receptor conjugates.

Another factor to consider is the molecular weight of the water-soluble polymer. Generally, the higher the molecular weight of the polymer, the fewer number of polymer molecules which may be attached to the protein. For PEGylation reactions, the typical molecular weight is about 2 kDa to about 100 kDa, about 5 kDa to about 50 kDa, or about 12 kDa to about 25 kDa. The molar ratio of water-soluble polymer to zB7R1 will generally be in the range of 1:1 to 100:1. Typically, the molar ratio of water-soluble polymer to zB7R1 will be 1:1 to 20:1 for polyPEGylation, and 1:1 to 5:1 for monoPEGylation.

General methods for producing conjugates comprising a polypeptide and water-soluble polymer moieties are known in the art. See, for example, Karasiewicz et al., U.S. Pat. No. 5,382,657, Greenwald et al., U.S. Pat. No. 5,738,846, Nieforth et al., *Clin. Pharmacol. Ther.* 59:636 (1996), Monkarsh et al., *Anal. Biochem.* 247:434 (1997)). This method can be employed for making zB7R1-comprising homodimeric, heterodimeric or multimeric soluble receptor conjugates.

The present invention contemplates compositions comprising a peptide or polypeptide, such as a soluble receptor or antibody described herein. Such compositions can further comprise a carrier. The carrier can be a conventional organic or inorganic carrier. Examples of carriers include water, buffer solution, alcohol, propylene glycol, macrogol, sesame oil, corn oil, and the like.

8. Isolation of zB7R1 or CD155 Polypeptides

The polypeptides of the present invention can be purified to at least about 80% purity, to at least about 90% purity, to at least about 95% purity, or greater than 95%, such as 96%, 97%, 98%, or greater than 99% purity with respect to contaminating macromolecules, particularly other proteins and nucleic acids, and free of infectious and pyrogenic agents. The polypeptides of the present invention may also be purified to a pharmaceutically pure state, which is greater than 99.9% pure. In certain preparations, purified polypeptide is substantially free of other polypeptides, particularly other polypeptides of animal origin.

Fractionation and/or conventional purification methods can be used to obtain preparations of zB7R1 (or CD155) purified from natural sources (e.g., human tissue sources), synthetic zB7R1 polypeptides, and recombinant zB7R1 polypeptides and fusion zB7R1 polypeptides purified from recombinant host cells. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are suitable. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Selection of a particular method for polypeptide isolation and purification is a matter of routine design and is determined in part by the properties of the chosen support. See, for example, *Affinity Chromatography: Principles & Methods* (Pharmacia LKB Biotechnology 1988), and Doonan, *Protein Purification Protocols* (The Humana Press 1996).

Additional variations in zB7R1 (or CD155) isolation and purification can be devised by those of skill in the art. For example, anti-zB7R1 antibodies, obtained as described below, can be used to isolate large quantities of protein by immunoaffinity purification.

The polypeptides of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1 (1985)). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (M. Deutscher, (ed.), *Meth. Enzymol.* 182:529 (1990)). Within additional embodiments of the invention, a fusion of the polypeptide of interest and an affinity tag (e.g., maltose-binding protein, an immunoglobulin domain) may be constructed to facilitate purification. Moreover, the counter-receptor-binding properties of zB7R1 extracellular domain can be exploited for purification, for example, of zB7R1-comprising soluble receptors; for example, by using affinity chromatography wherein the appropriate counter-receptor is bound to a column and the zB7R1-comprising receptor is bound and subsequently eluted using standard chromatography methods.

zB7R1 (or CD155) polypeptides or fragments thereof may also be prepared through chemical synthesis, as described above. zB7R1 polypeptides may be monomers or multimers; glycosylated or non-glycosylated; PEGylated or non-PEGylated; and may or may not include an initial methionine amino acid residue.

9. Production of Antibodies to zB7R1 Proteins

Antibodies to zB7R1 can be obtained, for example, using the product of a zB7R1 expression vector or zB7R1 isolated from a natural source as an antigen. Particularly useful anti-zB7R1 antibodies "bind specifically" with zB7R1. Antibodies are considered to be specifically binding if the antibodies exhibit at least one of the following two properties: (1) antibodies bind to zB7R1 with a threshold level of binding activity, and (2) antibodies do not significantly cross-react with polypeptides related to zB7R1.

With regard to the first characteristic, antibodies specifically bind if they bind to a zB7R1 polypeptide, peptide or epitope with a binding affinity ($K_a$) of $10^6 M^{-1}$ or greater, preferably $10^7 M^{-1}$ or greater, more preferably $10^8 M^{-1}$ or greater, and most preferably $10^9 M^{-1}$ or greater. The binding affinity of an antibody can be readily determined by one of ordinary skill in the art, for example, by Scatchard analysis (Scatchard, *Ann. NY Acad. Sci.* 51:660 (1949)). With regard to the second characteristic, antibodies do not significantly cross-react with related polypeptide molecules, for example, if they detect zB7R1, but not presently known polypeptides using a standard Western blot analysis. Examples of known related polypeptides include known cytokine receptors.

Anti-zB7R1 antibodies can be produced using antigenic zB7R1 epitope-bearing peptides and polypeptides. Antigenic epitope-bearing peptides and polypeptides of the present invention contain a sequence of at least nine, or between 15 to about 30 amino acids contained within SEQ ID NO:2 or another amino acid sequence disclosed herein. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that bind with zB7R1. It is desirable that the amino acid sequence of the epitope-bearing peptide is selected to provide substantial solubility in aqueous solvents (i.e., the sequence includes relatively hydrophilic residues, while hydrophobic residues are typically avoided). Moreover, amino acid sequences containing proline residues may be also be desirable for antibody production.

As an illustration, potential antigenic sites in zB7R1 were identified using the Jameson-Wolf method, Jameson and Wolf, *CABIOS* 4:181, (1988), as implemented by the PROTEAN program (version 3.14) of LASERGENE (DNASTAR; Madison, Wis.). Default parameters were used in this analysis.

The Jameson-Wolf method predicts potential antigenic determinants by combining six major subroutines for protein structural prediction. Briefly, the Hopp-Woods method, Hopp et al., *Proc. Nat'l Acad. Sci. USA* 78:3824 (1981), was first used to identify amino acid sequences representing areas of greatest local hydrophilicity (parameter: seven residues averaged). In the second step, Emini's method, Emini et al., *J. Virology* 55:836 (1985), was used to calculate surface probabilities (parameter: surface decision threshold (0.6)=1). Third, the Karplus-Schultz method, Karplus and Schultz, *Naturwissenschaften* 72:212 (1985), was used to predict backbone chain flexibility (parameter: flexibility threshold (0.2)=1). In the fourth and fifth steps of the analysis, secondary structure predictions were applied to the data using the methods of Chou-Fasman, Chou, "*Prediction of Protein Structural Classes from Amino Acid Composition*," in *Prediction of Protein Structure and the Principles of Protein Conformation*, Fasman (ed.), pages 549-586 (Plenum Press 1990), and Garnier-Robson, Garnier et al., *J. Mol. Biol.* 120:97 (1978) (Chou-Fasman parameters: conformation table=64 proteins; a region threshold=103; β region threshold=105; Garnier-Robson parameters: α and β decision constants=0). In the sixth subroutine, flexibility parameters and hydropathy/solvent accessibility factors were combined to determine a surface contour value, designated as the "antigenic index." Finally, a peak broadening function was applied to the antigenic index, which broadens major surface peaks by adding 20, 40, 60, or 80% of the respective peak value to account for additional free energy derived from the mobility of surface regions relative to interior regions. This calculation was not applied, however, to any major peak that resides in a helical region, since helical regions tend to be less flexible.

The results of this analysis indicated that the following amino acid sequences of SEQ ID NO:2 would provide suitable antigenic peptides: Hopp/Woods hydrophilicity profiles can be used to determine regions that have the most antigenic potential within SEQ ID NO:3 (Hopp et al., *Proc. Natl. Acad. Sci.* 78:3824-3828, 1981; Hopp, *J. Immun. Meth.* 88:1-18, 1986 and Triquier et al., *Protein Engineering* 11:153-169, 1998). The profile is based on a sliding six-residue window. Buried G, S, and T residues and exposed H, Y, and W residues were ignored. Moreover, zB7R1 antigenic epitopes within SEQ ID NO:2 as predicted by a Jameson-Wolf plot, e.g., using DNASTAR Protean program (DNASTAR, Inc., Madison, Wis.) serve as preferred antigenic epitopes, and can be determined by one of skill in the art. Such antigenic epitopes include (1) (1) amino acid residues 80 to 86 of SEQ ID NO:2; (2) amino acid residues 163 to 170 of SEQ ID NO:2; (3) amino acid residues 163 to 190 of SEQ ID NO:2; (4) amino acid residues 175 to 190 of SEQ ID NO:2; and (5) amino acid residues 211 to 221 of SEQ ID NO:2. The present invention contemplates the use of any one of antigenic peptides 1 to 5 to generate antibodies to zB7R1 or as a tool to screen or identify neutralizing monoclonal antibodies of the present invention. The present invention contemplates the use of any antigenic peptides or epitopes described herein to generate antibodies to zB7R1, as well as to identify and screen anti-zB7R1 monoclonal antibodies that may bind, agonize, block, inhibit, reduce, increase, antagonize or neutralize the activity of a zB7R1 counter-receptor.

Polyclonal antibodies to recombinant zB7R1 protein or to zB7R1 isolated from natural sources can be prepared using methods well-known to those of skill in the art. See, for example, Green et al., "Production of Polyclonal Antisera," in *Immunochemical Protocols* (Manson, ed.), pages 1-5 (Humana Press 1992), and Williams et al., "Expression of foreign proteins in *E. coli* using plasmid vectors and purification of specific polyclonal antibodies," in *DNA Cloning 2: Expression Systems,* 2nd Edition, Glover et al. (eds.), page 15 (Oxford University Press 1995). The immunogenicity of a zB7R1 polypeptide can be increased through the use of an adjuvant, such as alum (aluminum hydroxide) or Freund's complete or incomplete adjuvant. Polypeptides useful for immunization also include fusion polypeptides, such as fusions of zB7R1 or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immunization.

Although polyclonal antibodies are typically raised in animals such as horses, cows, dogs, chicken, rats, mice, rabbits, guinea pigs, goats, or sheep, an anti-zB7R1 antibody of the present invention may also be derived from a subhuman primate antibody. General techniques for raising diagnostically and therapeutically useful antibodies in baboons may be found, for example, in Goldenberg et al., international patent publication No. WO 91/11465, and in Losman et al., *Int. J. Cancer* 46:310 (1990).

Alternatively, monoclonal anti-zB7R1 antibodies can be generated. Rodent monoclonal antibodies to specific antigens may be obtained by methods known to those skilled in the art (see, for example, Kohler et al., *Nature* 256:495 (1975), Coligan et al. (eds.), *Current Protocols in Immunology, Vol. 1, pages* 2.5.1-2.6.7 (John Wiley & Sons 1991) ["Coligan"], Picksley et al., "Production of monoclonal antibodies against proteins expressed in *E. coli*," in *DNA Cloning 2: Expression Systems,* 2nd Edition, Glover et al. (eds.), page 93 (Oxford University Press 1995)).

Briefly, monoclonal antibodies can be obtained by injecting mice with a composition comprising a zB7R1 gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an anti-zB7R1 antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13 (1994), Lonberg et al., *Nature* 368:856 (1994), and Taylor et al., *Int. Immun.* 6:579 (1994).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology*, Vol. 10, pages 79-104 (The Humana Press, Inc. 1992)).

For particular uses, it may be desirable to prepare fragments of anti-zB7R1 antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230 (1960), Porter, *Biochem. J.* 73:119 (1959), Edelman et al., in *Methods in Enzymology* Vol. 1, page 422 (Academic Press 1967), and by Coligan at pages 2.8.1-2.8.10 and 2.10.-2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Nat'l Acad. Sci. USA* 69:2659 (1972). Alternatively, the variable chains can be linked by an intermolecular disulfide bond or cross-linked by chemicals such as glutaraldehyde (see, for example, Sandhu, *Crit. Rev. Biotech.* 12:437 (1992)).

The Fv fragments may comprise $V_H$ and $V_L$ chains which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing scFvs are described, for example, by Whitlow et al., *Methods: A Companion to Methods in Enzymology* 2:97 (1991) (also see, Bird et al., *Science* 242:423 (1988), Ladner et al., U.S. Pat. No. 4,946,778, Pack et al., *Bio/Technology* 11:1271 (1993), and Sandhu, supra).

As an illustration, a scFV can be obtained by exposing lymphocytes to zB7R1 polypeptide in vitro, and selecting antibody display libraries in phage or similar vectors (for instance, through use of immobilized or labeled zB7R1 protein or peptide). Genes encoding polypeptides having potential zB7R1 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a counter-receptor or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., *Phage Display of Peptides and Proteins* (Academic Press, Inc. 1996)) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the zB7R1 sequences disclosed herein to identify proteins which bind to zB7R1.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106 (1991), Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995), and Ward et al., "Genetic Manipulation and Expression of Antibodies," in *Monoclonal Antibodies: Principles and Applications*, Birch et al., (eds.), page 137 (Wiley-Liss, Inc. 1995)).

Alternatively, an anti-zB7R1 antibody may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833 (1989). Techniques for producing humanized monoclonal antibodies are described, for example, by Jones et al., *Nature* 321:522 (1986), Carter et al., *Proc. Nat'l Acad. Sci. USA* 89:4285 (1992), Sandhu, *Crit. Rev. Biotech.* 12:437 (1992), Singer et al., *J. Immun.* 150:2844 (1993), Sudhir (ed.), *Antibody Engineering Protocols* (Humana Press, Inc. 1995), Kelley, "Engineering Therapeutic Antibodies," in *Protein Engineering: Principles and Practice*, Cleland et al. (eds.), pages 399-434 (John Wiley & Sons, Inc. 1996), and by Queen et al., U.S. Pat. No. 5,693,762 (1997).

Moreover, anti-zB7R1 antibodies or antibody fragments of the present invention can be PEGylated using methods in the art and described herein.

Polyclonal anti-idiotype antibodies can be prepared by immunizing animals with anti-zB7R1 antibodies or antibody fragments, using standard techniques. See, for example, Green et al., "Production of Polyclonal Antisera," in *Methods In Molecular Biology: Immunochemical Protocols*, Manson (ed.), pages 1-12 (Humana Press 1992). Also, see Coligan at pages 2.4.1-2.4.7. Alternatively, monoclonal anti-idiotype antibodies can be prepared using anti-zB7R1 antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, *J. Gen. Virol.* 77:1875 (1996).

An anti-zB7R1 antibody can be conjugated with a detectable label to form an anti-zB7R1 immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^3H$, $^{125}I$, $^{131}I$, $^{35}S$, and $^{14}C$.

Anti-zB7R1 immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-zB7R1 immunoconjugates can be detectably labeled by coupling an antibody component to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-zB7R1 immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-zB7R1 immunoconjugates can be detectably labeled by linking an anti-zB7R1 antibody component to an enzyme. When the anti-zB7R1-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to anti-zB7R1 antibodies can be accomplished using standard techniques known to the art. Typical methodology in this regard is described by Kennedy et al., *Clin. Chim. Acta* 70:1 (1976), Schurs et al., *Clin. Chim. Acta* 81:1 (1977), Shih et al., *Int'l J. Cancer* 46:1101 (1990), Stein et al., *Cancer Res.* 50:1330 (1990), and Coligan, supra.

Moreover, the convenience and versatility of immunochemical detection can be enhanced by using anti-zB7R1 antibodies that have been conjugated with avidin, streptavidin, and biotin (see, for example, Wilchek et al. (eds.), "Avidin-Biotin Technology," *Methods In Enzymology*, Vol. 184 (Academic Press 1990), and Bayer et al., "Immunochemical Applications of Avidin-Biotin Technology," in *Methods In Molecular Biology*, Vol. 10, Manson (ed.), pages 149-162 (The Humana Press, Inc. 1992).

Methods for performing immunoassays are well-established. See, for example, Cook and Self, "Monoclonal Antibodies in Diagnostic Immunoassays," in *Monoclonal Antibodies: Production, Engineering, and Clinical Application*, Ritter and Ladyman (eds.), pages 180-208, (Cambridge University Press, 1995), Perry, "The Role of Monoclonal Antibodies in the Advancement of Immunoassay Technology," in *Monoclonal Antibodies: Principles and Applications*, Birch and Lennox (eds.), pages 107-120 (Wiley-Liss, Inc. 1995), and Diamandis, *Immunoassay* (Academic Press, Inc. 1996).

The present invention also contemplates kits for performing an immunological diagnostic assay for zB7R1 gene expression. Such kits comprise at least one container comprising an anti-zB7R1 antibody, or antibody fragment. A kit may also comprise a second container comprising one or more reagents capable of indicating the presence of zB7R1 antibody or antibody fragments. Examples of such indicator reagents include detectable labels such as a radioactive label, a fluorescent label, a chemiluminescent label, an enzyme label, a bioluminescent label, colloidal gold, and the like. A kit may also comprise a means for conveying to the user that zB7R1 antibodies or antibody fragments are used to detect zB7R1 protein. For example, written instructions may state that the enclosed antibody or antibody fragment can be used to detect zB7R1. The written material can be applied directly to a container, or the written material can be provided in the form of a packaging insert.

10. Use of Anti-zB7R1 Antibodies to Agonize or Antagonize zB7R1 Binding to its Counter-Receptor Alternative techniques for generating or selecting antibodies useful herein include in vitro exposure of lymphocytes to soluble zB7R1 receptor polypeptides or fragments thereof, such as antigenic epitopes, and selection of antibody display libraries in phage or similar vectors (for instance, through use of immobilized or labeled soluble zB7R1 receptor polypeptides or fragments thereof, such as antigenic epitopes). Genes encoding polypeptides having potential binding domains such as soluble zB7R1 receptor polypeptides or fragments thereof, such as antigenic epitopes can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides that interact with a known target that can be a protein or polypeptide, such as a counter-receptor (i.e. CD155) or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571, 698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the soluble zB7R1 receptor polypeptides or fragments thereof, such as antigenic epitope polypeptide sequences disclosed herein to identify proteins which bind to zB7R1-comprising receptor polypeptides. These "binding polypeptides," which interact with soluble zB7R1-comprising receptor polypeptides, can be used for tagging cells; for isolating homolog polypeptides by affinity purification; they can be directly or indirectly conjugated to drugs, toxins, radionuclides and the like. These binding polypeptides can also be used in analytical methods such as for screening expression libraries and for agonizing and/or neutralizing activity, e.g., for binding, blocking, inhibiting, reducing, antagonizing or neutralizing interaction between zB7R1 and its counter-receptor. The binding polypeptides can also be used for diagnostic assays for determining circulating levels of soluble zB7R1-comprising receptor polypeptides; for detecting or quantitating soluble or non-soluble zB7R1-comprising receptors as marker of underlying pathology or disease. These binding polypeptides can also act as "antagonists" to block or inhibit soluble or membrane-bound zB7R1 monomeric receptor or zB7R1 homodimeric, heterodimeric or multimeric polypeptide binding (e.g. to counter-receptor) and signal transduction in vitro and in vivo. Again, these binding polypeptides serve as anti-zB7R1 monomeric receptor or anti-zB7R1 homodimeric, heterodimeric or multimeric polypeptides and are useful for inhibiting zB7R1 activity, as well as zB7R1 counter-receptor activity or protein-binding. Antibodies raised to the natural receptor complexes of the present invention, and zB7R1-epitope-binding antibodies, and anti-zB7R1 neutralizing monoclonal antibodies may be preferred embodiments, as they may act more specifically against the zB7R1 and can inhibit its binding to its counter-receptor. Moreover, the agonistic, antagonistic and binding activity of the antibodies of the present invention can be assayed in a zB7R1 proliferation, signal trap, luciferase or binding assays in the presence of its counter-receptor or any other B7 family receptor, and zB7R1-comprising soluble receptors, and other biological or biochemical assays described herein.

Antibodies to zB7R1 receptor polypeptides (e.g., antibodies to SEQ ID NO:2 or 5) or fragments thereof, such as antigenic epitopes may be used for inhibiting the inflammatory effects of zB7R1 in vivo, for therapeutic use against rheumatoid arthritis, psoriasis, atopic dermatitis, inflammatory skin conditions, endotoxemia, arthritis, asthma, IBD, colitis, psoriatic arthritis or other B7-induced inflammatory conditions; tagging cells that express zB7R1 receptors; for isolating soluble zB7R1-comprising receptor polypeptides by affinity purification; for diagnostic assays for determining circulating levels of soluble zB7R1-comprising receptor polypeptides; for detecting or quantitating soluble zB7R1-comprising receptors as marker of underlying pathology or disease; in analytical methods employing FACS; for screening expression libraries; for generating anti-idiotypic antibodies that can act as zB7R1 agonists; and as neutralizing antibodies or as antagonists to bind, block, inhibit, reduce, or antagonize zB7R1 receptor function, or to bind, block, inhibit, reduce, antagonize or neutralize zB7R1 activity in vitro and in vivo. Suitable direct tags or labels include radionuclides, enzymes, substrates, cofactors, biotin, inhibitors, fluorescent markers, chemiluminescent markers, magnetic particles and the like; indirect tags or labels may feature use of biotin-avidin or other complement/anticomplement pairs as intermediates. Antibodies herein may also be directly or indirectly conjugated to drugs, toxins, radionuclides and the like, and these conjugates used for in vivo diagnostic or therapeutic applications. Moreover, antibodies to soluble zB7R1-comprising receptor polypeptides, or fragments thereof may be used in vitro to detect denatured or non-denatured zB7R1-comprising receptor polypeptides or fragments thereof in assays, for example, Western Blots or other assays known in the art.

Antibodies to soluble zB7R1 receptor or soluble zB7R1 homodimeric, heterodimeric or multimeric receptor polypeptides are useful for tagging cells that express the corresponding receptors and assaying their expression levels, for affinity purification, within diagnostic assays for determining circulating levels of receptor polypeptides, analytical methods employing fluorescence-activated cell sorting. Moreover, divalent antibodies, and anti-idiotypic antibodies may be used as agonists to mimic the effect of zB7R1.

Antibodies herein can also be directly or indirectly conjugated to drugs, toxins, radionuclides and the like, and these conjugates used for in vivo diagnostic or therapeutic applications. For instance, antibodies or binding polypeptides which recognize soluble zB7R1 receptor or soluble zB7R1 homodimeric, heterodimeric or multimeric receptor polypeptides can be used to identify or treat tissues or organs that express a corresponding anti-complementary molecule (i.e., a zB7R1-comprising soluble or membrane-bound receptor). More specifically, antibodies to soluble zB7R1-comprising receptor polypeptides, or bioactive fragments or portions thereof, can be coupled to detectable or cytotoxic molecules and delivered to a mammal having cells, tissues or organs that express the zB7R1-comprising receptor such as zB7R1-expressing cancers.

Suitable detectable molecules may be directly or indirectly attached to polypeptides that bind zB7R1-comprising receptor polypeptides, such as "binding polypeptides," (including binding peptides disclosed above), antibodies, or bioactive fragments or portions thereof. Suitable detectable molecules include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Binding polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the binding polypeptide or antibody portion. For these purposes, biotin/streptavidin is an exemplary complementary/anticomplementary pair.

In another embodiment, binding polypeptide-toxin fusion proteins or antibody-toxin fusion proteins can be used for targeted cell or tissue inhibition or ablation (for instance, to treat cancer cells or tissues). Alternatively, if the binding polypeptide has multiple functional domains (i.e., an activation domain or a counter-receptor binding domain, plus a targeting domain), a fusion protein including only the targeting domain may be suitable for directing a detectable molecule, a cytotoxic molecule or a complementary molecule to a cell or tissue type of interest. In instances where the fusion protein including only a single domain includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates.

Alternatively, zB7R1 receptor binding polypeptides or antibody fusion proteins described herein can be used for enhancing in vivo killing of target tissues by directly stimulating a zB7R1 receptor-modulated apoptotic pathway, resulting in cell death of hyperproliferative cells expressing zB7R1-comprising receptors.

11. Therapeutic Uses of Polypeptides Having zB7R1 Activity or Antibodies to zB7R1

Amino acid sequences having soluble zB7R1 activity can be used to modulate the immune system by binding zB7R1 counter-receptors such as CD155, and thus, preventing the binding of zB7R1 counter-receptor with endogenous zB7R1 receptor. zB7R1 antagonists, such as anti-zB7R1 antibodies, can also be used to modulate the immune system by inhibiting the binding of zB7R1 counter-receptor with the endogenous zB7R1 receptor. Accordingly, the present invention includes the use of proteins, polypeptides, and peptides having zB7R1 activity (such as soluble zB7R1 polypeptides, zB7R1 polypeptide fragments, zB7R1 analogs (e.g., anti-zB7R1 anti-idiotype antibodies), and zB7R1 fusion proteins) to a subject which lacks an adequate amount of this polypeptide, or which produces an excess of zB7R1 counter-receptor. zB7R1 antagonists (e.g., anti-zB7R1 antibodies) can be also used to treat a subject which produces an excess of either zB7R1 counter-receptor or zB7R1. Suitable subjects include mammals, such as humans. For example, such zB7R1 polypeptides and anti-zB7R1 antibodies are useful in binding, blocking, inhibiting, reducing, antagonizing or neutralizing zB7R1 and CD155 (either singly or together), in the treatment of psoriasis, atopic dermatitis, inflammatory skin conditions, psoriatic arthritis, arthritis, endotoxemia, asthma, inflammatory bowel disease (IBD), colitis, and other inflammatory conditions disclosed herein.

zB7R1 may be involved in the pathology of psoriasis. The present invention is in particular a method for treating psoriasis by administering agents that bind, block, inhibit, reduce, antagonize or neutralize zB7R1. The agonists to zB7R1 can either be a soluble receptor that binds to zB7R1, or antibodies, single chain antibodies or fragments of antibodies that bind to either zB7R1 or the zB7R1 counter-receptor, e.g., anti-zB7R1 antibodies. The antagonists will thus prevent activation of the zB7R1 receptor.

Psoriasis is one of the most common dermatologic diseases, affecting up to 1 to 2 percent of the world's population. It is a chronic inflammatory skin disorder characterized by erythematous, sharply demarcated papules and rounded plaques, covered by silvery micaceous scale. The skin lesions of psoriasis are variably pruritic. Traumatized areas often develop lesions of psoriasis. Additionally, other external factors may exacerbate psoriasis including infections, stress, and medications, e.g. lithium, beta blockers, and anti-malarials.

The most common variety of psoriasis is called plaque type. Patients with plaque-type psoriasis will have stable, slowly growing plaques, which remain basically unchanged for long periods of time. The most common areas for plaque psoriasis to occur are the elbows knees, gluteal cleft, and the scalp. Involvement tends to be symmetrical. Inverse psoriasis affects the intertriginous regions including the axilla, groin, submammary region, and navel, and it also tends to affect the scalp, palms, and soles. The individual lesions are sharply demarcated plaques but may be moist due to their location. Plaque-type psoriasis generally develops slowly and runs an indolent course. It rarely spontaneously remits.

Eruptive psoriasis (guttate psoriasis) is most common in children and young adults. It develops acutely in individuals without psoriasis or in those with chronic plaque psoriasis. Patients present with many small erythematous, scaling papules, frequently after upper respiratory tract infection with beta-hemolytic streptococci. Patients with psoriasis may also develop pustular lesions. These may be localized to the palms and soles or may be generalized and associated with fever, malaise, diarrhea, and arthralgias.

About half of all patients with psoriasis have fingernail involvement, appearing as punctate pitting, nail thickening or subungual hyperkeratosis. About 5 to 10 percent of patients with psoriasis have associated joint complaints, and these are most often found in patients with fingernail involvement. Although some have the coincident occurrence of classic Although some have the coincident occurrence of classic rheumatoid arthritis, many have joint disease that falls into one of five type associated with psoriasis: (1) disease limited to a single or a few small joints (70 percent of cases); (2) a seronegative rheumatoid arthritis-like disease; (3) involvement of the distal interphalangeal joints; (4) severe destructive arthritis with the development of "arthritis mutilans"; and (5) disease limited to the spine.

Psoriasis can be treated by administering agents that act as zB7R1 agonists. The preferred antagonists are either a soluble receptor to zB7R1 such as zB7R1 (SEQ ID NO:3) or antibodies, antibody fragments or single chain antibodies that bind to the zB7R1 or itys counter-receptor. Such antagonists can be administered alone or in combination with other established therapies such as lubricants, keratolytics, topical corticosteroids, topical vitamin D derivatives, anthralin, systemic antimetabolites such as methotrexate, psoralen-ultraviolet-light therapy (PUVA), etretinate, isotretinoin, cyclosporine, and the topical vitamin D3 derivative calcipotriol. Moreover, such antagonists can be administered to individual subcutaneously, intravenously, or transdermally using a cream or transdermal patch that contains the antagonist. If administered subcutaneously, the antagonist can be injected into one or more psoriatic plaques. If administered transdermally, the antagonists can be administered directly on the plaques using a cream, ointment, salve, or solution containing the antagonist.

Agonists to zB7R1 can be administered to a person who has asthma, bronchitis or cystic fibrosis or other inflammatory lung disease to treat the disease. The antagonists can be administered by any suitable method including intravenous, subcutaneous, bronchial lavage, and the use of inhalant containing the antagonist.

Thus, particular embodiments of the present invention are directed toward use of soluble zB7R1 and anti-zB7R1 antibodies as agonists in inflammatory and immune diseases or conditions such as psoriasis, psoriatic arthritis, atopic dermatitis, inflammatory skin conditions, rheumatoid arthritis, inflammatory bowel disease (IBD), Crohn's Disease, diverticulosis, asthma, pancreatitis, type I diabetes (IDDM), pancreatic cancer, pancreatitis, Graves Disease, colon and intestinal cancer, autoimmune disease, sepsis, organ or bone marrow transplant; inflammation due to endotoxemia, trauma, surgery or infection; amyloidosis; splenomegaly; graft versus host disease; and where inhibition of inflammation, immune suppression, reduction of proliferation of hematopoietic, immune, inflammatory or lymphoid cells, macrophages, T-cells (including Th1 and Th2 cells), suppression of immune response to a pathogen or antigen, or other instances where inhibition of zB7R1 is desired.

Moreover, antibodies or binding polypeptides that bind zB7R1 polypeptides described herein, and zB7R1 polypeptides themselves are useful to:

Block, inhibit, reduce, antagonize or neutralize signaling via zB7R1 in the treatment of acute inflammation, inflammation as a result of trauma, tissue injury, surgery, sepsis or infection, and chronic inflammatory diseases such as asthma, inflammatory bowel disease (IBD), chronic colitis, splenomegaly, rheumatoid arthritis, recurrent acute inflammatory episodes (e.g., tuberculosis), and treatment of amyloidosis, and atherosclerosis, Castleman's Disease, asthma, and other diseases associated with the induction of acute-phase response.

Block, inhibit, reduce, antagonize or neutralize signaling via zB7R1 in the treatment of autoimmune diseases such as IDDM, multiple sclerosis (MS), systemic Lupus erythematosus (SLE), myasthenia gravis, rheumatoid arthritis, and IBD to prevent or inhibit signaling in immune cells (e.g. lymphocytes, monocytes, leukocytes) via zB7R1 (Hughes C et al., *J. Immunol* 153: 3319-3325, 1994). Alternatively antibodies, such as monoclonal antibodies (MAb) to zB7R1, can also be used as an antagonist to deplete unwanted immune cells to treat autoimmune disease. Asthma, allergy and other atopic disease may be treated with an MAb against, for example, soluble zB7R1 soluble receptors to inhibit the immune response or to deplete offending cells. Blocking, inhibiting, reducing, or antagonizing signaling via zB7R1, using the polypeptides and antibodies of the present invention, may also benefit diseases of the pancreas, kidney, pituitary and neuronal cells. IDDM, NIDDM, pancreatitis, and pancreatic carcinoma may benefit. zB7R1 may serve as a target for MAb therapy of cancer where an antagonizing MAb inhibits cancer growth and targets immune-mediated killing. (Holliger P, and Hoogenboom, H: *Nature Biotech.* 16: 1015-1016, 1998). Mabs to soluble zB7R1 may also be useful to treat nephropathies such as glomerulosclerosis, membranous neuropathy, amyloidosis (which also affects the kidney among other tissues), renal arteriosclerosis, glomerulonephritis of various origins, fibroproliferative diseases of the kidney, as well as kidney dysfunction associated with SLE, IDDM, type II diabetes (NIDDM), renal tumors and other diseases.

Agonize, enhance, increase or initiate signaling via zB7R1 in the treatment of autoimmune diseases such as IDDM, MS, SLE, myasthenia gravis, rheumatoid arthritis, and IBD. Anti-zB7R1 neutralizing and monoclonal antibodies may signal lymphocytes or other immune cells to differentiate, alter proliferation, or change production of cytokines or cell surface proteins that ameliorate autoimmunity. Specifically, modulation of a T-cell response may deviate an autoimmune response to ameliorate disease (Smith J A et al., *J. Immunol.* 160:4841-4849, 1998). Similarly, agonistic anti-zB7R1 monoclonal antibodies may be used to signal, deplete and deviate immune cells involved in rheumatoid arthritis, asthma, allergy and atopoic disease. Signaling via zB7R1 may also benefit diseases of the pancreas, kidney, pituitary and neuronal cells. IDDM, NIDDM, pancreatitis, and pancreatic carcinoma may benefit. zB7R1 may serve as a target for MAb therapy of pancreatic cancer where a signaling MAb inhibits cancer growth and targets immune-mediated killing (Tutt, A L et al., *J Immunol.* 161: 3175-3185, 1998). Similarly renal cell carcinoma may be treated with monoclonal antibodies to zB7R1-comprising soluble receptors of the present invention.

Soluble zB7R1 polypeptides described herein can be used to bind, block, inhibit, reduce, antagonize or neutralize zB7R1 activity, either singly or together, in the treatment of autoimmune disease, atopic disease, NIDDM, pancreatitis and kidney dysfunction as described above. A soluble form of zB7R1 may be used to promote an antibody response mediated by Th cells and/or to promote the production of IL-4 or other cytokines by lymphocytes or other immune cells.

Moreover, inflammation is a protective response by an organism to fend off an invading agent. Inflammation is a cascading event that involves many cellular and humoral mediators. On one hand, suppression of inflammatory responses can leave a host immunocompromised; however, if left unchecked, inflammation can lead to serious complications including chronic inflammatory diseases (e.g., psoriasis, arthritis, rheumatoid arthritis, multiple sclerosis, inflammatory bowel disease and the like), septic shock and multiple organ failure. Importantly, these diverse disease states share common inflammatory mediators. The collective diseases that are characterized by inflammation have a large impact on human morbidity and mortality. Therefore it is clear that molecules that are intimately involved in the costimulation and/or inhibition of immune responses, such as zB7R1, its counter-receptor, and anti-zB7R1 antibodies, could have crucial therapeutic potential for a vast number of human and animal diseases, from asthma and allergy to autoimmunity and septic shock.

1. Arthritis

Arthritis, including osteoarthritis, rheumatoid arthritis, arthritic joints as a result of injury, and the like, are common inflammatory conditions which would benefit from the therapeutic use of anti-inflammatory proteins, such as the zB7R1 molecules of the present invention. For example, rheumatoid arthritis (RA) is a systemic disease that affects the entire body and is one of the most common forms of arthritis. It is characterized by the inflammation of the membrane lining the joint, which causes pain, stiffness, warmth, redness and swelling. Inflammatory cells release enzymes that may digest bone and cartilage. As a result of rheumatoid arthritis, the inflamed joint lining, the synovium, can invade and damage bone and cartilage leading to joint deterioration and severe pain amongst other physiologic effects. The involved joint can lose its shape and alignment, resulting in pain and loss of movement.

Rheumatoid arthritis (RA) is an immune-mediated disease particularly characterized by inflammation and subsequent tissue damage leading to severe disability and increased mortality. A variety of cytokines are produced locally in the rheumatoid joints. Numerous studies have demonstrated that IL-1 and TNF-alpha, two prototypic pro-inflammatory cytokines, play an important role in the mechanisms involved in synovial inflammation and in progressive joint destruction. Indeed, the administration of TNF-alpha and IL-1 inhibitors in patients with RA has led to a dramatic improvement of clinical and biological signs of inflammation and a reduction of radiological signs of bone erosion and cartilage destruction. However, despite these encouraging results, a significant percentage of patients do not respond to these agents, suggesting that other mediators are also involved in the pathophysiology of arthritis (Gabay, *Expert. Opin. Biol. Ther.* 2(2):135-149, 2002). One of those mediators could be a soluble zB7R1 protein or an anti-zB7R1 antibody and as such a molecule that binds or mediates zB7R1, such as soluble B7R1-Fc, B7R1m-VASP CH6 or antibodies or binding partners as described herein, could serve as a valuable therapeutic to reduce inflammation in rheumatoid arthritis, and other arthritic diseases.

There are several animal models for rheumatoid arthritis known in the art. For example, in the collagen-induced arthritis (CIA) model, mice develop chronic inflammatory arthritis that closely resembles human rheumatoid arthritis. Since CIA shares similar immunological and pathological features with RA, this makes it an ideal model for screening potential human anti-inflammatory compounds. The CIA model is a well-known model in mice that depends on both an immune response, and an inflammatory response, in order to occur. The immune response comprises the interaction of B-cells and CD4+ T-cells in response to collagen, which is given as antigen, and leads to the production of anti-collagen antibodies. The inflammatory phase is the result of tissue responses from mediators of inflammation, as a consequence of some of these antibodies cross-reacting to the mouse's native collagen and activating the complement cascade. An advantage in using the CIA model is that the basic mechanisms of pathogenesis are known. The relevant T-cell and B-cell epitopes on type II collagen have been identified, and various immunological (e.g., delayed-type hypersensitivity and anti-collagen antibody) and inflammatory (e.g., cytokines, chemokines, and matrix-degrading enzymes) parameters relating to immune-mediated arthritis have been determined, and can thus be used to assess test compound efficacy in the CIA model (Wooley, *Curr. Opin. Rheum.* 3:407-20, 1999; Williams et al., *Immunol.* 89:9784-788, 1992; Myers et al., Life Sci. 61:1861-78, 1997; and Wang et al., *Immunol.* 92:8955-959, 1995).

As shown in Example 21, mRNA levels of murine B7R1 are higher in the affected paws and draining (popliteal) lymph nodes from mice with CIA compared to mice without CIA, and the levels are associated with disease severity. Furthermore, one group has shown that the delivery of a neutralizing antibody to another B7 family member, B7 homologous protein (B7h), reduces symptoms in a mouse CIA-model relative to control mice (Iwai et al, *J. Immunol.* 169:4332, 2002), thus supporting the idea that soluble B7R1-Fc and B7R1m-VASP CH6 may be beneficial in treating human disease, such as arthritis. The administration of a neutralizing anti-B7h antibody reduced the symptoms of arthritis in the animals when introduced prophylactically or after symptoms of arthritis were already present in the model (Iwai et al, *J. Immunol.* 169:4332, 2002). Therefore, B7R1-Fc or B7R1m-VASP CH6 can be used to treat of specific human diseases such as cancer, rheumatoid arthritis, psoriasis, psoriatic arthritis, arthritis, endotoxemia, inflammatory bowel disease (IBD), colitis, and other inflammatory conditions disclosed herein.

The administration of soluble B7R1 comprising polypeptides, such as B7R1-Fc or B7R1m-VASP CH6 or other zB7R1 soluble and fusion proteins to these CIA model mice is used to evaluate the use of soluble B7R1-Fc to ameliorate symptoms and alter the course of disease. Furthermore, since inflammation is implicated in the pathogenesis and progression of rheumatoid arthritis, the systemic or local administration of soluble B7R1 comprising polypeptides, such as B7R1-Fc, B7R1m-VASP CH6 or other soluble receptors and anti-zB7R1 antibodies, and fusion proteins can potentially suppress the inflammatory response in RA. By way of example and without limitation, the injection of 10-200 μg B7R1-Fc or B7R1m-VASP CH6 per mouse (one to seven times a week for up to but not limited to 4 weeks via s.c., i.p., or i.m route of administration) can significantly reduce the disease score (paw score, incident of inflammation, or disease). Depending on the initiation of B7R1-Fc administration (e.g. prior to or at the time of collagen immunization, or at any time point following the second collagen immunization, including those time points at which the disease has already progressed), B7R1-Fc or B7R1m-VASP CH6 can be efficacious in preventing rheumatoid arthritis, as well as preventing its progression. Other potential therapeutics include CD155 polypeptides or anti-CD155 antibodies.

2. Endotoxemia

Endotoxemia is a severe condition commonly resulting from infectious agents such as bacteria and other infectious disease agents, sepsis, toxic shock syndrome, or in immunocompromised patients subjected to opportunistic infections, and the like. Therapeutically useful of anti-inflammatory proteins, such as zB7R1 polypeptides and antibodies of the present invention, could aid in preventing and treating endotoxemia in humans and animals. zB7R1 polypeptides, anti-IL22RA antibodies, or anti IL-22 antibodies or binding partners, could serve as a valuable therapeutic to reduce inflammation and pathological effects in endotoxemia.

Lipopolysaccharide (LPS) induced endotoxemia engages many of the proinflammatory mediators that produce pathological effects in the infectious diseases and LPS induced endotoxemia in rodents is a widely used and acceptable model for studying the pharmacological effects of potential pro-inflammatory or immunomodulating agents. LPS, produced in gram-negative bacteria, is a major causative agent in the pathogenesis of septic shock (Glausner et al., *Lancet* 338:732, 1991). A shock-like state can indeed be induced experimentally by a single injection of LPS into animals. Molecules produced by cells responding to LPS can target pathogens directly or indirectly. Although these biological responses protect the host against invading pathogens, they may also cause harm. Thus, massive stimulation of innate immunity, occurring as a result of severe Gram-negative bacterial infection, leads to excess production of cytokines and other molecules, and the development of a fatal syndrome, septic shock syndrome, which is characterized by fever, hypotension, disseminated intravascular coagulation, and multiple organ failure (Dumitru et al. *Cell* 103:1071-1083, 2000).

These toxic effects of LPS are mostly related to macrophage activation leading to the release of multiple inflammatory mediators. Among these mediators, TNF appears to play a crucial role, as indicated by the prevention of LPS toxicity by the administration of neutralizing anti-TNF antibodies (Beutler et al., *Science* 229:869, 1985). It is well established that 1 ug injection of *E. coli* LPS into a C57Bl/6 mouse will result in significant increases in circulating IL-6, TNF-alpha, IL-1, and acute phase proteins (for example, SAA) approximately 2 hours post injection. The toxicity of LPS appears to be mediated by these cytokines as passive immunization against these mediators can result in decreased mortality (Beutler et al., *Science* 229:869, 1985). The potential immunointervention strategies for the prevention and/or treatment of septic shock include anti-TNF mAb, IL-1 receptor antagonist, LIF, IL-10, and G-CSF.

The administration of anti-zB7R1 antibodies or other zB7R1 soluble and fusion proteins to these LPS-induced model can be used to evaluate the use of zB7R1 to ameliorate symptoms and alter the course of LPS-induced disease.

3 Inflammatory Bowel Disease. IBD

In the United States approximately 500,000 people suffer from Inflammatory Bowel Disease (IBD) which can affect either colon and rectum (Ulcerative colitis) or both, small and large intestine (Crohn's Disease). The pathogenesis of these diseases is unclear, but they involve chronic inflammation of the affected tissues. zB7R1 polypeptides, anti-zB7R1 antibodies, or binding partners, could serve as a valuable therapeutic to reduce inflammation and pathological effects in IBD and related diseases.

Ulcerative colitis (UC) is an inflammatory disease of the large intestine, commonly called the colon, characterized by inflammation and ulceration of the mucosa or innermost lining of the colon. This inflammation causes the colon to empty frequently, resulting in diarrhea. Symptoms include loosening of the stool and associated abdominal cramping, fever and weight loss. Although the exact cause of UC is unknown, recent research suggests that the body's natural defenses are operating against proteins in the body which the body thinks are foreign (an "autoimmune reaction"). Perhaps because they resemble bacterial proteins in the gut, these proteins may either instigate or stimulate the inflammatory process that begins to destroy the lining of the colon. As the lining of the colon is destroyed, ulcers form releasing mucus, pus and blood. The disease usually begins in the rectal area and may eventually extend through the entire large bowel. Repeated episodes of inflammation lead to thickening of the wall of the intestine and rectum with scar tissue. Death of colon tissue or sepsis may occur with severe disease. The symptoms of ulcerative colitis vary in severity and their onset may be gradual or sudden. Attacks may be provoked by many factors, including respiratory infections or stress.

Although there is currently no cure for UC available, treatments are focused on suppressing the abnormal inflammatory process in the colon lining. Treatments including corticosteroids immunosuppressives (eg. azathioprine, mercaptopurine, and methotrexate) and aminosalicytates are available to treat the disease. However, the long-term use of immunosuppressives such as corticosteroids and azathioprine can result in serious side effects including thinning of bones, cataracts, infection, and liver and bone marrow effects. In the patients in whom current therapies are not successful, surgery is an option. The surgery involves the removal of the entire colon and the rectum.

There are several animal models that can partially mimic chronic ulcerative colitis. The most widely used model is the 2,4,6-trinitrobenesulfonic acid/ethanol (TNBS) induced colitis model, which induces chronic inflammation and ulceration in the colon. When TNBS is introduced into the colon of susceptible mice via intra-rectal instillation, it induces T-cell mediated immune response in the colonic mucosa, in this case leading to a massive mucosal inflammation characterized by the dense infiltration of T-cells and macrophages throughout the entire wall of the large bowel. Moreover, this histopathologic picture is accompanies by the clinical picture of progressive weight loss (wasting), bloody diarrhea, rectal prolapse, and large bowel wall thickening (Neurath et al. *Intern. Rev. Immunol.* 19:51-62, 2000).

Another colitis model uses dextran sulfate sodium (DSS), which induces an acute colitis manifested by bloody diarrhea, weight loss, shortening of the colon and mucosal ulceration with neutrophil infiltration. DSS-induced colitis is characterized histologically by infiltration of inflammatory cells into the lamina propria, with lymphoid hyperplasia, focal crypt damage, and epithelial ulceration. These changes are thought to develop due to a toxic effect of DSS on the epithelium and by phagocytosis of lamina propria cells and production of TNF-alpha and IFN-gamma. Despite its common use, several issues regarding the mechanisms of DSS about the relevance to the human disease remain unresolved. DSS is regarded as a T cell-independent model because it is observed in T cell-deficient animals such as SCID mice.

The administration of anti-zB7R1 antibodies or other zB7R1 soluble and fusion proteins to these TNBS or DSS models can be used to evaluate the use of zB7R1 to ameliorate symptoms and alter the course of gastrointestinal disease. Moreover, the results showing inhibition of T cell signaling by zB7R1 provide proof of concept that other zB7R1 antagonists, such as zB7R1 or antibodies thereto, can also be used to ameliorate symptoms in the colitis/IBD models and alter the course of disease.

4. Psoriasis

Psoriasis is a chronic skin condition that affects more than seven million Americans. Psoriasis occurs when new skin cells grow abnormally, resulting in inflamed, swollen, and scaly patches of skin where the old skin has not shed quickly enough. Plaque psoriasis, the most common form, is characterized by inflamed patches of skin ("lesions") topped with silvery white scales. Psoriasis may be limited to a few plaques or involve moderate to extensive areas of skin, appearing most commonly on the scalp, knees, elbows and trunk. Although it is highly visible, psoriasis is not a contagious disease. The pathogenesis of the diseases involves chronic inflammation of the affected tissues. zB7R1 polypeptides, anti-zB7R1 antibodies, or anti IL-22 and anti zB7R1 antibodies or binding partners, could serve as a valuable therapeutic to reduce inflammation and pathological effects in psoriasis, other inflammatory skin diseases, skin and mucosal allergies, and related diseases.

Psoriasis is a T-cell mediated inflammatory disorder of the skin that can cause considerable discomfort. It is a disease for which there is no cure and affects people of all ages. Psoriasis affects approximately two percent of the populations of European and North America. Although individuals with mild psoriasis can often control their disease with topical agents, more than one million patients worldwide require ultraviolet or systemic immunosuppressive therapy. Unfortunately, the inconvenience and risks of ultraviolet radiation and the toxicities of many therapies limit their long-term use. Moreover, patients usually have recurrence of psoriasis, and in some cases rebound, shortly after stopping immunosuppressive therapy.

Moreover, anti-zB7R1 antibodies and zB7R1 soluble receptors of the present invention can be used in the prevention and therapy against weight loss associated with a number of inflammatory diseases described herein, as well as for cancer (e.g., chemotherapy and cachexia), and infectious diseases. For example, severe weight loss is a key marker associated with models for septicemia, MS, RA, and tumor models. In addition, weight loss is a key parameter for many human diseases including cancer, infectious disease and inflammatory disease. Anti-zB7R1 antibodies and zB7R1 antagonists such as the soluble zB7R1 receptors and antibodies thereto of the present invention, can be tested for their ability to prevent and treat weight loss in mice injected with zB7R1 andenovires described herein. Methods of determining a prophylactic or therapeutic regimen for such zB7R1 antagonists is known in the art and can be determined using the methods described herein.

zB7R1 soluble receptor polypeptides and antibodies thereto may also be used within diagnostic systems for the detection of circulating levels of zB7R1 or zB7R1 counter-receptor, and in the detection of zB7R1 associated with acute phase inflammatory response. Within a related embodiment, antibodies or other agents that specifically bind to zB7R1 soluble receptors of the present invention can be used to detect circulating receptor polypeptides; conversely, zB7R1 soluble receptors themselves can be used to detect circulating or locally-acting zB7R1 polypeptides. Elevated or depressed levels of zB7R1 counter-receptor or zB7R1 polypeptides may be indicative of pathological conditions, including inflammation or cancer. Moreover, detection of acute phase proteins or molecules such as zB7R1 can be indicative of a chronic inflammatory condition in certain disease states (e.g., psoriasis, rheumatoid arthritis, colitis, IBD). Detection of such conditions serves to aid in disease diagnosis as well as help a physician in choosing proper therapy.

For example, neutralizing antibodies to zB7R1 include antibodies, such as neutralizing monoclonal antibodies that can bind zB7R1 antigenic epitopes and neutralize zB7R1 activity. Accordingly, antigenic epitope-bearing peptides and polypeptides of zB7R1 are useful to raise antibodies that bind with the zB7R1 polypeptides described herein, as well as to identify and screen anti-zB7R1 monoclonal antibodies that are neutralizing, and that may bind, block, inhibit, reduce, antagonize or neutralize the activity of zB7R1. Such neutralizing monoclonal antibodies of the present invention can bind to an zB7R1 antigenic epitope.

In addition to other disease models described herein, the activity of anti-zB7R1 antibodies on inflammatory tissue derived from human psoriatic lesions can be measured in vivo using a severe combined immune deficient (SCID) mouse model. Several mouse models have been developed in which human cells are implanted into immunodeficient mice (collectively referred to as xenograft models); see, for example, Cattan A R, Douglas E, *Leuk. Res.* 18:513-22, 1994 and Flavell, D J, *Hematological Oncology* 14:67-82, 1996. As an in vivo xenograft model for psoriasis, human psoriatic skin tissue is implanted into the SCID mouse model, and challenged with an appropriate antagonist. Moreover, other psoriasis animal models in the art may be used to evaluate zB7R1 antagonists, such as human psoriatic skin grafts implanted into AGR129 mouse model, and challenged with an appropriate antagonist (e.g., see, Boyman, O. et al., *J. Exp. Med.* Online publication #20031482, 2004, incorporated herein by reference). Anti-zB7R1 antibodies that bind, block, inhibit, reduce, antagonize or neutralize the activity of zB7R1 are preferred antagonists, however, anti-zB7R1 antibodies (alone or in combination with other B7 antagonists), soluble zB7R1, as well as other zB7R1 antagonists can be used in this model. Similarly, tissues or cells derived from human colitis, IBD, arthritis, or other inflammatory lestions can be used in the SCID model to assess the anti-inflammatory properties of the zB7R1 antagonists described herein.

Therapies designed to abolish, retard, or reduce inflammation using anti-zB7R1 antibodies or its derivatives, agonists, conjugates or variants can be tested by administration of anti-zB7R1 antibodies or soluble zB7R1 compounds to SCID mice bearing human inflammatory tissue (e.g., psoriatic lesions and the like), or other models described herein. Efficacy of treatment is measured and statistically evaluated as increased anti-inflammatory effect within the treated population over time using methods well known in the art. Some exemplary methods include, but are not limited to measuring for example, in a psoriasis model, epidermal thickness, the number of inflammatory cells in the upper dermis, and the grades of parakeratosis. Such methods are known in the art and described herein. For example, see Zeigler, M. et al. *Lab Invest* 81:1253, 2001; Zollner, T. M. et al. *J. Clin. Invest.* 109:671, 2002; Yamanaka, N. et al. *Microbiol. Immunol.* 45:507, 2001; Raychaudhuri, S. P. et al. *Br. J. Dermatol.* 144:931, 2001; Boehncke, W. H et al. *Arch. Dermatol. Res.* 291:104, 1999; Boehncke, W. H et al. *J. Invest. Dermatol.* 116:596, 2001; Nickoloff, B. J. et al. *Am. J. Pathol.* 146:580, 1995; Boehncke, W. H et al. *J. Cutan. Pathol.* 24:1, 1997; Sugai, J., M. et al. *J. Dermatol. Sci.* 17:85, 1998; and Villadsen L. S. et al. *J. Clin. Invest.* 112:1571, 2003. Inflammation may also be monitored over time using well-known methods such as flow cytometry (or PCR) to quantitate the number of inflammatory or lesional cells present in a sample, score (weight loss, diarrhea, rectal bleeding, colon length) for IBD, paw disease score and inflammation score for CIA RA model. For example, therapeutic strategies appropriate for testing in such a model include direct treatment using anti-zB7R1 antibodies, other zB7R1 antagonists (singly or together with other B7 antagonists), or related conjugates or antagonists based on the disrupting interaction of anti-zB7R1 antibodies with zB7R1, or for cell-based therapies utilizing anti-zB7R1 antibodies or its derivatives, agonists, conjugates or variants.

Moreover, psoriasis is a chronic inflammatory skin disease that is associated with hyperplastic epidermal keratinocytes and infiltrating mononuclear cells, including CD4+ memory T cells, neutrophils and macrophages (Christophers, *Int. Arch. Allergy Immunol.*, 110:199, 1996). It is currently believed that environmental antigens play a significant role in initiating and contributing to the pathology of the disease. However, it is the loss of tolerance to self-antigens that is thought to mediate the pathology of psoriasis. Dendritic cells and $CD4^+$ T cells are thought to play an important role in antigen presentation and recognition that mediate the immune response leading to the pathology. We have recently developed a model of psoriasis based on the CD4+CD45RB transfer model (Davenport et al., *Internat. Immunopharmacol.*, 2:653-672). Anti-zB7R1 antibodies of the present invention, or soluble zB7R1, are administered to the mice. Inhibition of disease scores (skin lesions, inflammatory cytokines) indicates the effectiveness of zB7R1 antagonists in psoriasis, e.g., anti-zB7R1 antibodies or zB7R1 soluble receptors, or other antagonists such as antibodies against the zB7R1 counter-receptor.

5. Atopic Dermatitis.

AD is a common chronic inflammatory disease that is characterized by hyperactivated cytokines of the helper T cell subset 2 (Th2). Although the exact etiology of AD is unknown, multiple factors have been implicated, including hyperactive Th2 immune responses, autoimmunity, infection, allergens, and genetic predisposition. Key features of the disease include xerosis (dryness of the skin), pruritus (itchiness of the skin), conjunctivitis, inflammatory skin lesions, *Staphylococcus aureus* infection, elevated blood eosinophilia, elevation of serum IgE and IgG1, and chronic dermatitis with T cell, mast cell, macrophage and eosinophil infiltration. Colonization or infection with *S. aureus* has been recognized to exacerbate AD and perpetuate chronicity of this skin disease.

AD is often found in patients with asthma and allergic rhinitis, and is frequently the initial manifestation of allergic disease. About 20% of the population in Western countries suffer from these allergic diseases, and the incidence of AD in developed countries is rising for unknown reasons. AD typically begins in childhood and can often persist through adolescence into adulthood. Current treatments for AD include topical corticosteroids, oral cyclosporin A, non-corticosteroid immunosuppressants such as tacrolimus (FK506 in ointment form), and interferon-gamma. Despite the variety of treatments for AD, many patients' symptoms do not improve, or they have adverse reactions to medications, requiring the search for other, more effective therapeutic agents. The soluble zB7R1 polypeptides and anti-zB7R1 antibodies of the present invention, can be used to neutralize zB7R1 in the treatment of specific human diseases such as atoptic dermatitis, inflammatory skin conditions, and other inflammatory conditions disclosed herein.

For pharmaceutical use, the soluble zB7R1 or anti-zB7R1 antibodies of the present invention are formulated for parenteral, particularly intravenous or subcutaneous, delivery according to conventional methods. Intravenous administration will be by bolus injection, controlled release, e.g, using mini-pumps or other appropriate technology, or by infusion over a typical period of one to several hours. In general, pharmaceutical formulations will include a hematopoietic protein in combination with a pharmaceutically acceptable vehicle, such as saline, buffered saline, 5% dextrose in water or the like. Formulations may further include one or more excipients, preservatives, solubilizers, buffering agents, albumin to provent protein loss on vial surfaces, etc. When utilizing such a combination therapy, the cytokines may be combined in a single formulation or may be administered in separate formulations. Methods of formulation are well known in the art and are disclosed, for example, in *Remington's Pharmaceutical Sciences*, Gennaro, ed., Mack Publishing Co., Easton Pa., 1990, which is incorporated herein by reference. Therapeutic doses will generally be in the range of 0.1 to 100 mg/kg of patient weight per day, preferably 0.5-20 mg/kg per day, with the exact dose determined by the clinician according to accepted standards, taking into account the nature and severity of the condition to be treated, patient traits, etc. Determination of dose is within the level of ordinary skill in the art. The proteins will commonly be administered over a period of up to 28 days following chemotherapy or bone-marrow transplant or until a platelet count of >20,000/mm$^3$, preferably >50,000/mm$^3$, is achieved. More commonly, the proteins will be administered over one week or less, often over a period of one to three days. In general, a therapeutically effective amount of soluble zB7R1 or anti-zB7R1 antibodies of the present invention is an amount sufficient to produce a clinically significant increase in the proliferation and/or differentiation of lymphoid or myeloid progenitor cells, which will be manifested as an increase in circulating levels of mature cells (e.g. platelets or neutrophils). Treatment of platelet disorders will thus be continued until a platelet count of at least 20,000/mm$^3$, preferably 50,000/mm$^3$, is reached. The soluble zB7R1 or anti-zB7R1 antibodies of the present invention can also be administered in combination with other cytokines such as IL-3, -6 and -11; stem cell factor; erythropoietin; G-CSF and GM-CSF. Within regimens of combination therapy, daily doses of other cytokines will in general be: EPO, 150 U/kg; GM-CSF, 5-15 lg/kg; IL-3, 1-5 lg/kg; and G-CSF, 1-25 lg/kg. Combination therapy with EPO, for example, is indicated in anemic patients with low EPO levels.

Generally, the dosage of administered soluble zB7R1 (or zB7R1 analog or fusion protein) or anti-zB7R1 antibodies will vary depending upon such factors as the patient's age, weight, height, sex, general medical condition and previous medical history. Typically, it is desirable to provide the recipient with a dosage of soluble zB7R1 or anti-zB7R1 antibodies which is in the range of from about 1 pg/kg to 10 mg/kg (amount of agent/body weight of patient), although a lower or higher dosage also may be administered as circumstances dictate.

Administration of soluble zB7R1 or anti-zB7R1 antibodies to a subject can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

Additional routes of administration include oral, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in *Protein Delivery: Physical Systems*, Sanders and Hendren (eds.), pages 255-288 (Plenum Press 1997)). The feasibility of an intranasal delivery is exemplified by such a mode of insulin administration (see, for example, Hinchcliffe and Illum, *Adv. Drug Deliv. Rev.* 35:199 (1999)). Dry or liquid particles comprising zB7R1 can be prepared and inhaled with the aid of dry-powder dispersers, liquid aerosol generators, or nebulizers (e.g., Pettit and Gombotz, *TIBTECH* 16:343 (1998); Patton et al., *Adv. Drug Deliv. Rev.* 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of trascutaneous administration (Mitragotri et al., *Science* 269: 850 (1995)). Transdermal delivery using electroporation provides another means to administer a molecule having zB7R1 binding activity (Potts et al., *Pharm. Biotechnol.* 10:213 (1997)).

A pharmaceutical composition comprising a soluble zB7R1 or anti-zB7R1 antibody can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), *Remington's Pharmaceutical Sciences*, 19th Edition (Mack Publishing Company 1995).

For purposes of therapy, soluble zB7R1 or anti-zB7R1 antibody molecules and a pharmaceutically acceptable carrier are administered to a patient in a therapeutically effective amount. A combination of a therapeutic molecule of the present invention and a pharmaceutically acceptable carrier is said to be administered in a "therapeutically effective amount" if the amount administered is physiologically significant. An agent is physiologically significant if its presence results in a detectable change in the physiology of a recipient patient. For example, an agent used to treat inflammation is physiologically significant if its presence alleviates the inflammatory response.

A pharmaceutical composition comprising zB7R1 (or zB7R1 analog or fusion protein) or anti-zB7R1 antibody can be furnished in liquid form, in an aerosol, or in solid form. Liquid forms, are illustrated by injectable solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)).

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (Suppl. 1):561 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 μm to greater than 10 μm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446:368 (1985)). After intravenous administration, small liposomes (0.1 to 1.0 μm) are typically taken up by cells of the reticuloendothelial system, located principally in the liver and spleen, whereas liposomes larger than 3.0 μm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

Liposomes can also be prepared to target particular cells or organs by varying phospholipid composition or by inserting receptors or counter-receptors into the liposomes. For example, liposomes, prepared with a high content of a nonionic surfactant, have been used to target the liver (Hayakawa et al., Japanese Patent 04-244,018; Kato et al., *Biol. Pharm. Bull.* 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull.* 20:881 (1997)).

Alternatively, various targeting counter-receptors can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287 (1997); Murahashi et al., *Biol. Pharm. Bull.* 20:259 (1997)). Similarly, Wu et al., *Hepatology* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.* 20:259 (1997)). Polyaconitylated human serum albumin liposomes provide another approach for targeting liposomes to liver cells (Kamps et al., *Proc. Nat'l Acad. Sci. USA* 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a counter-receptor expressed by the target cell (Harasym et al., *Adv. Drug Deliv. Rev.* 32:99 (1998)). After plasma elimination of free antibody, streptavidin-conjugated liposomes are administered. In another approach, targeting antibodies are directly attached to liposomes (Harasym et al., *Adv. Drug Deliv. Rev.* 32:99 (1998)).

Polypeptides and antibodies can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology*, 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly(ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly(lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., *Science* 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

The present invention also contemplates chemically modified polypeptides having binding zB7R1 activity such as zB7R1 monomeric, homodimeric, heterodimeric or multimeric soluble receptors, and zB7R1 antagonists, for example anti-zB7R1 antibodies or binding polypeptides, or neutralizing anti-zB7R1 antibodies, which a polypeptide is linked with a polymer, as discussed above.

Other dosage forms can be devised by those skilled in the art, as shown, for example, by Ansel and Popovich, *Pharmaceutical Dosage Forms and Drug Delivery Systems, 5$^{th}$* Edition (Lea & Febiger 1990), Gennaro (ed.), *Remington's Pharmaceutical Sciences, 19$^{th}$* Edition (Mack Publishing Company 1995), and by Ranade and Hollinger, *Drug Delivery Systems* (CRC Press 1996).

As an illustration, pharmaceutical compositions may be supplied as a kit comprising a container that comprises a polypeptide with a zB7R1 extracellular domain, e.g., zB7R1 monomeric, homodimeric, heterodimeric or multimeric soluble receptors, or a zB7R1 antagonist (e.g., an antibody or antibody fragment that binds a zB7R1 polypeptide, or neutralizing anti-zB7R1 antibody). Therapeutic polypeptides can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide. Such a kit may further comprise written information on indications and usage of the pharmaceutical composition. Moreover, such information may include a statement that the zB7R1 composition is contraindicated in patients with known hypersensitivity to zB7R1.

A pharmaceutical composition comprising Anti-zB7R1 antibodies or binding partners (or Anti-zB7R1 antibody fragments, antibody fusions, humanized antibodies and the like), or zB7R1 soluble receptor, can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)). Other solid forms include creams, pastes, other topological applications, and the like.

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (Suppl. 1):561 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 μm to greater than 10 μm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446:368 (1985)). After intravenous administration, small liposomes (0.1 to 1.0 μm) are typically taken up by cells of the reticuloendothelial system, located principally in the liver and spleen, whereas liposomes larger than 3.0 μm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

Liposomes can also be prepared to target particular cells or organs by varying phospholipid composition or by inserting receptors or counter-receptors into the liposomes. For example, liposomes, prepared with a high content of a nonionic surfactant, have been used to target the liver (Hayakawa et al., Japanese Patent 04-244,018; Kato et al., *Biol. Pharm. Bull.* 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull.* 20:881 (1997)).

Alternatively, various targeting counter-receptors can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287 (1997); Murahashi et al., *Biol. Pharm. Bull.* 20:259 (1997)). Similarly, Wu et al., *Hepatology* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.* 20:259 (1997)). Polyaconitylated human serum albumin liposomes provide another approach for targeting liposomes to liver cells (Kamps et al., *Proc. Nat'l Acad. Sci. USA* 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a counter-receptor expressed by the target cell (Harasym et al., *Adv. Drug Deliv. Rev.* 32:99 (1998)). After plasma elimination of free antibody, streptavidin-conjugated liposomes are administered. In another approach, targeting antibodies are directly attached to liposomes (Harasym et al., *Adv. Drug Deliv. Rev.* 32:99 (1998)).

Anti-zB7R1 neutralizing antibodies and binding partners with zB7R1 binding activity, or zB7R1 soluble receptor, can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology,* 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly (ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly(lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., *Science* 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

The present invention also contemplates chemically modified Anti-zB7R1 antibody or binding partner, for example anti-zB7R1 antibodies or zB7R1 soluble receptor, linked with a polymer, as discussed above.

Other dosage forms can be devised by those skilled in the art, as shown, for example, by Ansel and Popovich, *Pharmaceutical Dosage Forms and Drug Delivery Systems*, 5$^{th}$ Edition (Lea & Febiger 1990), Gennaro (ed.), *Remington's Pharmaceutical Sciences*, 19$^{th}$ Edition (Mack Publishing Company 1995), and by Ranade and Hollinger, *Drug Delivery Systems* (CRC Press 1996).

The present invention contemplates compositions of anti-zB7R1 antibodies, and methods and therapeutic uses comprising an antibody, peptide or polypeptide described herein. Such compositions can further comprise a carrier. The carrier can be a conventional organic or inorganic carrier. Examples of carriers include water, buffer solution, alcohol, propylene glycol, macrogol, sesame oil, corn oil, and the like.

12. Production of Transgenic Mice

Nucleic acids which encode zB7R1 or modified forms thereof can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding a zB7R1 protein can be used to clone genomic DNA encoding a zB7R1 protein in accordance with established techniques and the genomic sequences used to generate transgenic animals that contain cells which express the desired DNA. Methods for generating transgenic animals, particularly animals such as mice or rats, have become conventional in the art and are described, for example, in U.S. Pat. Nos. 4,736,866 and 4,870,009.

Alternatively, non-human homologues of zB7R1 can be used to construct a "knock out" animal which has a defective or altered gene encoding a zB7R1 protein as a result of homologous recombination between the endogenous gene and an altered genomic DNA encoding zB7R1, which is introduced into an embryonic cell of the animal. For example, cDNA encoding a zB7R1 protein can be used to clone genomic DNA encoding a zB7R1 protein in accordance with established techniques. A portion of the genomic DNA encoding a zB7R1 protein can be deleted or replaced with another gene, such as a gene encoding a selectable marker which can be used to monitor integration. Typically, several kilobases of unaltered flanking DNA (both at the 5' and 3' ends) are included in the vector. See e.g., Thomas and Capecchi, *Cell*, 51:503 (1987). The vector is introduced into an embryonic stem cell line (e.g., by electroporation) and cells in which the introduced DNA has homologously recombined with the endogenous DNA are selected. See e.g., Li et al., *Cell*, 69:915 (1992). The selected cells are then injected into a blastocyst of an animal (e.g., a mouse or rat) to form aggregation chimeras. See e.g., Bradley, in *Teratocarcinomas and Embryonic Stem Cells: A Practical Approach*, E. J. Robertson, ed. (IRL, Oxford, 1987), pp. 113-152. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the zB7R1 protein. It is understood that the models described herein can be varied. For example, "knock-in" models can be formed, or the models can be cell-based rather than animal models.

The invention is further illustrated by the following non-limiting examples.

Example 1

Murine zB7R1 Expression Construct

An expression plasmid containing a polynucleotide encoding the full-length mouse zB7R1 (SEQ ID NO:8) was constructed via homologous recombination. A fragment of mouse zB7R1 cDNA was isolated by PCR using the polynucleotide sequence as identified by SEQ ID NO:29 with flanking regions at the 5' and 3' ends corresponding to the vector sequences flanking the mouse zB7R1 insertion point using primers zc51280 (SEQ ID NO:30) and zc51314 (SEQ ID NO:31).

The PCR reaction mixture was run on a 2% agarose gel and a band corresponding to the size of the insert is gel-extracted using a QIAquick™ Gel Extraction Kit (Qiagen, Valencia, Calif.). Plasmid pZMP21 is a mammalian expression vector containing an expression cassette having the MPSV promoter, multiple restriction sites for insertion of coding sequences, a stop codon, an *E. coli* origin of replication; a mammalian selectable marker expression unit comprising an SV40 promoter, enhancer and origin of replication, a DHFR gene, and the SV40 terminator; and URA3 and CEN-ARS sequences required for selection and replication in *S. cerevisiae*. It was constructed from pZP9 (deposited at the American Type Culture Collection, 10801 University Boulevard, Manassas, Va. 20110-2209, under Accession No. 98668) with the yeast genetic elements taken from pRS316 (deposited at the American Type Culture Collection, 10801 University Boulevard, Manassas, Va. 20110-2209, under Accession No. 77145), an internal ribosome entry site (IRES) element from poliovirus, and the extracellular domain of CD8 truncated at the C-terminal end of the transmembrane domain. Plasmid pZMP21 was digested with BglII, and used for recombination with the PCR insert.

The recombination was performed using the BD In-Fusion™ Dry-Down PCR Cloning kit (BD Biosciences, Palo Alto, Calif.). The mixture of the PCR fragment and the digested vector in 10 µl was added to the lyophilized cloning reagents and incubated at 37° C. for 15 minutes and 50° C. for 15 minutes. The reaction was ready for transformation. 2 µl of recombination reaction was transformed into One Shot TOP10 Chemical Competent Cells (Invitrogen, Carlbad, Calif.); the transformation was incubated on ice for 10 minutes and heat shocked at 42° C. for 30 seconds. The reaction was incubated on ice for 2 minutes (helping transformed cells to recover). After the 2 minutes incubation, 300 µl of SOC (2% Bacto™ Tryptone (Difco, Detroit, Mich.), 0.5% yeast extract (Difco), 10 mM NaCl, 2.5 mM KCl, 10 mM MgCl$_2$, 10 mM MgSO$_4$, 20 mM glucose) was added and the transformation was incubated at 37° C. with shaker for one hour. The whole transformation was plated on one LB AMP plates (LB broth (Lennox), 1.8% Bacto™ Agar (Difco), 100 mg/L Ampicillin).

The colonies were screened by PCR using primers zc51280 (SEQ ID NO:30) and zc51314 (SEQ ID NO:31), respectively. The positive colonies were verified by sequencing. The correct construct was designated as mzB7R1FLpZMP21.

Example 2

Mouse zB7R1mFc2pZMP21

An expression plasmid containing a polynucleotide encoding the extra-cellular domain of mouse zB7R1 and the mouse Fc2 portion can be constructed via homologous recombination. A DNA fragment of the extra-cellular domain of mouse zB7R1 is isolated by PCR using SEQ ID NO:32 with flanking regions at the 5' and 3' ends corresponding to the vector sequence and the mouse Fc2 sequence flanking the mouse zB7R1 insertion point using primers zc50437 (SEQ ID NO:33) and zc50438 (SEQ ID NO:34).

The PCR reaction mixture is run on a 2% agarose gel and a band corresponding to the size of the insert is gel-extracted using a QIAquick™ Gel Extraction Kit (Qiagen, Valencia, Calif.). The initial plasmid used is pZMP21 that used pZMP21 as a base vector and has the mouse Fc2 portion built into it. Plasmid pZMP21 is a mammalian expression vector containing an expression cassette having the MPSV promoter, multiple restriction sites for insertion of coding sequences, a stop codon, an E. coli origin of replication; a mammalian selectable marker expression unit comprising an SV40 promoter, enhancer and origin of replication, a DHFR gene, and the SV40 terminator; and URA3 and CEN-ARS sequences required for selection and replication in S. cerevisiae. It is constructed from pZP9 (deposited at the American Type Culture Collection, 10801 University Boulevard, Manassas, Va. 20110-2209, under Accession No. 98668) with the yeast genetic elements taken from pRS316 (deposited at the American Type Culture Collection, 10801 University Boulevard, Manassas, Va. 20110-2209, under Accession No. 77145), an internal ribosome entry site (IRES) element from poliovirus, and the extracellular domain of CD8 truncated at the C-terminal end of the transmembrane domain. Plasmid hBTLA mFc2 pZMP21 was digested with EcoR1/BglII to cleave off human BTLA and used for recombination with the PCR insert.

The recombination was performed using the BD In-Fusion™ Dry-Down PCR Cloning kit (BD Biosciences, Palo Alto, Calif.). The mixture of the PCR fragment and the digested vector in 10 µl was added to the lyophilized cloning reagents and incubated at 37° C. for 15 minutes and 50° C. for 15 minutes. The reaction was ready for transformation. 2 µl of recombination reaction was transformed into One Shot TOP10 Chemical Competent Cells (Invitrogen, Carlbad, Calif.); the transformation was incubated on ice for 10 minutes and heat shocked at 42° C. for 30 seconds. The reaction was incubated on ice for 2 minutes (helping transformed cells to recover). After the 2 minutes incubation, 300 µl of SOC (2% Bacto™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was added and the transformation was incubated at 37° C. with shaker for one hour. The whole transformation was plated on one LB AMP plates (LB broth (Lennox), 1.8% Bacto™ Agar (Difco), 100 mg/L Ampicillin).

The colonies were screened by PCR using primers zc50437 (SEQ ID NO:33) and zc50438 (SEQ ID NO:34). The positive colonies were verified by sequencing. The correct construct was designated as mB7R1mFc2pZMP21 (SEQ ID NO: 69).

Example 3

B7/mFc2 Expression Constructs

An expression vector, pZMP21 hB7R1/mFc2 (SEQ ID NO: 68), was prepared to express a c-terminally Fc tagged soluble version of zB7R1. A 734 base pair fragment was generated by PCR containing the extracellular domain of zB7R1 (SEQ ID NO:3) and the first two amino acids of mFc (glutamine and proline) with EcoRI and BglII sites coded on the 5' and 3' ends, respectively.

This PCR fragment was generated using primers zc48914 (SEQ ID NO:35) and zc48908 (SEQ ID NO:36) by amplification from a human placenta cDNA library. The PCR reaction conditions were as follows: 25 cycles of 94° C. for 1 minute, 60° C. for 1 minute, and 72° C. for 2 minutes; 1 cycle at 72° C. for 10 minutes; followed by a 4° C. soak. A 699 base pair fragment was generated by PCR containing the constant 2 and constant 3 domains of effector function minus BALB-C IgG gamma 2a (mFc2). This PCR fragment was generated using primers zc48911 and ac48915 by amplification from an expression vector containing mFc2 (mTACI/mFc2 construct #998). The PCR reaction conditions were as follows: 25 cycles of 94° C. for 1 minute, 60° C. for 1 minute, and 72° C. for 2 minutes; 1 cycle at 72° C. for 10 minutes; followed by a 4° C. soak. The 734 base pair zB7R1 fragment and the 699 base pair mFc2 fragment were purified by 1% agarose gel electrophoresis and band purification using a QiaQuick gel extraction kit (Qiagen: 28704). $\frac{1}{5}^{th}$ and $\frac{1}{25}^{th}$ of the total of the purified bands each for the zB7R1 and the mFc2 fragments, respectively were recombined into pZMP21 that had been linearized by BglII digestion and purified by band purification, as described above, using the yeast strain SF838-9Dalpha. Yeast that were able to grow out of uracil deficient agar plates were lysed and DNA was extracted by ethanol precipitation. 2 µl of the ligation mix was electroporated in 37 µl DH10B electrocompetent E. coli (Gibco 18297-010) according to the manufacturer's directions. The transformed cells were diluted in 400 µl of LB media and plated onto LB plates containing 100 µg/ml ampicillin. Clones were analyzed by restriction digests and positive clones were sent for DNA sequencing to confirm PCR accuracy.

The expression vector, pZMP21 hB7R1/mfc2, described above, was then used to build a series of mFc2 soluble chimeric proteins. zB7R1/mFc2 was built by PCRing a 438 base pair fragment using oligos zc 50136 (SEQ ID NO:37) and zc50138 (SEQ ID NO:38) with clonetrack #101632 as template. The resulting PCR product was band purified, as described above, and disgested with EcoRI and BglII. The resulting product was again band purified. PZMP21 hB7R1/mFc2 was also digested with EcoRI and BglII and the 9721 base pair vector backbone plus mFc2 was isolated. $\frac{1}{50}^{th}$ of the pZMP21 hB7R1/mFc2 product was ligated to $\frac{3}{50}^{th}$ of the 438 base pair fragment using T4 DNA ligase. 2 µl of the ligation mix was electroporated in 37 µl DH10B electrocompetent E. coli (Gibco 18297-010) according to the manufacturer's directions. The transformed cells were diluted in 400 µl of LB media and plated onto LB plates containing 100 µg/ml ampicillin. Clones were analyzed by restriction digests and positive clones were sent for DNA sequencing to confirm PCR accuracy. Three sets of 200 µg of the pZMP21 hB7R1/mFc2 construct were then each digested with 200 units of Pvu I at 37° C. for three hours and then were precipitated with IPA and spun down in a 1.5 mL microfuge tube. The supernatant was decanted off the pellet, and the pellet was washed with 1 mL of 70% ethanol and allowed to incubate for 5 minutes at room temperature. The tube was spun in a microfuge for 10 minutes at 14,000 RPM and the supernatant was decanted off the pellet. The pellet was then resuspended in 750 µl of PF-CHO media in a sterile environment, allowed to incubate at 60° C. for 30 minutes, and was allowed to cool to room temperature. 5E6 APFDXB11 cells were spun down in each of three tubes and were resuspended using the DNA-media solution. The DNA/cell mixtures were placed in a 0.4 cm gap cuvette and electroporated using the following parameters: 950 µF, high capacitance, and 300 V. The contents of the cuvettes were then removed, pooled, and diluted to 25 mLs with PF-CHO media and placed in a 125 mL shake flask. The flask was placed in an incubator on a shaker at 37° C., 6% $CO_2$, and shaking at 120 RPM. The cell line was subjected to nutrient selection followed by step amplification to 200 nM methotrexate (MTX), and then to 500 nM MTX. Expression was confirmed by western blot, and the cell line was scaled-up and protein purification followed.

Example 4

Mouse zB7R1Avi-HIS TagpZMP21

In the effort to create the tetramer molecules an expression plasmid containing a polynucleotide encoding the extra-cellular domain of mouse zB7R1, the Avi Tag and HIS Tag was constructed. A DNA fragment of the extra-cellular domain of mouse zB7R1 is isolated by PCR using SEQ ID NO:39 with flanking regions at the 5' and 3' ends corresponding to the vector sequence and part of the Avi Tag sequence flanking the mouse zB7R1 insertion point using primers zc51100 (SEQ ID NO:40) and zc51101 (SEQ ID NO:41).

The PCR reaction mixture is run on a 2% agarose gel and a band corresponding to the size of the insert is gel-extracted using a QIAquick™ Gel Extraction Kit (Qiagen, Valencia, Calif.). Plasmid pZMP21 is a mammalian expression vector containing an expression cassette having the MPSV promoter, multiple restriction sites for insertion of coding sequences, a stop codon, an *E. coli* origin of replication; a mammalian selectable marker expression unit comprising an SV40 promoter, enhancer and origin of replication, a DHFR gene, and the SV40 terminator; and URA3 and CEN-ARS sequences required for selection and replication in *S. cerevisiae*. It is constructed from pZP9 (deposited at the American Type Culture Collection, 10801 University Boulevard, Manassas, Va. 20110-2209, under Accession No. 98668) with the yeast genetic elements taken from pRS316 (deposited at the American Type Culture Collection, 10801 University Boulevard, Manassas, Va. 20110-2209, under Accession No. 77145), an internal ribosome entry site (IRES) element from poliovirus, and the extracellular domain of CD8 truncated at the C-terminal end of the transmembrane domain. Plasmid pZMP21AviHIS was digested with EcoR1 and used for recombination with the PCR insert.

The recombination was performed using the BD In-Fusion™ Dry-Down PCR Cloning kit (BD Biosciences, Palo Alto, Calif.). The mixture of the PCR fragment and the digested vector in 10 µl was added to the lyophilized cloning reagents and incubated at 37° C. for 15 minutes and 50° C. for 15 minutes. The reaction was ready for transformation. 2 µl of recombination reaction was transformed into One Shot TOP10 Chemical Competent Cells (Invitrogen, Carlbad, Calif.); the transformation was incubated on ice for 10 minutes and heat shocked at 42° C. for 30 seconds. The reaction was incubated on ice for 2 minutes (helping transformed cells to recover). After the 2 minutes incubation, 300 µl of SOC (2% Bacto™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was added and the transformation was incubated at 37° C. with shaker for one hour. The whole transformation was plated on one LB AMP plates (LB broth (Lennox), 1.8% Bacto™ Agar (Difco), 100 mg/L Ampicillin).

The colonies were screened by PCR using primers zc51100 (SEQ ID NO:40) and zc51101 (SEQ ID NO:41). The positive colonies were verified by sequencing. The correct construct was designated as mB7R1AviHISpZMP21.

Example 5

Human zB7R1Avi-HIS TagpZMP21

In the effort to create the tetramer molecules an expression plasmid containing a polynucleotide encoding the extra-cellular domain of human zB7R1 (SEQ ID NO:3), the Avi Tag and HIS Tag was constructed. A DNA fragment of the extra-cellular domain of human zB7R1 is isolated by PCR using SEQ ID NO:42 with flanking regions at the 5' and 3' ends corresponding to the vector sequence and the Avi Tag (SEQ 10 NO:43) and HIS Tag (SEQ ID NO:44) sequences flanking the human zB7R1 insertion point using primers zc50485 (SEQ ID NO:45) and zc50729 (SEQ ID NO:46).

The PCR reaction mixture is run on a 2% agarose gel and a band corresponding to the size of the insert is gel-extracted using a QIAquick™ Gel Extraction Kit (Qiagen, Valencia, Calif.). Plasmid pZMP21 is a mammalian expression vector containing an expression cassette having the MPSV promoter, multiple restriction sites for insertion of coding sequences, a stop codon, an *E. coli* origin of replication; a mammalian selectable marker expression unit comprising an SV40 promoter, enhancer and origin of replication, a DHFR gene, and the SV40 terminator; and URA3 and CEN-ARS sequences required for selection and replication in *S. cerevisiae*. It is constructed from pZP9 (deposited at the American Type Culture Collection, 10801 University Boulevard, Manassas, Va. 20110-2209, under Accession No. 98668) with the yeast genetic elements taken from pRS316 (deposited at the American Type Culture Collection, 10801 University Boulevard, Manassas, Va. 20110-2209, under Accession No. 77145), an internal ribosome entry site (IRES) element from poliovirus, and the extracellular domain of CD8 truncated at the C-terminal end of the transmembrane domain. Plasmid pZMP21 was digested with EcoR1/BglII to cleave off the PTA leader and used for recombination with the PCR insert.

The recombination was performed using the BD In-Fusion™ Dry-Down PCR Cloning kit (BD Biosciences, Palo Alto, Calif.). The mixture of the PCR fragment and the digested vector in 10 µl was added to the lyophilized cloning reagents and incubated at 37° C. for 15 minutes and 50° C. for 15 minutes. The reaction was ready for transformation. 2 µl of recombination reaction was transformed into One Shot TOP10 Chemical Competent Cells (Invitrogen, Carlbad, Calif.); the transformation was incubated on ice for 10 minutes and heat shocked at 42° C. for 30 seconds. The reaction was incubated on ice for 2 minutes (helping transformed cells to recover). After the 2 minutes incubation, 300 μl of SOC (2% Bacto™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was added and the transformation was incubated at 37° C. with shaker for one hour. The whole transformation was plated on one LB AMP plates (LB broth (Lennox), 1.8% Bacto™ Agar (Difco), 100 mg/L Ampicillin).

The colonies were screened by PCR using primers zc50485 (SEQ ID NO:45) and zc50729 (SEQ ID NO:46). The positive colonies were verified by sequencing. The correct construct was designated as hB7R1AviHISpZMP21.

Example 6

Stimulation Conditions for the Expression of zB7R1 and Other B7 Family Members

A. Introduction

Stimulation conditions under which known B7 family members are expressed and/or upregulated on murine bone marrow derived dendritic cells (BMDCs) would be helpful in the assessment of zB7R1'a ability to bind cultured DCs. First, the regulation of known B7 family members was investigated using various stimulation conditions in FLT3L and GM-CSF/IL-4 cultures from BALB/c mice. Secondly, the binding of the available murine soluble Fc-fusion proteins to FLT3L, GM-CSF, and GM-CSF/IL-4 cultured bone marrow cells from both BALB/c and C57BL/6 strains of mice were tested. This is described in more detail below.

B. Methods

1) Isolating Bone Marrow

Bone marrow from 8-week-old female BALB/c mice or 4-month-old C57Bl/6 mice was collected from the femurs. The bone marrow was filtered through a 100 μM cell strainer, the red blood cells lysed with ACK Lysis buffer, and the cells resuspended in RPMI "complete" media (10% FCS, 2 mM L-Glutamine, 1 mM Na-Pyruvate, 0.1 mM NEAA, 0.05 mM β-ME). Cells were then plated in 6-well plates at $1\times10^6$ cells per ml with the appropriate culturing conditions.

(i) Generation of Flt3L BMDCs Cell Cultures

Bone marrow cells were cultured in the presence of 100 ng/ml of recombinant human Flt3 ligand. One half of the media was replaced on day 5 of culture with fresh Flt3L containing media. Cells were collected on day 7 of culture.

(ii) Generation of GM-CSF/IL-4 BMDCs Cell Cultures

Bone marrow cells were cultured in the presence of 10 ng/ml each of recombinant murine GM-CSF and recombinant murine IL-4 (both R&D Systems). One half of the media was replaced on day 3 of culture with fresh GM-CSF/IL-4 containing media. Cells were collected on day 6 of culture.

(iii) Generation of GM-CSF BMDCs Cell Cultures

Bone marrow cells were cultured in the presence of 20 ng/ml recombinant murine GM-CSF in 4 ml in 6-well plates. On day 3 of culture 2 ml of fresh GM-CSF containing media was added to each well, on day 6, one half of the media (3 ml) was replaced with fresh GM-CSF containing media. Cells were collected on day 7 of culture.

2) FACS Analysis

All stains and dilutions were performed in FACS wash buffer (PBS, 1% BSA, 0.1% $NaN_3$) Prior to staining, FcBlock (0.25 ug/$10^6$ cells) was added to the cells and incubated approximately 5-10 minutes. Cells were co-stained with CD11c and B220. All data was acquired on BD FACSCalibur.

C. Stimulation of Cell Cultures:

1) Investigation of Regulation of Known B7-Family Molecules

Cultured cells were plated at $1\times10^6$ cells per ml in 2 ml in 24-well plates and stimulated with 100 ng/ml LPS, 20 ng/ml IFNγ, 1 ug/ml CD40L, or a TLR ligand mix containing 0.1 ug/ml MALP-2, 12.5 ug/ml Poly I:C, 100 ng/ml LPS, 0.1 ug/ml Flagellin, 1 ug/ml R848, and 125 ng/ml CpG ODN1826. Cells were assayed by flow cytometry for B7 family expression at t=0, 24h, 48h, 72h, and 96h.

Cells were stained with one of the PE-conjugated B7 family antibodies B7-1, B7-2, B7-H1, B7-H2, B7-H3, B7-H4, B7-DC, ICOS, or PD-1. 7-AAD was used to gate out dead cells at the 72 and 96h timepoints.

Flt3L BMDCs (i) B7-1

At all timepoints, unstimulated cells expressed B7-1, and expression was further upregulated by LPS and the TLR ligand mix. The IFNγ and CD40L treatment had no effect on B7-1 expression relative to unstimulated cells.

(ii) B7-2

At all timepoints, unstimulated cells expressed B7-2, and expression was further upregulated by LPS, IFNγ and the TLR ligand mix. The CD40L treatment had no effect on B7-2 expression relative to unstimulated cells.

(iii) B7-H1

At 24h unstimulated cells do not express B7-H1, but LPS, IFNγ and the TLR ligand mix do induce expression. Unstimulated cells begin to express low levels of B7-H1 by 48h, and LPS, IFNγ and the TLR ligand mix continue to show upregulation of the B7-H1 relative to the unstimulated control. The CD40L treatment had no effect on B7-H1 expression relative to unstimulated cells.

(iv) B7-H2

At all timepoints, unstimulated cells expressed B7-H2. The IFNγ and CD40L treatment had little to no effect on B7-H2 expression relative to unstimulated cells. Treatment with the TLR ligand cocktail appeared to decrease B7-H2 expression.

(v) PD-1

Unstimulated Flt3L dendritic cells were negative for PD-1 expression, however TLR ligand stimulation induced expression at all timepoints, and LPS (weakly) and IFNγ induced upregulation at 48h, 72h, and 96h timepoints.

(vi) B7-H3, B7-H4, B7-DC, and ICOS

B7-H3, B7-H4, B7-DC, and ICOS were negative for expression, at all timepoints, with all stimulation conditions, in Flt3L generated dendritic cells.

GM-CSF/IL-4 BMDCs (i) B7-1

At all timepoints, unstimulated cells expressed B7-1, and expression was further upregulated by TLR ligand mix at 72h and 96h timepoints. The LPS, IFNγ and CD40L treatment had no effect on B7-1 expression relative to unstimulated cells.

(ii) B7-2

At all timepoints, unstimulated cells expressed B7-2, and expression was further upregulated by IFNγ and the TLR ligand mix at 72h and 96h timepoints. LPS decreased B7-2 expression at the 72 and 96h timepoints. The CD40L treatment had no effect on B7-2 expression relative to unstimulated cells.

(iii) B7-H1

Unstimulated GM-CSF/IL-4 BMDCs highly express B7-H1. LPS upregulated expression at only the 24h timepoint, and IFNγ and the TLR ligand mix upregulated expression at all timepoints. The CD40L treatment had no effect on B7-H1 expression relative to unstimulated cells.

(iv) B7-H2

At all timepoints, unstimulated cells expressed B7-H2. IFNγ treatment slightly upregulated B7-H2 expression relative to unstimulated cells at 48, 72, and 96h. All other stimulation conditions had no effect on B7-H2 expression relative to unstimulated cells.

(v) B7-DC

Unstimulated GM-CSF/IL-4 dendritic cells were positive for PD-1 expression, and IFNγ stimulation induced increased expression at 48h, 72h, and 96h timepoints LPS, CD40L, and TLR ligand cocktail had no effect on B&-DC expression relative to the unstimulated control.

(vi) B7-H3, B7-H4, PD-1, and ICOS

B7-H3, B7-H4, PD-1, and ICOS were negative for expression, at all timepoints, with all stimulation conditions, in GM-CSF/IL-4 generated dendritic cells.

2) Binding of Soluble Fc-Fusion Proteins

Cells were cultured as described above, however the stimulation conditions were modified to (i) LPS 100 ng/ml, (ii) CD40L (1 ug/nil) and IFNγ (20 ng/ml) and (iii) TLR ligand cocktail, with the some modifications (we omitted LPS, and used CpG ODN 2395 instead of CpG ODN 1826 (both murine TLR 9 ligands) and used Polyuridylic acid instead of R848 (both TLR 7/8 ligands)). Cells were assayed for binding to the available Fc-fusion proteins of interest at 48h by flow cytometry.

Murine Fc-fusion proteins pBTLA, zB7R1, zB7-H4 mL, and zB7-H4 mS as well as human zB7-H3×2 (negative control) and murine ICOS-Fc purchased from R&D Systems (positive control) were labeled with PE using Zenon Mouse IgG Labeling Kits (Molecular Probes) and used to stain the cells. The dye 7-AAD was used to gate out dead cells.

There did not appear to be any binding of murine pBTLA-Fc, zB7-H4 mL-Fc or zB7-H4 mS-Fc under any of the conditions tested.

However, murine zB7R1-Fc did appear to bind in CD40L+IFNγ stimulated Flt3L cultured cells in both BALB/c and C57Bl/6 strains of mice. Binding of zB7R1-Fc appeared negative in both the GM-CSF and GM-CSF/IL-4 cultured cells under conditions tested.

D. Conclusion

Conditions under which B7-1, B7-2, B7-H1, B7-H2, B7-DC, and PD-1 are expressed and/or upregulated in cell cultures enriched for dendritic cells were identified. Furthermore, binding of fluorescently labeled Fc fusion proteins of the orphan receptors and ligands to cells cultured under these conditions to define unknown counterparts for the unpaired B7 family members were tested. Specifically, one stimulation condition (IFNg+CD40L) was identified, which induced binding of zB7R1.

Example 7

Identification of Cells Expressing zB7R1

A. Introduction

The identification of a cell source expressing the counter-receptor for zB7R1 would help understand the biology of zB7R1 and also would assist in cloning the counter-receptor. A direct fluorochrome conjugate of zB7R1-mFc2a and mouse splenocytes surface stained with a cocktail of fluorochrome conjugated antibodies specific for lineage markers to identify activated CD11c$^+$ cells as the primary cell type that binds zB7R1 was used.

B. Procedure

A D011.10 mouse spleen transgenic for a TCR specific for the Ova peptide 323-339 was collected and mashed between frosted glass slides to obtain a single cell suspension. Red cells in the suspension were lysed using ACK lysis buffer. The resulting cell suspension was adjusted to $1\times10^6$ cells per well in media (RPMI+10% FBS, glutamine, pyruvate, pen-strep and 2-mercaptoethanol at $5\times10^{-5}$M) and incubated with 1 uM OVA peptide 323-339 at 37 C. Cells were collected for analysis by flow cytometry at times 0, 24, 48, and 72 hours.

zB7R1-mIgGFc2a fusion protein was directly labeled with PE using the Zenon™ R-Phycoerythrin mouse IgG2a labeling kit (Molecular Probes, Eugene Oreg., cat. #Z25155) following manufacturer's instructions. Cells collected at each timepoint were incubated in Facs buffer (PBS+2% BSA+0.02% NaN$_3$) with 5 ug/ml of Zenon™-PE labeled zB7R1-mFc2a. In some cases, these binding experiments were also performed in the presence of 40-fold excess unlabeled zB7R1-mFc2a (specific blocking) or 40 fold excess pB7H4L-mFc2a (non-specific blocking). Control wells were incubated with the Zenon™ labeling reagent alone or with an irrelevant Fc-fusion protein labeled in the same way. Cells were simultaneously incubated with antibodies to the following antigens: CD11c-APC, CD11b-PerCP-CY5, CD49b-APC-CY7, CD3-PeCy7 CD19-FITC (BD Pharmingen), CD8-PE-Texas Red and CD4-A405 (Caltag) at appropriate dilutions in FACS buffer on ice for 30 minutes. Cells were washed twice (adding Facs buffer at 4× the labeling volume and centrifuging the cells at 300×g for 5 minutes, decanting the supernatant for each wash), then fixed with 2% paraformaldehyde in PBS for 20 minutes. Cells were centrifuged at 300×g for 5 minutes and resuspended in 200 ul FACs buffer per $2\times10^5$ cells and stored at 4 C for up to 5 days. Samples were analyzed using a flow cytometer (FACSAria, Becton Dickenson) and FACS Diva software.

C. Results

Viable cells were gated on using forward and side scatter dot plots. Viable cells were then analyzed for CD11b and CD11c expression, as well as for the other surface markers in the staining combination. In one experiment, binding of zB7R1-mFc2a was observed on CD11c cells at all timepoints. In the same experiment, binding of zB7R1-mFc2a on CD11b CD11c double positive cells was detectable only at 48 and 72 hours. In another experiment, binding of zB7R1-mFc2a was observed on CD11c cells and CD11c CD11b double positive cells at 48 and 72 hours. Cells positive for CD11b but negative for CD11c did not bind zB7R1 significantly higher than cells stained with the labeling reagent alone or with an irrelevant Fc-fusion protein at all timepoints in both experiments. Cells with a CD1 CD11b$^{+/-}$ surface phenotype bound zB7R1 with a mean fluorescence of 1952 channels versus 660 for the control. The sample specifically blocked with excess unlabeled zB7R1-mFc2a had a mean channel fluorescence of 781 compared to 1682 for the sample non-specifically blocked with excess pB7H4L-mFc2a.

D. Conclusion

The CD11c surface marker is found on most dendritic cells and is used to identify them in the mixture of activated and resting spleen cells responses. The binding of zB7R1-mFc2a to the surface of dendritic cells indicates the presence of the cognate ligand on the surface of these cells. The binding increases on activated dendritic cells. The interaction of zB7R1 on dendritic cells and zB7R1 on T cells and possibly other cell types influences the progression of an immune response.

Example 8

Murine zB7R1 mRNA is Regulated in Select Tissues in Murine Models of Disease Compared to Non-Diseased Controls A. Procedure Tissues were obtained from the following murine models of disease: Colitis, Asthma, Experimental Allergic Encephalomyelitis (EAE), Psoriasis and Collagen Induced Arthritis (CIA). Animal models were run following standard procedures and included appropriate non-diseased controls. Colitis was induced by dextran sodium sulfate (DSS) in the drinking water and the tissues isolated from the model included distal colon, proximal colon and mesenteric lymph nodes. Asthma was induced by sensitization and intranasal challenge to the antigen ovalbumin. The tissues isolated included lung, spleen and lymph node. EAE was induced by immunizing with MOG35-55 peptide in RIBI adjuvant. Tissues isolated included brain, lymph node, and spinal cord. Psoriasis was induced by adoptive transfer of naive T cells into minor histocompatibility mismatched or syngeneic immunocompromised mice. Tissues isolated included lesional skin and adjacent skin. CIA was induced by collagen injections and tissues isolated included foot and lymph node. RNA was isolated from all tissues using standard procedures. In brief, tissues were collected and immediately frozen in liquid N2 and then transferred to −80° C. until processing. For processing, tissues were placed in Qiazol reagent (Qiagen, Valencia, Calif.) and RNA was isolated using the Qiagen Rneasy kit according to manufacturer's recommendations. Expression of murine zB7R1 mRNA was measured with multiplex real-time quantitative RT-PCR method (TaqMan) and the ABI PRISM 7900 sequence detection system (PE Applied Biosystems). zB7R1 mRNA levels were normalized to the expression of the murine hypoxanthine guanine physphoribosyl transferase mRNA and determined by the comparative threshold cycle method (User Bulletin 2; PE Applied Biosystems). The primers and probe for murine zB7R1 included a 5' forward primer (SEQ ID NO:47), reverse 5' primer (SEQ ID NO:48) and a probe (SEQ ID NO:49).

B. Results

Murine zB7R1 mRNA expression was detected in all tissues tested. Highest levels of expression were observed in the lymph node and spleen tissues. Lower levels of expression were found in skin, colon, lung, brain, foot, and spinal cord tissues.

Murine zB7R1 mRNA was increased in tissues from a chronic model of DSS colitis compared to tissues from non-diseased controls. Zb7r1 was increased 1.65 fold in the LN, 3.2 fold in the distal colon and 2.6 fold in the proximal colon compared to non-diseased controls.

zB7R1 mRNA was increased in tissues from the murine model of asthma compared to tissues from non-diseased controls. Zb7r1 was increased 5.4 fold in lung, 1.4 fold in spleen and 1.7 fold in lymph node.

Zb7r1 mRNA was increased in tissues from the EAE model compared to tissues from non-diseased controls. Zb7r1 mRNA was increased 16.87 fold in the brain of animals from the early onset of disease and 5.63 fold in animals with severe disease scores. Zb7r1 mRNA was increased 4.15 fold in the spinal cord of animals from the early onset of disease and 6.93 fold in animals with severe disease scores.

zB7R1 mRNA was increased in skin tissues from the psoriasis model compared to skin tissues from non-diseased controls. Zb7r1 mRNA was increased 2.24 fold in a skin lesion and 3.07 fold in skin tissue adjacent to the psoriatic lesion.

zB7R1 mRNA was increased in whole foot tissue from mice in the CIA model of arthritis compared to foot tissue from non-diseased controls. Zb7r1 mRNA was increased 2.31 fold in animals scored with mild disease and 3.4 fold in animals with severe disease.

Example 9

Cloning and Construction of VASP Expression Vector

Human vasodialator-activated phosphoprotein (VASP) is described by Kühnel, et al., (2004) Proc. Nat'l. Acad. Sci. 101: 17027. VASP nucleotide and amino acid sequences are provided as SEQ ID NOs: 13 and 14. Two overlapping oligonucleotides, which encoded both sense and antisense strands of the tetramerization domain of human VASP protein, were synthesized by solid phased synthesis using oligonucleotide zc50629 (SEQ ID NO:50) and oligonucleotide ZC 50630 (SEQ ID NO:51). These oligonucleotides were annealed at 55° C., and amplified by PCR with the olignucleotide primers zc50955 (SEQ ID NO:52) and zc50956 (SEQ ID NO:53).

The amplified DNA was fractionated on 1.5% agarose gel and then isolated using a Qiagen gel isolation kit according to manufacturer's protocol (Qiagen, Valiencia, Calif.). The isolated DNA was inserted into BglII cleaved pzmp21 vector by yeast recombination. DNA sequencing confirmed the expected sequence of the vector, which was designated pzmp21VASP-His$_6$.

The extra cellular domain of human zB7R1 was generated by restriction enzyme digestion of human zB7R1mFc2 (SEQ ID No:61). A double digest with EcoRI and BglII (Roche Indianapolis, Ind.) was performed to obtain the extra cellular domain. The fragment was fractionated on 2% agarose gel (Invitrogen Carlsbad, Calif.) and then isolated using a Qiagen gel isolation kit according to manufacturer's protocol (Qiagen Valencia Calif.). The isolated fragment was inserted into EcoRI/BglII cleaved pZMP21VASP-His$_6$ vector by ligation (Fast Link Ligase EPICENTRE Madison, Wis.). The construct was designated as hzB7R1VASPpZMP21 (SEQ ID No: 62).

The extra cellular domain of mouse zB7R1 was generated by restriction enzyme digestion of mouse zB7R1mFc2 SEQ ID No: 63. A double digest with EcoRI and BglII (Roche Indianapolis, Ind.) was performed to obtain the extra cellular domain. The fragment was fractionated on 2% agarose gel (Invitrogen Carlsbad, Calif.) and then isolated using a Qiagen gel isolation kit according to manufacturer's protocol (Qiagen Valencia Calif.). The isolated fragment was inserted into EcoRI/BglII cleaved pZMP21VASP-His$_6$ vector by ligation (Fast Link Ligase EPICENTRE Madison, Wis.). The construct was designated as mzB7R1VASPpZMP21 SEQ ID No: 64.

These vector includes the coding sequence for the zB7R1 extracellular domain (including the native signal sequence) comprising amino acids 1 to 140 of the full length gene (amino acids 1-140 of SEQ ID NO:2), the flexible linker GSGG (SEQ ID NO: 27), the VASP tetramerization domain (amino acids 5 to 38 of SEQ ID NO: 54), the flexible linker GSGG (SEQ ID NO:27), and the His$_6$ tag amino acid residues (amino acids 43 to 48 of SEQ ID NO: 54).

Example 10

Expression and Purification of B7R1VASP-HIS$_6$

The pzmp21B7R1VASP-His$_6$ vector was transfected into BHK570 cells using Lipofectamine 2000 according to manufacturer's protocol (Invitrogen, Carlsbad, Calif.) and the cultures were selected for transfectants resistance to 10 μM methotrexate. Resistant colonies were transferred to tissue culture dishes, expanded and analyzed for secretion of B7R1VASP-His$_6$ by western blot analysis with Anti-His (C-terminal) Antibody (Invitrogen, Carlsbad, Calif.). The resulting cell line, BHK.B7R1VASP-His$_6$.2, was expanded.

A. Purification of B7R1VASP-His$_6$ from BHK Cells

The purification was performed at 4° C. About 2 L of conditioned media from BHK:B7R1VASP-His$_6$.2 was concentrated to 0.2 L using Pellicon-2 5 k filters (Millipore, Bedford, Mass.), then buffer-exchanged tenfold with 20 mM NaPO$_4$, 0.5M NaCl, 15 mM Imidazole, pH 7.5. The final 0.2 L sample was passed-through a 0.2 mm filter (Millipore, Bedford, Mass.).

A Talon (BD Biosciences, San Diego, Calif.) column with a 20 mL bed-volume was packed and equilibrated with 20 mM NaPi, 15 mM Imidazole, 0.5 M NaCl, pH 7.5. The media was loaded onto the column at a flow-rate of 0.2-0.4 mL/min then washed with 5-6 CV of the equilibration buffer. B7R1VASP-His$_6$ was eluted from the column with 20 mM NaPO$_4$, 0.5 M NaCl, 0.5 M Imidazole, pH 7.5 at a flow-rate of 4 mL/min. 10 mL fractions were collected and analyzed for the presence of B7R1VASP-His$_6$ by Coomassie-stained SDS-PAGE.

A combined pool of Talon eluates obtained from three identical runs as described above was concentrated from 60 mL to 3 mL using an Amicon Ultra 5 k centrifugal filter (Millipore, Bedford, Mass.). A Superdex 200 column with a bed-volume of 318 mL was equilibrated with 50 mM NaPi, 110 mM NaCl, pH 7.3, and the 3 mL sample was injected into the column at a flow-rate of 0.5 mL/min. Two 280 nm absorbance peaks were observed eluting from the column, one at 0.38 CV and the other at 0.44 CV. The fractions eluting around 0.44 CV, believed to contain tetrameric B7R1VASP-His$_6$, were pooled and concentrated, sterile-filtered through a 0.2 mm Acrodisc filter (Pall Corporation, East Hills, N.Y.), and stored at −80° C. Concentration of the final sample was determined by BCA (Pierce, Rockford, Ill.).

B. SEC-MALS Analysis of B7R1VASP-CH6

The purpose of size exclusion chromatography (SEC) is to separate molecules on the basis of size for estimation of molecular weight (Mw). If static light scattering detection is added to a SEC system, absolute measurements of molecular weight can be made. This is possible because the intensity of light scattered by the analyte is directly proportional to its mass and concentration, and is completely independent of SEC elution position, conformation or interaction with the column matrix. Additionally, by combining SEC, multi-angle laser light scattering (MALS) and refractive index detection (RI), the molecular mass, association state, and degree of glycosylation can be determined. The limit of accuracy of these measurements for a sample that is monodisperse with respect to Mw is ±2%.

Example 11

CD155 Binds Soluble zB7R1

A soluble form of zB7R1 was produced either as an in-frame fusion with a mouse Fc-region or with the tetramerization domain from the Vasp protein (both of which are described herein). These proteins were labeled with either biotin or conjugated to a fluorochrome for use as a FACS reagent or for fluorescence microscopy. These reagents were used to interrogate a variety of primary cell types from mouse bone marrow and spleen for binding. Dendritic cells (DC's) from bone marrow grown seven days in Flt-3 ligand (Flt3L) and then activated with CD40 ligand (CD40L) and interferon-g (IFNg) were found to bind fluorochrome conjugated or biotinylated forms of both zB7R1 proteins. An expression library was produced from this activated DC population and this library was introduced into COS cells by transient transfection. Transfected pools of cells were then screened for zB7R1 binding using the biotinylated ZB7r1-Vasp protein and fluorescence microscopy. Positive pools were broken down systematically until a single plasmid was recovered that conveyed binding activity. Nucleic acid sequencing revealed this plasmid encoded the mouse homolog of the human poliovirus receptor (PVR), CD155 (SEQ ID NOs:17 and 18). CD155 binds zB7R1 transfected cells and, thus, it is one counter-receptor now known to bind zB7R1.

Example 12

VASP-zB7R1 Expression for the Secretion Trap Assay

Three sets of 50 μg of the mzB7R1/Vasp fusion protein construct were each digested with 50 units of Pvu I at 37° C. for three hours and then were precipitated with IPA and spun down in a 1.5 mL microfuge tube. The supernatant was decanted off the pellet, and the pellet was washed with 1 mL of 70% ethanol and allowed to incubate for 5 minutes at room temperature. The tube was spun in a microfuge for 10 minutes at 14,000 RPM and the supernatant was decanted off the pellet. The pellet was then resuspended in 750 μl of PF-CHO media in a sterile environment, allowed to incubate at 60° C. for 30 minutes, and was allowed to cool to room temperature. 5E6 APFDXB11 cells were spun down in each of three tubes and were resuspended using the DNA-media solution. The DNA/cell mixtures were placed in a 0.4 cm gap cuvette and electroporated using the following parameters: 950 high capacitance, and 300 V. The contents of the cuvettes were then removed, pooled, and diluted to 25 mLs with PF-CHO media and placed in a 125 mL shake flask. The flask was placed in an incubator on a shaker at 37° C., 6% CO$_2$, and shaking at 120 RPM.

The cell line was subjected to nutrient selection followed by step amplification to 200 nM methotrexate (MTX), and then to 500 nM MTX. Expression was confirmed by western blot, and the cell line was scaled-up and protein purification followed.

Example 13

Use of VASP-zB7R1 Fusion Protein to Screen for Ligands zB7R1VASP fusion protein was made as described in the above Example 12. This protein was then used to screen for its corresponding ligand as described below.

A) Screening of the mBMDC Library:

A secretion trap assay was used to pair mzB7R1 to mCD155 (SEQ ID NO:18). The soluble mzB7R1/Vasp fusion protein that had been biotinylated was used as a binding reagent in a secretion trap assay. A pZP-7NX cDNA library from stimulated mouse bone marrow (mBMDC) was transiently transfected into COS cells in pools of 800 clones. The binding of mzB7R1/Vasp-biotin to transfected COS cells was carried out using the secretion trap assay described below. Positive binding was seen in 26 of 72 pools screened. One of these pools was selected and electroporated into DR10B. 400 single colonies were picked into 1.2 mls LB+100 ug/ml ampicillin in deep well 96-well blocks, grown overnight followed by DNA isolation from each plate. After transfection and secretion trap probe, a single positive well was identified from this breakdown and submitted to sequencing and was identified as being mCD155. This purified cDNA was transfected and probed with mB7R1/Vasp-biotin along with additional controls to verify that mCD155 specifically and reproducibly bound mB7R1/Vasp-biotin but not other Vasp chimeras.

B) COS Cell Transfections

The COS cell transfection was performed as follows: Mix 1 ug pooled DNA in 25 ul of serum free DMEM media (500 mls DMEM with 5 mls non-essential amino acids) and 1 ul Cosfectin™ in 25 ul serum free DMEM media. The diluted DNA and cosfectin are then combined followed by incubating at room temperature for 30 minutes. Add this 50 ul mixture onto $8.5 \times 10^5$ COS cells/well that had been plated on the previous day in 12-well tissue culture plates and incubate overnight at 37° C.

C) Secretion Trap Assay

The secretion trap was performed as follows: Media was aspirated from the wells and then the cells were fixed for 15 minutes with 1.8% formaldehyde in PBS. Cells were then washed with TNT (0.1M Tris-HCL, 0.15M NaCl, and 0.05% Tween-20 in $H_2O$), and permeabilized with 0.1% Triton-X in PBS for 15 minutes, and again washed with TNT. Cells were blocked for 1 hour with TNB (0.1M Tris-HCL, 0.15M NaCl and 0.5% Blocking Reagent (NEN Renaissance TSA-Direct Kit) in $H_2O$), and washed again with TNT. The cells were incubated for 1 hour with 2 µg/ml mzB7R1/Vasp-biotin soluble receptor fusion protein. Cells were then washed with TNT. Cells were fixed a second time for 15 minutes with 1.8% formaldehyde in PBS. After washing with TNT, cells were incubated for another hour with 1:1000 diluted streptavidin HRP. Again cells were washed with TNT.

Positive binding was detected with fluorescein tyramide reagent diluted 1:50 in dilution buffer (NEN kit) and incubated for 5 minutes, and washed with TNT. Cells were preserved with Vectashield Mounting Media (Vector Labs Burlingame, Calif.) diluted 1:5 in TNT. Cells were visualized using a FITC filter on fluorescent microscope.

Example 14

Biological Activity of the VASP-zB7R1 Fusion Protein

T-cells are isolated from peripheral blood by negative selection (Mitenyi Biotec, Auburn, Calif.). T-cells are plated into each well of a 96 well dish that had been pre-coated with anti-CD3 (BD Bioscience, San Diego, Calif.). Anti-CD28 (BD Bioscience, San Diego, Calif.), and increasing concentration of zB7R1/VASP are added to appropriate wells. The cultures are incubated at 37° C. for 4 days and then labeled overnight with 1 □Ci [$^3$H] thymidine per well. Proliferation is measured as [$^3$H] thymidine incorporated, and culture cytokine content is quantitated using Luminex (Austen, Tex.). zB7R1/VASP does potently inhibit both T-cell proliferation and cytokine release (Dong et al., Nature Med. 5: 1365-1369, 1999).

Example 15 zB7R1 Monoclonal Antibodies

BALB/c mice were immunized with DNA encoding the human zB7R1 extracellular domain (SEQ ID NO:3) expressed as a membrane protein. Mice with positive serum titers to cellular expressed human zB7R1 were given a prefusion boost of soluble zB7R1-Fc fusion protein.

Splenocytes were harvested from one high-titer mouse and fused to P3-X63-Ag8/ATCC (mouse) myeloma cells in an optimized PEG-mediated fusion protocol (Rockland Immunochemicals). Following 9 days growth post-fusion, specific antibody-producing hybridoma pools were identified by ELISA using 500 ng/ml each of the purified recombinant fusion protein zB7R1-mFc2 as the specific antibody target and a pTACI mFc2 fusion protein as a non-specific antibody target. To check for cross-reactivity, the samples were also checked against mouse zB7R1. Hybridoma pools positive to the specific antibody target only were analyzed further for ability to bind via FACS analysis to p815/zB7R1 cells as antibody target.

Hybridoma pools yielding a specific positive result in the ELISA assay and positive results in the FACS assay were cloned at least two times by limiting dilution.

The following five clones were harvested and purified for use in assays: 318.4.1.1, 318.28.2.1, 318.39.1.1, 318.59.3.1, 318.77.1.10

Example 16

Bioassays for the Detection of Anti-zB7R1 Signaling Antibodies

In an effort to develop an assay that could be used to detect and evaluate signaling antibodies, a Baf3-STAT-luciferase reporter cell line was constructed expressing a chimera of the extracellular domain of the molecule of interest (i.e. zB7R1), and the transmembrane and intracellular domains of mouse GCSFR. Antibodies against the molecule of interest may mediate dimerization of their target molecule on the cell surface, leading in turn to the dimerization of the mGCSFR intracellular domains and consequent phosphorylation of STAT signaling molecules. These phosphorylated STATs then migrate to the nucleus where they bind to STAT responsive elements located on a recombinant, enhancer/promoter/cDNA construct. This binding results in the transcription and synthesis of a luciferase protein that can be measured quantitatively utilizing a simple assay.

The assay cell line was constructed by placing an expression vector (pZMP21Z) containing the human zB7R1/mGCSFR chimera, into a previously utilized BaF3/KZ134 cell line. This expression vector and subsequent cell line were built using the following steps.

Generation of Human zB7R1 Extracellular Domain and Mouse GCSFr Transmembrane and Intracellular Domain PCR Products A 465 bp, human B7r1 extracellular domain, DNA fragment was created by PCR using Expand reagents (Roche, Applied Sciences, Indianapolis, Ind.), and ZC53051 (SEQ ID NO:55) and ZC54199 (SEQ ID NO:56). These zB7R1 amplification primers added complimentary regions to mGCSFR and the pZMP21 vector allowing for overlap PCR and yeast recombination respectively.

A 1562 bp transmembrane and intracellular domain mouse GCSFr DNA fragment was created by PCR using Expand reagents (Roche, Applied Sciences, Indianapolis, Ind.), and ZC54198 (SEQ ID NO:57) and ZC53248 (SEQ ID NO:58) These mGCSF amplification primers added complimentary regions to hB7R1 and the pZMP21 vector allowing for overlap PCR and yeast recombination respectively.

Generation of Human zB7R1-m.GCSFr Overlap PCR Product for Use in Yeast Recombination Plasmids containing the zB7r1 and mouse GCSFr cDNAs were used as templates. PCR amplification of the zB7r1 and mouse GCSFr fragments were performed as follows: One cycle of 95° C. for 2 minutes; then thirty cycles at 95° C. for 30 seconds, 56° C. for 30 seconds, 72° C. for 1.5 minutes, followed by one cycle of 72° C. for 7 minutes and then a 4° C. hold. The reactions were visualized on a 1.2% agarose gel and the appropriate bands were excised and purified using QIAquick Gel Extraction kit (Qiagen, Santa Clarita, Ca.)

The zB7R1 and mouse GCSFr purified PCR products were used as templates in an overlap PCR reaction to create a chimeric B7r1-m.GCSFr product of 1995 bp. Expand reagents (Roche, Applied Sciences, Indianapolis, Ind.), and ZC53051 (SEQ ID NO:59) and ZC53248 (SEQ ID NO:60) as PCR primers were used.

PCR amplification of the B7r1-mouse GCSFr fragment was performed as follows: One cycle of 95° C. for 2 minutes; then thirty cycles at 95° C. for 30 seconds, 56° C. for 30 seconds, 72° C. for 1.5 minutes, followed by one cycle of 72° C. for 7 minutes and a 4° C. hold. The reaction was visualized on a 1.2% agarose gel and the appropriate band was excised and purified using QIAquick Gel Extraction kit (Qiagen, Santa Clarita, Calif.)

Yeast Recombination of Human zB7R1-m.GCSFr Purified PCR Product into pZMP21Z

Competent yeast cells strain SF838-9D□□ were thawed on ice. One μl of pZMP21Z vector digested with BglII by standard restriction digest methods was mixed with 6 μl h.zB7r1-m.GCSFR purified PCR product, or 6 μl TE buffer as a negative control. The DNA mixture was added to 45 μl yeast cells, mixed and transferred to separate 2 mm disposable electroporation chambers (VWR, West Chester, Pa.). Cells were electroporated using a Biorad Genepulser (Hercules, Calif.) set to 750 V, 25 μFD, infinite resistance. 600 μl cold 1.2 M sorbitol was immediately added to each chamber. 150 μl and 300 μl from each chamber was plated on -URA DS agar plates and incubated for 72 hours at 30° C. Yeast colonies from each plate were suspended in 1 ml $H_2O$ and transferred to 1.5 ml eppendorf tubes. Cells were pelleted by centrifugation and the supernatant was removed. An amount equivalent to 50 μl packed yeast of each sample was transferred to another 1.5 ml eppendorf tube and resuspended in 100 μl Yeast Lysis Buffer (25 Triton X, 1% SDS, 100 mM NaCl, 10 mM Tris HCl, pH8.0, 1 mM EDTA). To each tube 2 μl (10 U) Zymolase (Zymo Research, Cat #E1001/E1002) was added followed by a 30 minute incubation at 37° C. The lysed cells were miniprepped by adding 150 μl Buffer P1 (Qiagen) and then proceeding with the QIAprep Spin Miniprep Kit at step 2. Plasmid DNA thus purified from yeast was electroporated into DH10b Electormax cells (Invitrogen, Carlsbad, Calif.) following the manufacturers recommendations. Clones were isolated, sequenced, and large scale plasmid isolations were preformed using standard methods.

Construction of BaF3/KZ134 Cells Expressing Chimeric Human zB7R1-Mouse GCSFr

BaF3, an interleukin-3 (IL-3) dependent prelymphoid cell line derived from murine bone marrow (Palacios and Steinmetz, Cell 41: 727-734, 1985; Mathey-Prevot et al., Mol. Cell. Biol. 6: 4133-4135, 1986), was maintained in complete media (RPMI medium (JRH Bioscience Inc., Lenexa, Kans.) supplemented with 10% heat-inactivated fetal calf serum, 2 ng/ml murine IL-3 (mIL-3) (R+D, Minneapolis, Minn.), 2 mM L-glutamine (Gibco-BRL), and 1 mM Sodium Pyruvate (Gibco-BRL).

The KZ134 plasmid was constructed with complementary oligonucleotides that contain STAT transcription factor binding elements from 4 genes, which includes a modified c-fos Sis inducible element (m67SIE, or hSIE) (Sadowski, h. et al., Science 261: 1739-1744, 1993) the p21 SIE1 from the p21 WAF1 gene (Chin, Y. et al., Science 272: 719-722, 1996), the mammary gland response element of the □-casein gene (Schmitt-Ney, M. et al., Mol. Cell. Biol. 11:3745-3755, 1991), and a STAT inducible element of the Fcγ RI gene, (Seidel, H. et al., Proc. Natl. Acad. Sci. 92:3041-3045, 1995). These oligonucleotides contain Asp718-XhoI compatible ends and were ligated, using standard methods, into a recipient firefly luciferase reporter vector with a c-fos promoter (Poulsen, L. K. et al., J. Biol. Chem. 273:6229-6232, 1998) digested with the same enzymes and containing a neomycin selectable marker. The KZ134 plasmid was used to stably transfect BaF3 cells, using standard transfection and selection methods, to make the BaF3/KZ134 cell line.

BaF3/KZ134 cells were prepared for electroporation by washing twice in RPMI medium (JRH Bioscience Inc., Lenexa, Kans.) and then resuspending in RPMI at a cell density of $10^7$ cells/ml. One ml of resuspended BaF3 cells was mixed with 30 μg of the pZPMPZ/h.zB7r1-m.GCSFr plasmid DNA and transferred to separate disposable electroporation chambers (Gibco-BRL). The cells were then given 2 serial shocks (800 lFad/300V; 1180 lFad/300V.) delivered by an electroporation apparatus (CELL-PORATOR™; Gibco-BRL, Bethesda, Md.). The electroporated cells were subsequently transferred to 20 mls of complete media containing 2 μg/ml Puromycin (Clontech, Palo Alto, Calif.) and placed in an incubator for 24 hours (37° C., 5% $CO_2$). The cells were then spun down and resuspended in 20 mls of complete media containing μg/ml Puromycin and 240 μg/ml Zeocin (Invitrogen, Carlsbad, Calif.) selection in a T75 flask to isolate the Zeocin resistant pool. The resulting stable cell line was called BaF3/KZ134/h.zB7r1-m.GCSFr.

HzB7R1 Antibodies Specifically Activate STAT Signaling in BaF3/KZ134/h.B7r1-m.GCSFr Cells The antibodies tested on the BaF3/KZ134/h.B7r1-m.GCSFr cells were: mouse anti-human zB7r1 318.4.1.1 (E9310), 318.28.2.1 (E9296), 318.39.1.1 (E9311), 318.59.3.1 (E9400). These antibodies were coupled to Dynabeads M-450 Tosylactivated, (Dynal Biotech ASA, Oslo, Norway) as follows: 50 μl ($2 \times 10^7$ beads) per sample was washed once with 1 ml 0.1M sodium phosphate buffer, pH7.4-8.0 in a 2.0 ml eppendorf tube. The tube was placed in a magnet for 1 minute and the supernatant was removed. The beads were resuspended in the original volume using the sodium phosphate buffer. 10 μg of each antibody was combined with 50 μl washed beads in 2.0 ml eppendorf tubes. A beads only (no antibody) control was included. The tubes were placed on a Clay Adams Nutator mixer (Bectin-Dickinson, Franklin Lakes, N.J.) at room temperature for 48 hours. The tubes were then placed in a magnet for 1 minute and the supernatant was removed. The coated beads were then washed 4 times with 1 ml PBS (without Ca2+ and Mg2+), 0.1% BSA (w/v) and 2 mM EDTA, pH 7.4.

In setting up the cell assay, the coated beads and a beads only control were plated in Falcon U-bottomed 96 well plates (Bectin-Dickinson, Franklin Lakes, N.J.) at concentrations of 480,000, 240,000, 120,000, 60,000, 30,000, 15,000, and 7500 beads per well in 100 µl. Unbound antibody was also plated at concentrations of 2, 1, 0.5, 0.25, 0.13, 0.6, and 0.3 µg/ml in 100 µl. Each sample was plated in triplicate. As a positive control for STAT signaling, mouse IL3 dilutions were included at concentrations of 2, 1, 0.5, 0.25, 0.13, 0.6, and 0.3 pg/ml in 100 µl.

The BaF3/KZ134/h.B7r1-m.GCSFr Zeocin resistant cells were washed three times in RPMI and counted using a hemocytometer. Cells were resuspended in RPMI and plated at a concentration of 30,000 cells per well in 100 µl into the plate containing the samples for total well volume of 200 µl.

The assay was incubated at 37° C., 5% $CO_2$ for 24 hours at which time the BaF3 cells were pelleted by centrifugation at 1500 rpm for 10 min., the media was aspirated and 25 µl of lysis buffer (Promega) was added. After allowing 10 minutes for cell lysis at room temperature, the plates were measured for activation of the STAT reporter construct by reading them on a luminometer (EG&G Berthold, model Microlumat Plus LB 96V) which added 40 µl of luciferase assay substrate (Promega) and measured the light generated in the 10 seconds following substrate addition.

The results of this assay showed that the B7r1 antibody-bead complex bound to the B7r1-m.GCSFr in a dose dependent manner and caused dimerization leading to STAT formation and signal transduction. Neither unbound antibodies nor undecorated beads elicited a STAT response.

In this example, the extracellular domain of a B7 family type I protein (B7r1) and the transmembrane and intracellular domain of a type I cytokine receptor superfamily protein (GCSFR) were expressed as a chimera and induced dimerization and STAT signaling when exposed to antibody. This method may also be used with chimeras from other receptor families. Examples of chimeras utilizing mouse GCSFr for signaling have included the extracellular ligand binding domains of CD28, zTNFR14, and Fas, among others. Variations on this method could be used with chimeras from other receptor families paired with cells line assays sensitive to appropriate signaling pathways. Examples may include chimeras signaling through the NFkB pathway. These chimeras may be expressed in NIH3T3 cells also expressing an NFkB responsive promoter fused to a luciferase cDNA plasmid such as KZ142. These chimeras may be built with the transmembrane and intracellular domain of a TNF family molecule such as pTNFRSF4, known to signal through NFkB, and could include the extracellular domain of molecules such as B7r1, CD28, TNFR14, and Fas, among others.

Additional in vitro assays utilizing chimeric receptors will be useful in examining the signaling properties of the zB7R1 intracellular domain and in identifying antibodies directed against the extracellular domain that mediate signaling. The type of cell signal that the zB7R1 intracellular domain generates in response to ligand binding may be elucidated in the following way. The extracellular domain of hCD28, a B7 family member, is fused to the transmembrane and intracellular domains of murine zB7R1. This chimera is then transfected into the murine T cell hybridoma cell line, Tea. This murine cell line responds to T cell receptor (TCR) ligation by secreting IL2. Some B7 family members have been shown to modify the magnitude of the T cell response; for example, simultaneous ligation of CD28 alongside CD3 (TCR) yields a significant increase in IL2 secretion over CD3 ligation alone. Utilizing this chimera, antibodies directed against the human CD28 extracellular domain may mediate the ligation of mzB7R1 intracellular domain and subsequent signaling. IL2 levels may be quantitated by ELISA in in vitro CD3/CD28 costimulation assays revealing the nature of the hzB7R1 signaling domain.

Additionally, human zB7R1 extracellular domains may be fused with mCD28 intracellular domains in TEa hybridomas. Such chimeras would allow for the screening of antibodies or other ligands directed against the zB7R1 extracellular domain. This binding may result in dimerization and signaling through the mCD28 intracellular domain that would likely increase IL2 secretion. Such screening for molecules active on the zB7R1 extracellular domain may thus be initiated prior to a complete understanding of the zB7R1 signaling mechanism.

Example 17 zB7R1 Expression on Human PBMNC

In order to culture the cells, blood from normal in-house donors was separated on a ficol gradient, and the PBMNC interface collected and washed in PBS. The cells were counted and plated in 96 well round bottom plates at $2e^5$ cells/well in 200 µl culture medium with either LPS at 100 ng/ml or with anti-CD3+ anti-CD28 mabs (50 ng/ml and 1 µg/ml respectively). Some cells were reserved for the time 0 timepoint. Cells were collected for staining at times 24, 48 and 72 hours.

At each timepoint, cells in 96 well plates are spun, the media flicked out, and a combination of fluor-conjugated antibodies to surface lineage markers added in 50 µl Facs staining buffer (CD56-A488, CD19-PE, CD45RA-Cychrome, CD45RO-PE-Cy7, CD4-A405, CD8-A700, and CD14-A750). The combination included either mab anti-B7R1 (318.4.1) coupled to A647 dye, or a control mab similarly coupled. In some experiments, the binding of mab anti-B7R1 was competed with 20 fold (g/g) excess mB7R1 receptor. Each condition was stained in triplicate wells. Cells were incubated with a stain combo for 30 minutes on ice, then are washed 1.5× with Facs buffer and fixed with 2% paraformaldehyde, 100 ul/well, for 10 minutes, at room temp. Plates were spun, the paraformaldehyde flicked out, and cells resuspended in 200 ul Facs buffer and stored at 4 C. foil-covered until they were read on the LSRII.

The LSRII data was analyzed using FacsDiva software. FSC X SSC dot plots were used to determine a viable cell population gate. Viable cells were then analyzed for anti-B7R1 binding using dot plots of anti-B7R1-A647 vs specific lineage markers.

For the kinetic analysis of B7R1 expression, the background fluorescence (either determined with the control mab-A647 or with blocking using 20×g/g soluble receptor) was subtracted from the anti-B7R1-A647 staining for each lineage over time.

The results indicated that zB7R1 is expressed on resting CD8+ and NK cells and that expression is upregulated with activation on CD4+, CD8+ and NK cells. There is no detectable binding on CD19+ and there is no competable binding to CD14+ or CD11c cells. Expression of zB7R1 was higher on memory T cells relative to naive T cells.

Example 18

T-Cell Proliferation is Inhibited by zB7R1 Antibodies

The proliferation of purified CD4 and CD8 T cells from human peripheral blood mononuclear cells (PBMC) was inhibited by antibody to zB7r1 in vitro. An antibody to CD3 (BD Biosciences 555329) mimicked T cell antigen recognition. Engagement of CD3 and the T cell receptor by antibody provided a signal to proliferate in vitro. This signal was enhanced or inhibited by additional signals. An antibody to zB7r1, covalently coupled to tosylactivated 4.5 □ beads (Dynal 140.13), inhibited the anti-CD3-induced proliferation of T cells in vitro. The addition of co-stimulatory anti-CD28 (BD Biosciences 555725) did not overcome the inhibitory effect of anti-zB7r1. Moreover, anti-zB7r1 inhibited the expression of the early activation markers CD69 and the IL-2 receptor CD25 as well as the production of IL-2.

Tosylactivated beads were used as a solid phase platform to present anti-CD3 and anti-zB7r1 to T cells. Human PBMC from healthy volunteers were collected by Ficoll-Paque (GE Healthcare) density gradient. CD4 and CD8 were co-purified from PBMC by magnetic bead columns (Miltenyi Biotec). T cells were labeled with CFSE (Invitrogen) to assess proliferation by flow cytometry. 1×10E5 CFSE-labeled T cells and 1×10E5 beads were plated per well. Cultures were maintained for 1 day to assess early activation markers or 3 days to assess proliferation in humidified incubators at 5% $CO_2$. Proliferation of CD4s and CD8s was measured on an LSRII (Becton Dickinson).

Anti-zB7r1 inhibited CD4 memory and naïve T cells equivalently. Specifically, CD4 T cells were purified as before then sorted into CD45RA high (naïve) and CD45RA low (memory) populations via cell sorting on the FACSAria (BD Biosciences). Cells were cultured as above then assessed for proliferation at 72 hr. Anti-CD3 was titrated in combination with fixed amount of zb7r1, control or anti-CTLA4. CD4 memory and naïve cells were inhibited in proliferation to an equivalent extent.

Anti-zB7r1 inhibited IL-2 production by memory and naïve CD4s. Specifically, IL-2 production of CD3-activated memory and naïve CD4 cells is inhibited by anti-zB7r1. T cells and beads were cultured as above. IL-2 production at 24h was assessed in culture supernatants by Luminex technology (Bio-Rad).

Example 19 zB7R1-VASP in Acute Graft Versus Host Disease (GVHD)

The purpose of this experiment was to determine if prophylactic treatment of B7R1-VASP soluble protein influences the development and severity of an acute GVHD response in mice.

To initiate GVHD, 75 million spleen cells from C57Bl/6 mice are injected by intravenous delivery into DBA2x C57Bl/6 F1 mice (BDF1) on day 0. Mice are treated with 150 µg of B7R1-VASP protein intraperitoneally every other day starting the day before cell transfer and continuing throughout the duration of the experiment. Body weight is monitored daily and mice are sacrificed on day 12 after spleen transfer. Spleens are collected for FACS analysis and blood is collected for serum.

Prophylactic delivery of B7R1-VASP significantly decreases the severity of body weight loss during acute GVHD.

Example 20

Delayed Type Hypersensitivity in zB7R1-Fc-Treated Mice

Delayed Type Hypersensitivity (DTH) is a measure of T cell responses to specific antigen. In this response, mice are immunized with a specific protein in adjuvant (e.g., chicken ovalbumin, OVA) and then later challenged with the same antigen (without adjuvant) in the ear. Increase in ear thickness (measured with calipers) after the challenge is a measure of specific immune response to the antigen. DTH is a form of cell-mediated immunity that occurs in three distinct phases 1) the cognitive phase, in which T cells recognize foreign protein antigens presented on the surface of antigen presenting cells (APCs), 2) the activation/sensitization phase, in which T cells secrete cytokines (especially interferon-gamma; IFN-γ) and proliferate, and 3) the effector phase, which includes both inflammation (including infiltration of activated macrophages and neutrophils) and the ultimate resolution of the infection. This reaction is the primary defense mechanism against intracellular bacteria, and can be induced by soluble protein antigens or chemically reactive haptens. A classical DTH response occurs in individuals challenged with purified protein derivative (PPD) from *Mycobacterium tuberculosis*, when those individuals injected have recovered from primary TB or have been vaccinated against TB. Induration, the hallmark of DTH, is detectable by about 18 hours after injection of antigen and is maximal by 24-72 hours. The lag in the onset of palpable induration is the reason for naming the response "delayed type." In all species, DTH reactions are critically dependent on the presence of antigen-sensitized CD4+(and, to a lesser extent, CD8+) T cells, which produce the principal initiating cytokine involved in DTH, IFN-γ.

In order to test for anti-inflammatory effects of mB7R1-Fc, a DTH experiment was conducted with six groups of C57Bl/6 mice treated with: I) control plasmid, II) 25 ug mCTLA-4-Fc plasmid, and III) 25 ug mB7R1-Fc plasmid. All of these plasmids were injected hydrodynamically through the tail vein. In short, 25 ug of plasmid was resuspended in 2 mL of sterile injectable saline. Each mouse received a single intravenous injection of 2 mL saline containing 25 ug plasmid via its tail vein. Injections were accomplished within 4-8 seconds/mouse, leading to the hydrodynamic pressure that results in cellular transfection in multiple organs in the mouse. Treatments were given one day prior to the OVA/RIBI sensitization (groups 1-3) or one day prior to OVA re-challenge (groups 4-6). The mice (6 per group) were first immunized in the back with 100 µg chicken ovalbumin (OVA) emulsified in Ribi in a total volume of 200 ul. Seven days later, the mice were re-challenged intradermally in the left ear with 10 ul PBS (control) or in the right ear with 10 µg OVA in PBS (no adjuvant) in a volume of 10 ul. Ear thickness of all mice was measured before injecting mice in the ear (0 measurement). Ear thickness was measured 24, and 48 hours after challenge. The difference in ear thickness between the 0 measurement and the 24 hour measurement is shown in TABLE 1. Control mice in the control plasmid treatment group developed a strong DTH reaction as shown by increase in the ear thickness at 24 and 48 hours post-challenge. In contrast, mice treated with CTLA-4Fc or B7R1Fc at the challenge phase had a lesser degree of ear thickness compared to controls. B7R1-Fc injection also inhibited ear thickness at the sensitization phase but only at the 24 hr time point. These differences were statistically significant, as determined by Student's t-test (Table 5, p values vs. control plasmid).

TABLE 5 zB7R1 inhibits the Delayed Type Hypersensitivity (DTH) reaction when administered either at the challenge or at the sensitization phase of the response

| EXPT # | TREATMENT | TIME/ ROUTE OF TREATMENT | CHANGE IN EAR THICKNESS ($\times 10^{-3}$ inch) | | p value vs. control |
|---|---|---|---|---|---|
| | | | LEFT EAR (PBS) | RIGHT EAR (OVA) | |
| | | | 24 hr | 24 hr | |
| 1 (n = 6) | Control plasmid | Sensitization (d-1) | 0.42 +/− 0.80 | 6.72 +/− 1.04 | — |
| | mCTLA-4-Fc | i.v. | 0.5 +/− 0.63 | 7.11 +/− 2.69 | 0.7484 |
| | mB7R1-Fc | | 1.19 +/− 0.54 | 4.44 +/− 0.86 | 0.002 |
| | Control plasmid | Challenge (d6) | 0.08 +/− 0.66 | 10 +/− 1.84 | — |
| | mCTLA-4-Fc | i.v. | 0.55 +/− 0.08 | 5.94 +/− 0.78 | 0.0006 |
| | mB7R1-Fc | | 0.65 +/− 0.62 | 7.08 +/− 1.28 | 0.0099 |
| | | | 48 hr | 48 hr | |
| 1 (n = 6) | Control plasmid | Sensitization (d-1) | 0.2 +/− 0.54 | 5.91 +/− 1.3 | — |
| | mCTLA-4-Fc | i.v. | 0.66 +/− 0.40 | 7.69 +/− 2.69 | 0.1758 |
| | mB7R1-Fc | | 0.94 +/− 0.88 | 6.33 +/− 1.12 | 0.5650 |
| | Control plasmid | Challenge (d6) | 0.55 +/− 0.62 | 11.38 +/− 2.67 | — |
| | mCTLA-4-Fc | i.v. | 0.05 +/− 0.08 | 6.97 +/− 1.26 | 0.0045 |
| | mB7R1-Fc | | 0.05 +/− 0.13 | 6.30 +/− 0.96 | 0.0014 |

Example 21

B7R1 is Regulated in Tissues from Mice with Collagen Induced Arthritis (CIA) Compared to Non-Disease Tissue Experimental Protocol: Tissues were obtained from mice with varying degrees of disease in the collagen-induced arthritis (CIA) model. The model was performed following standard procedures of immunizing male DBA/1J mice with collagen (see Example 22 below) and included appropriate non-diseased controls. Tissues isolated included affected paws and popliteal lymph nodes. RNA was isolated from all tissues using standard procedures. In brief, tissues were collected and immediately frozen in liquid N2 and then transferred to −80° C. until processing. For processing, tissues were placed in Qiazol reagent (Qiagen, Valencia, Calif.) and RNA was isolated using the Qiagen Rneasy kit according to manufacturer's recommendations. Expression of murine zB7R1 mRNA was measured with multiplex real-time quantitative RT-PCR methods (TaqMan) and the ABI PRISM 7900 sequence detection system (PE Applied Biosystems). Murine zB7R1 mRNA levels were normalized to the expression of murine hypoxanthine guanine physphoribosyl transferase mRNA and determined by the comparative threshold cycle method (User Bullein 2: PE Applied Biosystems). The primers and probe for murine B7R1 included forward primer 5' SEQ ID NO:65, reverse primer 5' SEQ ID NO:66, and probe SEQ ID NO:67.

Results: Murine B7R1 mRNA expression was detected in the tissues tested. Higher levels of expression were observed in lymph nodes compared to the paws. B7R1 mRNA was increased in the popliteal lymph nodes and the paws from mice in the CIA model of arthritis compared to tissues obtained from non-diseased controls, and the levels were associated with disease severity. B7R1 mRNA was increased in the paws approximately 2.3-fold in mice with mild disease and approximately 4-fold in mice with severe disease compared to non-diseased controls. B7R1 mRNA was increased in the lymph node approximately 1.5-fold in mice with mild disease and approximately 1.8-fold in mice with severe disease compared to non-diseased controls.

Example 22

B7R1m-mFc and B7R1m-VASP CH6 Decreases Disease Incidence and Progression in Mouse Collagen Induced Arthritis (CIA) Model Mouse Collagen Induced Arthritis (CIA) Model: Ten week old male DBA/1J mice (Jackson Labs) were divided into 3 groups of 13 mice/group. On day-21, animals were given an intradermal tail injection of 50-100 µl of 1 mg/ml chick Type II collagen formulated in Complete Freund's Adjuvant (prepared by Chondrex, Redmond, Wash.), and three weeks later on Day 0 they were given the same injection except prepared in Incomplete Freund's Adjuvant. B7R1m-mFc or B7R1m-VASP CH6 was administered as an intraperitoneal injection every other day for 1.5 weeks (although dosing may be extended to as must as four weeks), at different time points ranging from Day −1 to a day in which the majority of mice exhibit moderate symptoms of disease. Groups received 150 µg of B7R1m-mFc or B7R1m-VASP CH6 per animal per dose, and control groups received the vehicle control, PBS (Life Technologies, Rockville, Md.). Animals began to show symptoms of arthritis following the second collagen injection, with most animals developing inflammation within 1.5-3 weeks. The extent of disease was evaluated in each paw by using a caliper to measure paw thickness, and by assigning a clinical score (0-3) to each paw: 0=Normal, 0.5=Toe(s) inflamed, 1=Mild paw inflammation, 2=Moderate paw inflammation, and 3=Severe paw inflammation as detailed below.

Monitoring Disease: Animals can begin to show signs of paw inflammation soon after the second collagen injection, and some animals may even begin to have signs of toe inflammation prior to the second collagen injection. Most animals develop arthritis within 1-3 weeks of the boost injection, but some may require a longer period of time. Incidence of disease in this model is typically 95-100%, and 0-2 non-responders (determined after 6 weeks of observation) are typically seen in a study using 40 animals. Note that as inflammation begins, a common transient occurrence of variable low-grade paw or toe inflammation can occur. For this reason, an animal is not considered to have established disease until marked, persistent paw swelling has developed.

All animals were observed daily to assess the status of the disease in their paws, which is done by assigning a qualitative clinical score to each of the paws. Every day, each animal had its 4 paws scored according to its state of clinical disease. To determine the clinical score, the paw can be thought of as having 3 zones, the toes, the paw itself (manus or pes), and the wrist or ankle joint. The extent and severity of the inflammation relative to these zones was noted including: observation of each toe for swelling; torn nails or redness of toes; notation of any evidence of edema or redness in any of the paws; notation of any loss of fine anatomic demarcation of tendons or bones; evaluation of the wrist or ankle for any edema or redness; and notation if the inflammation extends proximally up the leg. A paw score of 1, 2, or 3 is based first on the overall impression of severity, and second on how many zones are involved. The scale used for clinical scoring is shown below.

Clinical Score:
0=Normal
0.5=One or more toes involved, but only the toes are inflamed
1=mild inflammation involving the paw (1 zone), and may include a toe or toes
2=moderate inflammation in the paw and may include some of the toes and/or the wrist/ankle (2 zones)
3=severe inflammation in the paw, wrist/ankle, and some or all of the toes (3 zones)

Established disease is defined as a qualitative score of paw inflammation ranking 2 or more, that persists for two days in a row. Once established disease is present, the date is recorded and designated as that animal's first day with "established disease".

Blood is collected throughout the experiment to monitor serum levels of anti-collagen antibodies, as well as serum immunoglobulin and cytokine levels. Serum anti-collagen antibodies correlate well with severity of disease. Animals are euthanized on a determined day, and blood collected for serum. From each animal, one affected paw may be?? collected in 10% NBF for histology and one is frozen in liquid nitrogen and stored at −80° C. for mRNA analysis. Also, ½ spleen, ½ thymus, ½ mesenteric lymph node, one liver lobe and the left kidney are collected in RNAlater for RNA analysis, and ½ spleen, ½ thymus, ½ mesenteric lymph node, the remaining liver, and the right kidney are collected in 10% NBF for histology. Serum is collected and frozen at −80° C. for immunoglobulin and cytokine assays.

Groups of mice that received soluble zB7R1-Fc fusion protein as described herein and zB7R1-VASP CH6 as described herein, at all time points tested (prophylactic and therapeutic delivery) were characterized by a delay in the incidence (for prophylactic administration), onset and/or progression of paw inflammation. On day 8 of the model, mice that received PBS prophylactically had 100% disease incidence and had significant swelling of the majority of their paws. However, mice that received zB7R1-Fc fusion protein prophylactically had significantly reduced paw swelling (2.3-fold lower arthritis score compared to PBS-treated mice) and 80% incidence. Moreover, mice treated prophlyactically with zB7R1-VASP CH6 fusion protein were greatly protected from disease, as only 40% of these mice developed arthritis symptoms, which was associated with markedly reduced arthritis scores (3.5-fold lower than PBS-treated mice). zB7R1-VASP CH6 fusion protein was also able to reduce arthritis symptoms when administered after disease onset, such that mice treated therapeutically with zB7R1-VASP CH6 fusion protein had approximately 2-fold lower arthritis scores than mice treated therapeutically with PBS. These results indicate that soluble zB7R1 fusion proteins of the present invention reduce inflammation, as well as disease incidence and progression.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of screening for an inhibitor of zB7R1 binding to CD155, comprising:
   a) providing an isolated first polypeptide comprising the extracellular domain of human zB7R1 (residues 16 - 140 of SEQ ID NO: 3) or an antigenic peptide thereof, or a first cell expressing the first polypeptide;
   b) exposing an isolated second polypeptide comprising the extracellular domain of human CD155 (SEQ ID NO: 19), or a second cell expressing the second polypeptide, to the first polypeptide or first cell in the presence of a test compound;
   c) determining the level of binding of the first polypeptide or first cell to the second polypeptide or second cell in the presence of the test compound;
   d) identifying the test compound as an inhibitor of the binding of zB7R1 to CD155 if and only if the level of binding determined in step c is less than the level of binding determined in the absence of the test compound under otherwise identical conditions.

2. The method of claim 1, wherein the test compound is:
   a) an antibody that specifically binds to the extracellular domain of human zB7R1(residues 16 - 140 of SEQ ID NO: 3) or an antigen binding fragment of the antibody; or
   b) an antibody that specifically binds to the extracellular domain of human CD155(SEQ ID NO: 19) or an antigen binding fragment of the antibody.

3. A method of determining the ability of a test compound to inhibit zB7R1 binding to CD155, comprising:
   a) providing an isolated first polypeptide comprising the extracellular domain of human zB7R1 (residues 16-140 of SEQ ID NO: 3) or an antigenic peptide thereof, or a first cell expressing the first polypeptide;
   b) exposing an isolated second polypeptide comprising the extracellular domain of human CD155 (SEQ ID NO: 19), or a second cell expressing the second polypeptide, to the first polypeptide or first cell in the presence of a test compound;
   c) determining the level of binding of the first polypeptide or first cell to the second polypeptide or second cell in the presence of the test compound;
   d) confirming that the test compound inhibits the binding of zB7R1 to CD155 if and only if the level of binding determined in step c is less than the level of binding determined in the absence of the test compound under otherwise identical conditions.

4. The method of claim 3, wherein the test compound is:
   a) an antibody that specifically binds to the extracellular domain of human zB7R1(residues 16-140 of SEQ ID NO: 3) or an antigen binding fragment of the antibody; or
   b) an antibody that specifically binds to the extracellular domain of human CD155(SEQ ID NO: 19) or an antigen binding fragment of the antibody.

5. The method of claim 1 wherein the antigenic peptide is selected from the group consisting of:
   a) amino acid residues 80 to 86 of SEQ ID NO:2;
   b) amino acid residues 163 to 170 of SEQ ID NO:2
   c) amino acid residues 163 to 190 of SEQ ID NO:2;
   d) amino acid residues 175 to 190 of SEQ ID NO:2 and
   e) amino acid residues 211 to 221 of SEQ ID NO:2.

6. The method of claim 3 wherein the antigenic peptide is selected from the group consisting of:
   a) amino acid residues 80 to 86 of SEQ ID NO:2;
   b) amino acid residues 163 to 170 of SEQ ID NO:2
   c) amino acid residues 163 to 190 of SEQ ID NO:2;
   d) amino acid residues 175 to 190 of SEQ ID NO:2 and
   e) amino acid residues 211 to 221 of SEQ ID NO:2.

7. The method of claim 1 wherein the first polypeptide comprises the extracellular domain of human zB7R1 (residues 16 -140 of SEQ ID NO: 3).

8. The method of claim 3 wherein the first polypeptide comprises the extracellular domain of human zB7R1 (residues 16 -140 of SEQ ID NO: 3).

9. The method of claim 1 wherein the level of binding is detected by surface plasmon resonance.

10. The method of claim 3 wherein the level of binding is detected by surface plasmon resonance.

11. The method of claim 2 wherein the test compound is an antibody that specifically binds to the extracellular domain of human zB7R1 (residues 16 -140 of SEQ ID NO: 3) or an antigen binding fragment of the antibody.

12. The method of claim 4 wherein the test compound is an antibody that specifically binds to the extracellular domain of human zB7R1 (residues 16 -140 of SEQ ID NO: 3) or an antigen binding fragment of the antibody.

13. The method of claim 2 wherein the test compound is an antibody that specifically binds to the extracellular domain of human CD155 (SEQ ID NO: 19) or an antigen binding fragment of the antibody.

14. The method of claim 4 wherein the test compound is an antibody that specifically binds to the extracellular domain of human CD155 (SEQ ID NO: 19) or an antigen binding fragment of the antibody.

* * * * *

SEQUENCE LISTING

```
<160> NUMBER OF SEQ ID NOS: 69

<210> SEQ ID NO 1
<211> LENGTH: 902
<212> TYPE: DNA
<213> ORGANISM: Homo sapiens
<220> FEATURE:
<221> NAME/KEY: CDS
<222> LOCATION: (11)..(745)
<220> FEATURE:
<221> NAME/KEY: misc_feature
<222> LOCATION: (289)..(289)
<223> OTHER INFORMATION: n = c or t
<220> FEATURE:
<221> NAME/KEY: misc_feature
<222> LOCATION: (359)..(359)
<223> OTHER INFORMATION: n = a or g

<400> SEQUENCE: 1
gggcagaagc atg cgc tgg tgt ctc ctc ctg atc tgg gcc cag ggg ctg         49
            Met Arg Trp Cys Leu Leu Leu Ile Trp Ala Gln Gly Leu
            1               5                   10 agg cag gct ccc ctc gcc tca gga atg atg aca ggc aca ata gaa aca         97
Arg Gln Ala Pro Leu Ala Ser Gly Met Met Thr Gly Thr Ile Glu Thr
    15                  20                  25
```

| | | | | | | | | | | | | | | | |
|---|---|---|---|---|---|---|---|---|---|---|---|---|---|---|---|
| acg | ggg | aac | att | tct | gca | gag | aaa | ggt | ggc | tct | atc | atc | tta | caa | tgt | 145 |
| Thr | Gly | Asn | Ile | Ser | Ala | Glu | Lys | Gly | Gly | Ser | Ile | Ile | Leu | Gln | Cys |
| 30 | | | | 35 | | | | | 40 | | | | | 45 | |

```
acg ggg aac att tct gca gag aaa ggt ggc tct atc atc tta caa tgt       145
Thr Gly Asn Ile Ser Ala Glu Lys Gly Gly Ser Ile Ile Leu Gln Cys
 30              35                  40                  45 cac ctc tcc tcc acc acg gca caa gtg acc cag gtc aac tgg gag cag       193
His Leu Ser Ser Thr Thr Ala Gln Val Thr Gln Val Asn Trp Glu Gln
                 50                  55                  60 cag gac cag ctt ctg gcc att tgt aat gct gac ttg ggg tgg cac atc       241
Gln Asp Gln Leu Leu Ala Ile Cys Asn Ala Asp Leu Gly Trp His Ile
             65                  70                  75 tcc cca tcc ttc aag gat cga gtg gcc cca ggt ccc ggc ctg ggc ctn       289
Ser Pro Ser Phe Lys Asp Arg Val Ala Pro Gly Pro Gly Leu Gly Xaa
         80                  85                  90 acc ctc cag tcg ctg acc gtg aac gat aca ggg gag tac ttc tgc atc       337
Thr Leu Gln Ser Leu Thr Val Asn Asp Thr Gly Glu Tyr Phe Cys Ile
     95                 100                 105 tat cac acc tac cct gat ggg ncg tac act ggg aga atc ttc ctg gag       385
Tyr His Thr Tyr Pro Asp Gly Xaa Tyr Thr Gly Arg Ile Phe Leu Glu
110                 115                 120                 125 gtc cta gaa agc tca gtg gct gag cac ggt gcc agg ttc cag att cca       433
Val Leu Glu Ser Ser Val Ala Glu His Gly Ala Arg Phe Gln Ile Pro
                130                 135                 140 ttg ctt gga gcc atg gcc gcg acg ctg gtg gtc atc tgc aca gca gtc       481
Leu Leu Gly Ala Met Ala Ala Thr Leu Val Val Ile Cys Thr Ala Val
            145                 150                 155 atc gtg gtg gtc gcg ttg act aga aag aag aaa gcc ctc aga atc cat       529
Ile Val Val Val Ala Leu Thr Arg Lys Lys Lys Ala Leu Arg Ile His
        160                 165                 170 tct gtg gaa ggt gac ctc agg aga aaa tca gct gga cag gag gaa tgg       577
Ser Val Glu Gly Asp Leu Arg Arg Lys Ser Ala Gly Gln Glu Glu Trp
    175                 180                 185 agc ccc agt gct ccc tca ccc cca gga agc tgt gtc cag gca gaa gct       625
Ser Pro Ser Ala Pro Ser Pro Pro Gly Ser Cys Val Gln Ala Glu Ala
190                 195                 200                 205 gca cct gct ggg ctc tgt gga gag cag cgg gga gag gac tgt gcc gag       673
Ala Pro Ala Gly Leu Cys Gly Glu Gln Arg Gly Glu Asp Cys Ala Glu
                210                 215                 220 ctg cat gac tac ttc aat gtc ctg agt tac aga agc ctg ggt aac tgc       721
Leu His Asp Tyr Phe Asn Val Leu Ser Tyr Arg Ser Leu Gly Asn Cys
            225                 230                 235 agc ttc ttc aca gag act ggt tag caaccagagg catcttctgg aagatacact     775
Ser Phe Phe Thr Glu Thr Gly
        240 tttgtctttg ctattataga tgaatatata agcagctgta ctctccatca gtgctgcgtg    835 tgtgtgtgtg tgtgtgtgta tgtgtgtgtg tgttcagttg agtgaataaa tgtcatcctc    895 ttctcca                                                              902
```

<210> SEQ ID NO 2
<211> LENGTH: 244
<212> TYPE: PRT
<213> ORGANISM: Homo sapiens
<220> FEATURE:
<221> NAME/KEY: misc_feature
<222> LOCATION: (93)..(93)
<223> OTHER INFORMATION: The 'Xaa' at location 93 stands for Leu.
<220> FEATURE:
<221> NAME/KEY: misc_feature
<222> LOCATION: (117)..(117)
<223> OTHER INFORMATION: The 'Xaa' at location 117 stands for Thr, Ala,
      Pro, or Ser.

<400> SEQUENCE: 2

```
Met Arg Trp Cys Leu Leu Ile Trp Ala Gln Gly Leu Arg Gln Ala
1               5                   10                  15
Pro Leu Ala Ser Gly Met Met Thr Gly Thr Ile Glu Thr Thr Gly Asn
            20                  25                  30
Ile Ser Ala Glu Lys Gly Gly Ser Ile Ile Leu Gln Cys His Leu Ser
        35                  40                  45
Ser Thr Thr Ala Gln Val Thr Gln Val Asn Trp Glu Gln Gln Asp Gln
    50                  55                  60
Leu Leu Ala Ile Cys Asn Ala Asp Leu Gly Trp His Ile Ser Pro Ser
65                  70                  75                  80
Phe Lys Asp Arg Val Ala Pro Gly Pro Gly Leu Gly Xaa Thr Leu Gln
                85                  90                  95
Ser Leu Thr Val Asn Asp Thr Gly Glu Tyr Phe Cys Ile Tyr His Thr
                100                 105                 110
Tyr Pro Asp Gly Xaa Tyr Thr Gly Arg Ile Phe Leu Glu Val Leu Glu
            115                 120                 125
Ser Ser Val Ala Glu His Gly Ala Arg Phe Gln Ile Pro Leu Leu Gly
        130                 135                 140
Ala Met Ala Ala Thr Leu Val Val Ile Cys Thr Ala Val Ile Val Val
145                 150                 155                 160
Val Ala Leu Thr Arg Lys Lys Ala Leu Arg Ile His Ser Val Glu
                165                 170                 175
Gly Asp Leu Arg Arg Lys Ser Ala Gly Gln Glu Glu Trp Ser Pro Ser
                180                 185                 190
Ala Pro Ser Pro Pro Gly Ser Cys Val Gln Ala Glu Ala Ala Pro Ala
            195                 200                 205
Gly Leu Cys Gly Glu Gln Arg Gly Glu Asp Cys Ala Glu Leu His Asp
        210                 215                 220
Tyr Phe Asn Val Leu Ser Tyr Arg Ser Leu Gly Asn Cys Ser Phe Phe
225                 230                 235                 240
Thr Glu Thr Gly

<210> SEQ ID NO 3
<211> LENGTH: 141
<212> TYPE: PRT
<213> ORGANISM: Homo sapiens

<400> SEQUENCE: 3

Met Arg Trp Cys Leu Leu Ile Trp Ala Gln Gly Leu Arg Gln Ala
1               5                   10                  15
Pro Leu Ala Ser Gly Met Met Thr Gly Thr Ile Glu Thr Thr Gly Asn
            20                  25                  30
Ile Ser Ala Glu Lys Gly Gly Ser Ile Ile Leu Gln Cys His Leu Ser
        35                  40                  45
Ser Thr Thr Ala Gln Val Thr Gln Val Asn Trp Glu Gln Gln Asp Gln
    50                  55                  60
Leu Leu Ala Ile Cys Asn Ala Asp Leu Gly Trp His Ile Ser Pro Ser
65                  70                  75                  80
Phe Lys Asp Arg Val Ala Pro Gly Pro Gly Leu Gly Leu Thr Leu Gln
                85                  90                  95
Ser Leu Thr Val Asn Asp Thr Gly Glu Tyr Phe Cys Ile Tyr His Thr
                100                 105                 110
Tyr Pro Asp Gly Thr Tyr Thr Gly Arg Ile Phe Leu Glu Val Leu Glu
            115                 120                 125
```

Ser Ser Val Ala Glu His Gly Ala Arg Phe Gln Ile Pro
    130                 135                 140

<210> SEQ ID NO 4
<211> LENGTH: 140
<212> TYPE: PRT
<213> ORGANISM: Homo sapiens

<400> SEQUENCE: 4

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile
    130                 135                 140

<210> SEQ ID NO 5
<211> LENGTH: 1711
<212> TYPE: DNA
<213> ORGANISM: Homo sapiens
<220> FEATURE:
<221> NAME/KEY: CDS
<222> LOCATION: (755)..(1690)

<400> SEQUENCE: 5
aaactatttg agggtagggg ctgtgattat ttactctcat atcctcagag cctggtgttg      60
aggttggtgc tttgtaggca cccagggact ttcaaatgaa tgaagggagg gagggaggaa     120
agaaggatgg tccatagta ggacctggtg atgggctggg agctccaggc aaatgtcaac      180
caatccctct cctgggtcag ctcccagggg ctcacccttc tttgcatttc cagctctcat     240
gaggtcattg tgcacaggaa agctctctcc tctaatctcc tctgatccta ctgcaccaga     300
gaaatcaagc cagaattcaa caaagtctca gtccagataa acaagacaaa agaaataaga     360
ttcgagtaga agatctccctt caagggaaag ttgctgtgtt tgtccaagac ctttgtccca    420
tccatgtatc atcccccaag taaacacttc ttgttcacct gttcattaga tttcaagtgc     480
agtccctggc ctgtaagtcc ctacaatgat aagtttctct tatcattgca cattcttcat     540
caggaggatg ccagaggagc tcagccaaca gttcctcatc agtagcagat tcttcagaat     600
cttgggcact acacagatgc ccttgagctc tttgaataaa ggctgatttt tagaaaaaac     660
attaagacag aacttaaaaa caatagattg actataatcc aaagacgagt gtacctctaa     720
ccacaatttt catttatttt taaatgtttc cttc atg gcc ttt ctt gtg gct cac    775
                                    Met Ala Phe Leu Val Ala His
                                    1               5 cct atg cag ttt gtg tat ttg ttg aca act tta tgt gtt ttt aat atg      823
Pro Met Gln Phe Val Tyr Leu Leu Thr Thr Leu Cys Val Phe Asn Met

|   |   |   |   |   |   |   |   |   |   |   |   |   |   |   |   |      |
|---|---|---|---|---|---|---|---|---|---|---|---|---|---|---|---|------|
|   |   |   | 10 |   |   |   | 15 |   |   |   | 20 |   |   |   |   |      |
| gtt | ttt | gcc | aaa | ctt | ggt | ttt | tcc | gag | acc | gtc | ttt | tct | cag | agg | ctc | 871 |
| Val | Phe | Ala | Lys | Leu | Gly | Phe | Ser | Glu | Thr | Val | Phe | Ser | Gln | Arg | Leu |  |
|  | 25 |  |  |  |  | 30 |  |  |  |  | 35 |  |  |  |  |  |
| agt | ttt | acc | gtc | cta | tct | gca | gtc | ggc | tac | ttt | cag | tgg | cag | aag | agg | 919 |
| Ser | Phe | Thr | Val | Leu | Ser | Ala | Val | Gly | Tyr | Phe | Gln | Trp | Gln | Lys | Arg |  |
| 40 |  |  |  |  | 45 |  |  |  |  | 50 |  |  |  |  | 55 |  |
| cca | cat | ctg | ctt | cct | gta | ggc | cct | ctg | ggc | aga | agc | atg | cgc | tgg | tgt | 967 |
| Pro | His | Leu | Leu | Pro | Val | Gly | Pro | Leu | Gly | Arg | Ser | Met | Arg | Trp | Cys |  |
|  |  |  |  | 60 |  |  |  |  | 65 |  |  |  |  | 70 |  |  |
| ctc | ctc | ctg | atc | tgg | gcc | cag | ggg | ctg | agg | cag | gct | ccc | ctc | gcc | tca | 1015 |
| Leu | Leu | Leu | Ile | Trp | Ala | Gln | Gly | Leu | Arg | Gln | Ala | Pro | Leu | Ala | Ser |  |
|  |  |  | 75 |  |  |  |  | 80 |  |  |  |  | 85 |  |  |  |
| gga | atg | atg | aca | ggc | aca | ata | gaa | aca | acg | ggg | aac | att | tct | gca | gag | 1063 |
| Gly | Met | Met | Thr | Gly | Thr | Ile | Glu | Thr | Thr | Gly | Asn | Ile | Ser | Ala | Glu |  |
|  |  | 90 |  |  |  |  | 95 |  |  |  |  | 100 |  |  |  |  |
| aaa | ggt | ggc | tct | atc | atc | tta | caa | tgt | cac | ctc | tcc | tcc | acc | acg | gca | 1111 |
| Lys | Gly | Gly | Ser | Ile | Ile | Leu | Gln | Cys | His | Leu | Ser | Ser | Thr | Thr | Ala |  |
|  | 105 |  |  |  |  | 110 |  |  |  |  | 115 |  |  |  |  |  |
| caa | gtg | acc | cag | gtc | aac | tgg | gag | cag | cag | gac | cag | ctt | ctg | gcc | att | 1159 |
| Gln | Val | Thr | Gln | Val | Asn | Trp | Glu | Gln | Gln | Asp | Gln | Leu | Leu | Ala | Ile |  |
| 120 |  |  |  |  | 125 |  |  |  |  | 130 |  |  |  |  | 135 |  |
| tgt | aat | gct | gac | ttg | ggg | tgg | cac | atc | tcc | cca | tcc | ttc | aag | gat | cga | 1207 |
| Cys | Asn | Ala | Asp | Leu | Gly | Trp | His | Ile | Ser | Pro | Ser | Phe | Lys | Asp | Arg |  |
|  |  |  |  | 140 |  |  |  |  | 145 |  |  |  |  | 150 |  |  |
| gtg | gcc | cca | ggt | ccc | ggc | ctg | ggc | ctc | acc | ctc | cag | tcg | ctg | acc | gtg | 1255 |
| Val | Ala | Pro | Gly | Pro | Gly | Leu | Gly | Leu | Thr | Leu | Gln | Ser | Leu | Thr | Val |  |
|  |  |  | 155 |  |  |  |  | 160 |  |  |  |  | 165 |  |  |  |
| aac | gat | aca | ggg | gag | tac | ttc | tgc | atc | tat | cac | acc | tac | cct | gat | ggg | 1303 |
| Asn | Asp | Thr | Gly | Glu | Tyr | Phe | Cys | Ile | Tyr | His | Thr | Tyr | Pro | Asp | Gly |  |
|  |  | 170 |  |  |  |  | 175 |  |  |  |  | 180 |  |  |  |  |
| acg | tac | act | ggg | aga | atc | ttc | ctg | gag | gtc | cta | gaa | agc | tca | gtg | gct | 1351 |
| Thr | Tyr | Thr | Gly | Arg | Ile | Phe | Leu | Glu | Val | Leu | Glu | Ser | Ser | Val | Ala |  |
|  | 185 |  |  |  |  | 190 |  |  |  |  | 195 |  |  |  |  |  |
| gag | cac | ggt | gcc | agg | ttc | cag | att | cca | ttg | ctt | gga | gcc | atg | gcc | gcg | 1399 |
| Glu | His | Gly | Ala | Arg | Phe | Gln | Ile | Pro | Leu | Leu | Gly | Ala | Met | Ala | Ala |  |
| 200 |  |  |  |  | 205 |  |  |  |  | 210 |  |  |  |  | 215 |  |
| acg | ctg | gtg | gtc | atc | tgc | aca | gca | gtc | atc | gtg | gtg | gtc | gcg | ttg | act | 1447 |
| Thr | Leu | Val | Val | Ile | Cys | Thr | Ala | Val | Ile | Val | Val | Val | Ala | Leu | Thr |  |
|  |  |  |  | 220 |  |  |  |  | 225 |  |  |  |  | 230 |  |  |
| aga | aag | aag | aaa | gcc | ctc | aga | atc | cat | tct | gtg | gaa | ggt | gac | ctc | agg | 1495 |
| Arg | Lys | Lys | Lys | Ala | Leu | Arg | Ile | His | Ser | Val | Glu | Gly | Asp | Leu | Arg |  |
|  |  |  | 235 |  |  |  |  | 240 |  |  |  |  | 245 |  |  |  |
| aga | aaa | tca | gct | gga | cag | gag | gaa | tgg | agc | ccc | agt | gct | ccc | tca | ccc | 1543 |
| Arg | Lys | Ser | Ala | Gly | Gln | Glu | Glu | Trp | Ser | Pro | Ser | Ala | Pro | Ser | Pro |  |
|  |  | 250 |  |  |  |  | 255 |  |  |  |  | 260 |  |  |  |  |
| cca | gga | agc | tgt | gtc | cag | gca | gaa | gct | gca | cct | gct | ggg | ctc | tgt | gga | 1591 |
| Pro | Gly | Ser | Cys | Val | Gln | Ala | Glu | Ala | Ala | Pro | Ala | Gly | Leu | Cys | Gly |  |
|  | 265 |  |  |  |  | 270 |  |  |  |  | 275 |  |  |  |  |  |
| gag | cag | cgg | gga | gag | gac | tgt | gcc | gag | ctg | cat | gac | tac | ttc | aat | gtc | 1639 |
| Glu | Gln | Arg | Gly | Glu | Asp | Cys | Ala | Glu | Leu | His | Asp | Tyr | Phe | Asn | Val |  |
| 280 |  |  |  |  | 285 |  |  |  |  | 290 |  |  |  |  | 295 |  |
| ctg | agt | tac | aga | agc | ctg | ggt | aac | tgc | agc | ttc | ttc | aca | gag | act | ggt | 1687 |
| Leu | Ser | Tyr | Arg | Ser | Leu | Gly | Asn | Cys | Ser | Phe | Phe | Thr | Glu | Thr | Gly |  |
|  |  |  |  | 300 |  |  |  |  | 305 |  |  |  |  | 310 |  |  |
| tag | caaccagagg | catcttctgg | a |   |   |   |   |   |   |   |   |   |   |   |   | 1711 |

<210> SEQ ID NO 6
<211> LENGTH: 311

```
<212> TYPE: PRT
<213> ORGANISM: Homo sapiens

<400> SEQUENCE: 6

Met Ala Phe Leu Val Ala His Pro Met Gln Phe Val Tyr Leu Leu Thr
1               5                   10                  15

Thr Leu Cys Val Phe Asn Met Val Phe Ala Lys Leu Gly Phe Ser Glu
            20                  25                  30

Thr Val Phe Ser Gln Arg Leu Ser Phe Thr Val Leu Ser Ala Val Gly
        35                  40                  45

Tyr Phe Gln Trp Gln Lys Arg Pro His Leu Leu Pro Val Gly Pro Leu
    50                  55                  60

Gly Arg Ser Met Arg Trp Cys Leu Leu Leu Ile Trp Ala Gln Gly Leu
65                  70                  75                  80

Arg Gln Ala Pro Leu Ala Ser Gly Met Met Thr Gly Thr Ile Glu Thr
                85                  90                  95

Thr Gly Asn Ile Ser Ala Glu Lys Gly Gly Ser Ile Ile Leu Gln Cys
            100                 105                 110

His Leu Ser Ser Thr Thr Ala Gln Val Thr Gln Val Asn Trp Glu Gln
        115                 120                 125

Gln Asp Gln Leu Leu Ala Ile Cys Asn Ala Asp Leu Gly Trp His Ile
    130                 135                 140

Ser Pro Ser Phe Lys Asp Arg Val Ala Pro Gly Pro Gly Leu Gly Leu
145                 150                 155                 160

Thr Leu Gln Ser Leu Thr Val Asn Asp Thr Gly Glu Tyr Phe Cys Ile
                165                 170                 175

Tyr His Thr Tyr Pro Asp Gly Thr Tyr Thr Gly Arg Ile Phe Leu Glu
            180                 185                 190

Val Leu Glu Ser Ser Val Ala Glu His Gly Ala Arg Phe Gln Ile Pro
        195                 200                 205

Leu Leu Gly Ala Met Ala Ala Thr Leu Val Val Ile Cys Thr Ala Val
    210                 215                 220

Ile Val Val Val Ala Leu Thr Arg Lys Lys Lys Ala Leu Arg Ile His
225                 230                 235                 240

Ser Val Glu Gly Asp Leu Arg Arg Lys Ser Ala Gly Gln Glu Glu Trp
                245                 250                 255

Ser Pro Ser Ala Pro Ser Pro Pro Gly Ser Cys Val Gln Ala Glu Ala
            260                 265                 270

Ala Pro Ala Gly Leu Cys Gly Glu Gln Arg Gly Glu Asp Cys Ala Glu
        275                 280                 285

Leu His Asp Tyr Phe Asn Val Leu Ser Tyr Arg Ser Leu Gly Asn Cys
    290                 295                 300

Ser Phe Phe Thr Glu Thr Gly
305                 310

<210> SEQ ID NO 7
<211> LENGTH: 208
<212> TYPE: PRT
<213> ORGANISM: Homo sapiens

<400> SEQUENCE: 7

Met Ala Phe Leu Val Ala His Pro Met Gln Phe Val Tyr Leu Leu Thr
1               5                   10                  15

Thr Leu Cys Val Phe Asn Met Val Phe Ala Lys Leu Gly Phe Ser Glu
            20                  25                  30
```

-continued

```
Thr Val Phe Ser Gln Arg Leu Ser Phe Thr Val Leu Ser Ala Val Gly
         35                  40                  45

Tyr Phe Gln Trp Gln Lys Arg Pro His Leu Leu Pro Val Gly Pro Leu
 50                  55                  60

Gly Arg Ser Met Arg Trp Cys Leu Leu Leu Ile Trp Ala Gln Gly Leu
 65                  70                  75                  80

Arg Gln Ala Pro Leu Ala Ser Gly Met Met Thr Gly Thr Ile Glu Thr
                 85                  90                  95

Thr Gly Asn Ile Ser Ala Glu Lys Gly Gly Ser Ile Ile Leu Gln Cys
            100                 105                 110

His Leu Ser Ser Thr Thr Ala Gln Val Thr Gln Val Asn Trp Glu Gln
        115                 120                 125

Gln Asp Gln Leu Leu Ala Ile Cys Asn Ala Asp Leu Gly Trp His Ile
    130                 135                 140

Ser Pro Ser Phe Lys Asp Arg Val Ala Pro Gly Pro Gly Leu Gly Leu
145                 150                 155                 160

Thr Leu Gln Ser Leu Thr Val Asn Asp Thr Gly Glu Tyr Phe Cys Ile
                165                 170                 175

Tyr His Thr Tyr Pro Asp Gly Thr Tyr Thr Gly Arg Ile Phe Leu Glu
            180                 185                 190

Val Leu Glu Ser Ser Val Ala Glu His Gly Ala Arg Phe Gln Ile Pro
        195                 200                 205
```

<210> SEQ ID NO 8
<211> LENGTH: 726
<212> TYPE: DNA
<213> ORGANISM: Mus musculus
<220> FEATURE:
<221> NAME/KEY: CDS
<222> LOCATION: (1)..(726)

<400> SEQUENCE: 8

```
atg cat ggc tgg ctg ctc ctg gtc tgg gtc cag ggg ctg ata cag gct      48
Met His Gly Trp Leu Leu Leu Val Trp Val Gln Gly Leu Ile Gln Ala
 1               5                  10                  15 gcc ttc ctc gct aca gga gcc aca gca ggc acg ata gat aca aag agg      96
Ala Phe Leu Ala Thr Gly Ala Thr Ala Gly Thr Ile Asp Thr Lys Arg
             20                  25                  30 aac atc tct gca gag gaa ggt ggc tct gtc atc tta cag tgt cac ttc     144
Asn Ile Ser Ala Glu Glu Gly Gly Ser Val Ile Leu Gln Cys His Phe
         35                  40                  45 tcc tct gac aca gct gaa gtg acc caa gtc gac tgg aag cag cag gac     192
Ser Ser Asp Thr Ala Glu Val Thr Gln Val Asp Trp Lys Gln Gln Asp
 50                  55                  60 cag ctt ctg gcc att tat agt gtt gac ctg ggg tgg cat gtc gct tca     240
Gln Leu Leu Ala Ile Tyr Ser Val Asp Leu Gly Trp His Val Ala Ser
 65                  70                  75                  80 gtc ttc agt gat cgg gtg gtc cca ggc ccc agc cta ggc ctc acc ttc     288
Val Phe Ser Asp Arg Val Val Pro Gly Pro Ser Leu Gly Leu Thr Phe
                 85                  90                  95 cag tct ctg aca atg aat gac acg gga gag tac ttc tgt acc tat cat     336
Gln Ser Leu Thr Met Asn Asp Thr Gly Glu Tyr Phe Cys Thr Tyr His
            100                 105                 110 acg tat cct ggt ggg att tac aag ggg aga ata ttc ctg aag gtc caa     384
Thr Tyr Pro Gly Gly Ile Tyr Lys Gly Arg Ile Phe Leu Lys Val Gln
        115                 120                 125 gaa agc tca gtg gct cag ttc cag act gcc ccg ctt gga gga acc atg     432
Glu Ser Ser Val Ala Gln Phe Gln Thr Ala Pro Leu Gly Gly Thr Met
    130                 135                 140
```

```
gct gct gtg ctg gga ctc att tgc tta atg gtc aca gga gtg act gta    480
Ala Ala Val Leu Gly Leu Ile Cys Leu Met Val Thr Gly Val Thr Val
145                 150                 155                 160 ctg gct aga aag aag tct att aga atg cat tct ata gaa agt ggc ctt    528
Leu Ala Arg Lys Lys Ser Ile Arg Met His Ser Ile Glu Ser Gly Leu
                165                 170                 175 ggg aga aca gaa gcg gag cca cag gaa tgg aac ctg agg agt ctc tca    576
Gly Arg Thr Glu Ala Glu Pro Gln Glu Trp Asn Leu Arg Ser Leu Ser
            180                 185                 190 tcc cct gga agc cct gtc cag aca caa act gcc cct gct ggt ccc tgt    624
Ser Pro Gly Ser Pro Val Gln Thr Gln Thr Ala Pro Ala Gly Pro Cys
        195                 200                 205 gga gag cag gca gaa gat gac tat gct gac cca cag gaa tac ttt aat    672
Gly Glu Gln Ala Glu Asp Asp Tyr Ala Asp Pro Gln Glu Tyr Phe Asn
    210                 215                 220 gtc ctg agc tac aga agc cta gag agc ttc att gct gta tcg aag act    720
Val Leu Ser Tyr Arg Ser Leu Glu Ser Phe Ile Ala Val Ser Lys Thr
225                 230                 235                 240 ggc taa                                                            726
Gly

<210> SEQ ID NO 9
<211> LENGTH: 241
<212> TYPE: PRT
<213> ORGANISM: Mus musculus

<400> SEQUENCE: 9

Met His Gly Trp Leu Leu Val Trp Val Gln Gly Leu Ile Gln Ala
1               5                   10                  15

Ala Phe Leu Ala Thr Gly Ala Thr Ala Gly Thr Ile Asp Thr Lys Arg
                20                  25                  30

Asn Ile Ser Ala Glu Glu Gly Gly Ser Val Ile Leu Gln Cys His Phe
            35                  40                  45

Ser Ser Asp Thr Ala Glu Val Thr Gln Val Asp Trp Lys Gln Gln Asp
        50                  55                  60

Gln Leu Leu Ala Ile Tyr Ser Val Asp Leu Gly Trp His Val Ala Ser
65                  70                  75                  80

Val Phe Ser Asp Arg Val Val Pro Gly Pro Ser Leu Gly Leu Thr Phe
                85                  90                  95

Gln Ser Leu Thr Met Asn Asp Thr Gly Glu Tyr Phe Cys Thr Tyr His
                100                 105                 110

Thr Tyr Pro Gly Gly Ile Tyr Lys Gly Arg Ile Phe Leu Lys Val Gln
            115                 120                 125

Glu Ser Ser Val Ala Gln Phe Gln Thr Ala Pro Leu Gly Gly Thr Met
130                 135                 140

Ala Ala Val Leu Gly Leu Ile Cys Leu Met Val Thr Gly Val Thr Val
145                 150                 155                 160

Leu Ala Arg Lys Lys Ser Ile Arg Met His Ser Ile Glu Ser Gly Leu
                165                 170                 175

Gly Arg Thr Glu Ala Glu Pro Gln Glu Trp Asn Leu Arg Ser Leu Ser
            180                 185                 190

Ser Pro Gly Ser Pro Val Gln Thr Gln Thr Ala Pro Ala Gly Pro Cys
        195                 200                 205

Gly Glu Gln Ala Glu Asp Asp Tyr Ala Asp Pro Gln Glu Tyr Phe Asn
    210                 215                 220

Val Leu Ser Tyr Arg Ser Leu Glu Ser Phe Ile Ala Val Ser Lys Thr
```

```
                      225                 230                 235                 240
Gly

<210> SEQ ID NO 10
<211> LENGTH: 139
<212> TYPE: PRT
<213> ORGANISM: Mus musculus

<400> SEQUENCE: 10

Met His Gly Trp Leu Leu Val Trp Val Gln Gly Leu Ile Gln Ala
1               5                   10                  15

Ala Phe Leu Ala Thr Gly Ala Thr Ala Gly Thr Ile Asp Thr Lys Arg
                20                  25                  30

Asn Ile Ser Ala Glu Glu Gly Gly Ser Val Ile Leu Gln Cys His Phe
            35                  40                  45

Ser Ser Asp Thr Ala Glu Val Thr Gln Val Asp Trp Lys Gln Gln Asp
        50                  55                  60

Gln Leu Leu Ala Ile Tyr Ser Val Asp Leu Gly Trp His Val Ala Ser
65                  70                  75                  80

Val Phe Ser Asp Arg Val Val Pro Gly Pro Ser Leu Gly Leu Thr Phe
                85                  90                  95

Gln Ser Leu Thr Met Asn Asp Thr Gly Glu Tyr Phe Cys Thr Tyr His
            100                 105                 110

Thr Tyr Pro Gly Gly Ile Tyr Lys Gly Arg Ile Phe Leu Lys Val Gln
        115                 120                 125

Glu Ser Ser Val Ala Gln Phe Gln Thr Ala Pro
    130                 135

<210> SEQ ID NO 11
<211> LENGTH: 140
<212> TYPE: PRT
<213> ORGANISM: Homo sapiens

<400> SEQUENCE: 11

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
                20                  25                  30

Ile Ser Ala Glu Lys Gly Gly Ser Ile Ile Leu Gln Cys His Leu Ser
            35                  40                  45

Ser Thr Thr Ala Gln Val Thr Gln Val Asn Trp Glu Gln Gln Asp Gln
        50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile
    130                 135                 140

<210> SEQ ID NO 12
<211> LENGTH: 138
<212> TYPE: PRT
<213> ORGANISM: Mus musculus
```

<400> SEQUENCE: 12

Met His Gly Trp Leu Leu Val Trp Val Gln Gly Leu Ile Gln Ala
1               5                   10                  15

Ala Phe Leu Ala Thr Gly Ala Thr Gly Thr Ile Asp Thr Lys Arg
                20                  25                  30

Asn Ile Ser Ala Glu Glu Gly Ser Val Ile Leu Gln Cys His Phe
            35                  40                  45

Ser Ser Asp Thr Ala Glu Val Thr Gln Val Asp Trp Lys Gln Asp
        50                  55                  60

Gln Leu Leu Ala Ile Tyr Ser Val Asp Leu Gly Trp His Val Ala Ser
65                  70                  75                  80

Val Phe Ser Asp Arg Val Val Pro Gly Pro Ser Leu Gly Leu Thr Phe
                85                  90                  95

Gln Ser Leu Thr Met Asn Asp Thr Gly Glu Tyr Phe Cys Thr Tyr His
                100                 105                 110

Thr Tyr Pro Gly Gly Ile Tyr Lys Gly Arg Ile Phe Leu Lys Val Gln
            115                 120                 125

Glu Ser Ser Val Ala Gln Phe Gln Thr Ala
    130                 135

<210> SEQ ID NO 13
<211> LENGTH: 147
<212> TYPE: DNA
<213> ORGANISM: Artificial Sequence
<220> FEATURE:
<223> OTHER INFORMATION: VASP-His6 Tetramerizing Domain

<400> SEQUENCE: 13
ggctccggtg gctccgacct acagagggtg aaacaggagc ttctggaaga ggtgaagaag       60
gaattgcaga aagtgaaaga ggaaatcatt gaagccttcg tccaggagct gagggttcc      120 ggtggccatc accatcacca tcactga                                         147

<210> SEQ ID NO 14
<211> LENGTH: 48
<212> TYPE: PRT
<213> ORGANISM: Artificial Sequence
<220> FEATURE:
<223> OTHER INFORMATION: VASP-His6 tetramerizing domain

<400> SEQUENCE: 14

Gly Ser Gly Gly Ser Asp Leu Gln Arg Val Lys Gln Glu Leu Leu Glu
1               5                   10                  15

Glu Val Lys Lys Glu Leu Gln Lys Val Lys Glu Glu Ile Ile Glu Ala
                20                  25                  30

Phe Val Gln Glu Leu Arg Gly Ser Gly Gly His His His His His His
            35                  40                  45

<210> SEQ ID NO 15
<211> LENGTH: 4
<212> TYPE: PRT
<213> ORGANISM: Artificial Sequence
<220> FEATURE:
<223> OTHER INFORMATION: Linker

<400> SEQUENCE: 15

Gly Ser Gly Gly
1

-continued

```
<210> SEQ ID NO 16
<211> LENGTH: 6
<212> TYPE: PRT
<213> ORGANISM: Artificial Sequence
<220> FEATURE:
<223> OTHER INFORMATION: Linker

<400> SEQUENCE: 16

His His His His His His
1               5

<210> SEQ ID NO 17
<211> LENGTH: 3200
<212> TYPE: DNA
<213> ORGANISM: Artificial Sequence
<220> FEATURE:
<223> OTHER INFORMATION: Human CD155
<220> FEATURE:
<221> NAME/KEY: CDS
<222> LOCATION: (184)..(1425)

<400> SEQUENCE: 17
cttgaagaag tgggtattcc ccttcccacc ccaggcactg gaggagcggc ccccggggga      60
ttccaggacc tgagctccgg gagctggact cgcagcgacc gcggcagagc gagctggcgc     120
cgggaagcga ggagacgccc gcgggaggcc cagctgctcg agcaactgg catggcccga     180 gcc atg gcc gcc gcg tgg ccg ctg ctg ctg gtg gcg cta ctg gtg ctg      228
    Met Ala Ala Ala Trp Pro Leu Leu Leu Val Ala Leu Leu Val Leu
    1               5                   10                  15 tcc tgg cca ccc cca gga acc ggg gac gtc gtc gtg cag gcc ccc acc      276
Ser Trp Pro Pro Pro Gly Thr Gly Asp Val Val Val Gln Ala Pro Thr
            20                  25                  30 cag gtg ccc ggc ttc ttg ggc gac tcc gtg acg ctg ccc tgc tac cta      324
Gln Val Pro Gly Phe Leu Gly Asp Ser Val Thr Leu Pro Cys Tyr Leu
        35                  40                  45 cag gtg ccc aac atg gag gtg acg cat gtg tca cag ctg act tgg gcg      372
Gln Val Pro Asn Met Glu Val Thr His Val Ser Gln Leu Thr Trp Ala
    50                  55                  60 cgg cat ggt gaa tct ggc agc atg gcc gtc ttc cac caa acg cag ggc      420
Arg His Gly Glu Ser Gly Ser Met Ala Val Phe His Gln Thr Gln Gly
65                  70                  75 ccc agc tat tcg gag tcc aaa cgg ctg gaa ttc gtg gca gcc aga ctg      468
Pro Ser Tyr Ser Glu Ser Lys Arg Leu Glu Phe Val Ala Ala Arg Leu
80                  85                  90                  95 ggc gcg gag ctg cgg aat gcc tcg ctg agg atg ttc ggg ttg cgc gta      516
Gly Ala Glu Leu Arg Asn Ala Ser Leu Arg Met Phe Gly Leu Arg Val
                100                 105                 110 gag gat gaa ggc aac tac acc tgc ctg ttc gtc acg ttc ccg cag ggc      564
Glu Asp Glu Gly Asn Tyr Thr Cys Leu Phe Val Thr Phe Pro Gln Gly
            115                 120                 125 agc agg agc gtg gat atc tgg ctc cga gtg ctt gcc aag ccc cag aac      612
Ser Arg Ser Val Asp Ile Trp Leu Arg Val Leu Ala Lys Pro Gln Asn
        130                 135                 140 aca gct gag gtt cag aag gtc cag ctc act gga gag cca gtg ccc atg      660
Thr Ala Glu Val Gln Lys Val Gln Leu Thr Gly Glu Pro Val Pro Met
    145                 150                 155 gcc cgc tgc gtc tcc aca ggg ggt cgc ccg cca gcc caa atc acc tgg      708
Ala Arg Cys Val Ser Thr Gly Gly Arg Pro Pro Ala Gln Ile Thr Trp
160                 165                 170                 175 cac tca gac ctg ggc ggg atg ccc aat acg agc cag gtg cca ggg ttc      756
His Ser Asp Leu Gly Gly Met Pro Asn Thr Ser Gln Val Pro Gly Phe
                180                 185                 190
```

```
ctg tct ggc aca gtc act gtc acc agc ctc tgg ata ttg gtg ccc tca    804
Leu Ser Gly Thr Val Thr Val Thr Ser Leu Trp Ile Leu Val Pro Ser
            195                 200                 205 agc cag gtg gac ggc aag aat gtg acc tgc aag gtg gag cac gag agc    852
Ser Gln Val Asp Gly Lys Asn Val Thr Cys Lys Val Glu His Glu Ser
            210                 215                 220 ttt gag aag cct cag ctg ctg act gtg aac ctc acc gtg tac tac ccc    900
Phe Glu Lys Pro Gln Leu Leu Thr Val Asn Leu Thr Val Tyr Tyr Pro
225                 230                 235 cca gag gta tcc atc tct ggc tat gat aac aac tgg tac ctt ggc cag    948
Pro Glu Val Ser Ile Ser Gly Tyr Asp Asn Asn Trp Tyr Leu Gly Gln
240                 245                 250                 255 aat gag gcc acc ctg acc tgc gat gct cgc agc aac cca gag ccc aca    996
Asn Glu Ala Thr Leu Thr Cys Asp Ala Arg Ser Asn Pro Glu Pro Thr
            260                 265                 270 ggc tat aat tgg agc acg acc atg ggt ccc ctg cca ccc ttt gct gtg   1044
Gly Tyr Asn Trp Ser Thr Thr Met Gly Pro Leu Pro Pro Phe Ala Val
            275                 280                 285 gcc cag ggc gcc cag ctc ctg atc cgt cct gtg gac aaa cca atc aac   1092
Ala Gln Gly Ala Gln Leu Leu Ile Arg Pro Val Asp Lys Pro Ile Asn
            290                 295                 300 aca act tta atc tgc aac gtc acc aat gcc cta gga gct cgc cag gca   1140
Thr Thr Leu Ile Cys Asn Val Thr Asn Ala Leu Gly Ala Arg Gln Ala
305                 310                 315 gaa ctg acc gtc cag gtc aaa gag gga cct ccc agt gag cac tca ggc   1188
Glu Leu Thr Val Gln Val Lys Glu Gly Pro Pro Ser Glu His Ser Gly
320                 325                 330                 335 atg tcc cgt aac gcc atc atc ttc ctg gtt ctg gga atc ctg gtt ttt   1236
Met Ser Arg Asn Ala Ile Ile Phe Leu Val Leu Gly Ile Leu Val Phe
            340                 345                 350 ctg atc ctg ctg ggg atc ggg att tat ttc tat tgg tcc aaa tgt tcc   1284
Leu Ile Leu Leu Gly Ile Gly Ile Tyr Phe Tyr Trp Ser Lys Cys Ser
            355                 360                 365 cgt gag gtc ctt tgg cac tgt cat ctg tgt ccc tcg agt aca gag cat   1332
Arg Glu Val Leu Trp His Cys His Leu Cys Pro Ser Ser Thr Glu His
            370                 375                 380 gcc agc gcc tca gct aat ggg cat gtc tcc tat tca gct gtg agc aga   1380
Ala Ser Ala Ser Ala Asn Gly His Val Ser Tyr Ser Ala Val Ser Arg
385                 390                 395 gag aac agc tct tcc cag gat cca cag aca gag ggc aca agg tga       1425
Glu Asn Ser Ser Ser Gln Asp Pro Gln Thr Glu Gly Thr Arg
400                 405                 410 cagcgtcggg actgagaggg gagagagact ggagctggca aggacgtggg cctccagagt   1485
tggacccgac cccaatggat gaagaccccc tccaaagaga ccagcctccc tccctgtgcc   1545
agacctcaaa acgacggggg caggtgcaag ttcataggtc tccaagacca ccctcctttc   1605
atttgctaga aggactcact agactcagga aagctgttag gctcacagtt acagtttatt   1665
acagtaaaag gacagagatt aagatcagca aaggggaggag gtgcacagca cacgttccac   1725
gacagatgag gcgacggctt ccatctgccc tctcccagtg gagccatata ggcagcacct   1785
gattctcaca gcaacatgtg acaacatgca agaagtactg ccaatactgc caaccagagc   1845
agctcactcg agatctttgt gtccagagtt ttttgtttgt cttgagacag ggtcggctc    1905 tgttggcaga ctagagtaca gtggtgagat cacagttcat tgcagccttg acttctcaac   1965
gccaagtcat cctcccacct cagcctcctg agtagctatg actacaggta tgtgccacca   2025
cgtctggcta atctttttat tatttgtaaa gtcgaggttt ccctgtgttg cccaggctgg   2085
tcttgaactc ttggctccaa gtgatacttc tgccttggcc tcccaaagtg ctgaattaag   2145
```

-continued

```
cagctcacca tccacacggc tgacctcata catcaagcca ataccgtgtg gcccaagacc    2205
cccaccataa atcacatcat tagcatgaac cacccagagt ggcccaagac tcccagatca    2265
gctaccaggc aggatattcc aagggcttag agatgaatgc ccaggagctg aggataaagg    2325
gcccgatctt tctttgggca aggttaagcc tttactgcat agcagaccac acagaagggt    2385
gtgggccacc agagaatttt ggtaaaaatt tggcctctgg ccttgagctt ctaaatctct    2445
gtatccgtca gatctctgtg gttacaagaa acagccactg accctggtca ccagaggctg    2505
caattcaggc cgcaagcagc tgcctagggg gtgtccaagg agcagagaaa actactagat    2565
gtgaacttga agaaggttgt cagctgcagc cactttctgc cagcatctgc agccactttc    2625
tgccagcatc tgcagccagc aagctggac tggcaggaaa taacccacaa agaagcaaa     2685 tgcaatttcc aacacaaggg ggaagggatg caggggagg cagcgctgca gttgctcagg    2745
acacgctcct ataggaccaa gatggatgcg acccaagacc caggaggccc agctgctcag    2805
tgcaactgac aagttaaaaa ggtctatgat cttgagggca gacagcagaa ttcctcttat    2865
aaagaaaact gtttgggaaa atacgttgag ggagagaaga ccttgggcca agatgctaaa    2925
tgggaatgca aagcttgagc tgctctgcaa gagaaaataa gcaggacaga ggatttgctc    2985
tggacagaga tggaagagcc gggaacagag aagtgtgggg aagagatagg aaccagcagg    3045
atggcagggg caaagggctc aagggtgagg aggccagtgg gacccacag agttggggag     3105 ataaaggaac attggttgct ttggtggcac gtaagctcct tgtctgtctc cagcacccag    3165
aatctcatta agcttatttt attgtacctc caaaa                              3200
```

<210> SEQ ID NO 18
<211> LENGTH: 413
<212> TYPE: PRT
<213> ORGANISM: Artificial Sequence
<220> FEATURE:
<223> OTHER INFORMATION: Synthetic Construct

<400> SEQUENCE: 18

```
Met Ala Ala Ala Trp Pro Leu Leu Leu Val Ala Leu Leu Val Leu Ser
1               5                   10                  15

Trp Pro Pro Pro Gly Thr Gly Asp Val Val Gln Ala Pro Thr Gln
            20                  25                  30

Val Pro Gly Phe Leu Gly Asp Ser Val Thr Leu Pro Cys Tyr Leu Gln
        35                  40                  45

Val Pro Asn Met Glu Val Thr His Val Ser Gln Leu Thr Trp Ala Arg
    50                  55                  60

His Gly Glu Ser Gly Ser Met Ala Val Phe His Gln Thr Gln Gly Pro
65                  70                  75                  80

Ser Tyr Ser Glu Ser Lys Arg Leu Glu Phe Val Ala Ala Arg Leu Gly
                85                  90                  95

Ala Glu Leu Arg Asn Ala Ser Leu Arg Met Phe Gly Leu Arg Val Glu
            100                 105                 110

Asp Glu Gly Asn Tyr Thr Cys Leu Phe Val Thr Phe Pro Gln Gly Ser
        115                 120                 125

Arg Ser Val Asp Ile Trp Leu Arg Val Leu Ala Lys Pro Gln Asn Thr
    130                 135                 140

Ala Glu Val Gln Lys Val Gln Leu Thr Gly Glu Pro Val Pro Met Ala
145                 150                 155                 160

Arg Cys Val Ser Thr Gly Gly Arg Pro Pro Ala Gln Ile Thr Trp His
                165                 170                 175
```

-continued

Ser Asp Leu Gly Gly Met Pro Asn Thr Ser Gln Val Pro Gly Phe Leu
            180                 185                 190

Ser Gly Thr Val Thr Val Thr Ser Leu Trp Ile Leu Val Pro Ser Ser
        195                 200                 205

Gln Val Asp Gly Lys Asn Val Thr Cys Lys Val Glu His Glu Ser Phe
    210                 215                 220

Glu Lys Pro Gln Leu Leu Thr Val Asn Leu Thr Val Tyr Tyr Pro Pro
225                 230                 235                 240

Glu Val Ser Ile Ser Gly Tyr Asp Asn Asn Trp Tyr Leu Gly Gln Asn
                245                 250                 255

Glu Ala Thr Leu Thr Cys Asp Ala Arg Ser Asn Pro Glu Pro Thr Gly
            260                 265                 270

Tyr Asn Trp Ser Thr Thr Met Gly Pro Leu Pro Pro Phe Ala Val Ala
        275                 280                 285

Gln Gly Ala Gln Leu Leu Ile Arg Pro Val Asp Lys Pro Ile Asn Thr
    290                 295                 300

Thr Leu Ile Cys Asn Val Thr Asn Ala Leu Gly Ala Arg Gln Ala Glu
305                 310                 315                 320

Leu Thr Val Gln Val Lys Glu Gly Pro Pro Ser Glu His Ser Gly Met
                325                 330                 335

Ser Arg Asn Ala Ile Ile Phe Leu Val Leu Gly Ile Leu Val Phe Leu
            340                 345                 350

Ile Leu Leu Gly Ile Gly Ile Tyr Phe Tyr Trp Ser Lys Cys Ser Arg
        355                 360                 365

Glu Val Leu Trp His Cys His Leu Cys Pro Ser Ser Thr Glu His Ala
    370                 375                 380

Ser Ala Ser Ala Asn Gly His Val Ser Tyr Ser Ala Val Ser Arg Glu
385                 390                 395                 400

Asn Ser Ser Ser Gln Asp Pro Gln Thr Glu Gly Thr Arg
                405                 410

<210> SEQ ID NO 19
<211> LENGTH: 316
<212> TYPE: PRT
<213> ORGANISM: Artificial Sequence
<220> FEATURE:
<223> OTHER INFORMATION: Human CD155

<400> SEQUENCE: 19

Gln Ala Pro Thr Gln Val Pro Gly Phe Leu Gly Asp Ser Val Thr Leu
1               5                   10                  15

Pro Cys Tyr Leu Gln Val Pro Asn Met Glu Val Thr His Val Ser Gln
            20                  25                  30

Leu Thr Trp Ala Arg His Gly Glu Ser Gly Ser Met Ala Val Phe His
        35                  40                  45

Gln Thr Gln Gly Pro Ser Tyr Ser Glu Ser Lys Arg Leu Glu Phe Val
    50                  55                  60

Ala Ala Arg Leu Gly Ala Glu Leu Arg Asn Ala Ser Leu Arg Met Phe
65                  70                  75                  80

Gly Leu Arg Val Glu Asp Glu Gly Asn Tyr Thr Cys Leu Phe Val Thr
                85                  90                  95

Phe Pro Gln Gly Ser Arg Ser Val Asp Ile Trp Leu Arg Val Leu Ala
            100                 105                 110

Lys Pro Gln Asn Thr Ala Glu Val Gln Lys Val Gln Leu Thr Gly Glu
        115                 120                 125

```
Pro Val Pro Met Ala Arg Cys Val Ser Thr Gly Gly Arg Pro Pro Ala
    130                 135                 140

Gln Ile Thr Trp His Ser Asp Leu Gly Gly Met Pro Asn Thr Ser Gln
145                 150                 155                 160

Val Pro Gly Phe Leu Ser Gly Thr Val Thr Val Thr Ser Leu Trp Ile
                165                 170                 175

Leu Val Pro Ser Ser Gln Val Asp Gly Lys Asn Val Thr Cys Lys Val
            180                 185                 190

Glu His Glu Ser Phe Glu Lys Pro Gln Leu Leu Thr Val Asn Leu Thr
        195                 200                 205

Val Tyr Tyr Pro Pro Glu Val Ser Ile Ser Gly Tyr Asp Asn Asn Trp
    210                 215                 220

Tyr Leu Gly Gln Asn Glu Ala Thr Leu Thr Cys Asp Ala Arg Ser Asn
225                 230                 235                 240

Pro Glu Pro Thr Gly Tyr Asn Trp Ser Thr Thr Met Gly Pro Leu Pro
                245                 250                 255

Pro Phe Ala Val Ala Gln Gly Ala Gln Leu Leu Ile Arg Pro Val Asp
            260                 265                 270

Lys Pro Ile Asn Thr Thr Leu Ile Cys Asn Val Thr Asn Ala Leu Gly
        275                 280                 285

Ala Arg Gln Ala Glu Leu Thr Val Gln Val Lys Glu Gly Pro Pro Ser
    290                 295                 300

Glu His Ser Gly Met Ser Arg Asn Ala Ile Ile Phe
305                 310                 315

<210> SEQ ID NO 20
<211> LENGTH: 2838
<212> TYPE: DNA
<213> ORGANISM: Murine
<220> FEATURE:
<221> NAME/KEY: CDS
<222> LOCATION: (62)..(1288)

<400> SEQUENCE: 20
gagataaggc gcttggccgt tactaactgg actacaaaga gctggatcgg accggaacca      60 c atg gct caa ctc gcc cga gcc acc cgc tcc ccg ctg tca tgg ctg ctg     109
  Met Ala Gln Leu Ala Arg Ala Thr Arg Ser Pro Leu Ser Trp Leu Leu
  1               5                  10                  15 ctg ctg ttc tgc tat gca ctc cgg aaa gcg ggt ggg gat ata cgt gtg     157
Leu Leu Phe Cys Tyr Ala Leu Arg Lys Ala Gly Gly Asp Ile Arg Val
            20                  25                  30 ctg gtg ccc tac aat tcg aca ggc gtc ttg gga ggg tcg acc acc ttg     205
Leu Val Pro Tyr Asn Ser Thr Gly Val Leu Gly Gly Ser Thr Thr Leu
        35                  40                  45 cac tgt agt ctg act tct aat gag aat gtg act atc act caa ata acc     253
His Cys Ser Leu Thr Ser Asn Glu Asn Val Thr Ile Thr Gln Ile Thr
    50                  55                  60 tgg atg aag aag gat tca ggt gga tcc cac gct ctt gtg gct gtc ttc     301
Trp Met Lys Lys Asp Ser Gly Gly Ser His Ala Leu Val Ala Val Phe
65                  70                  75                  80 cac ccc aag aag ggg ccc aac atc aaa gag cca gag agg gtg aaa ttc     349
His Pro Lys Lys Gly Pro Asn Ile Lys Glu Pro Glu Arg Val Lys Phe
                85                  90                  95 ttg gct gcc caa cag gat ctg agg aac gca tct ctg gcc atc tcg aac     397
Leu Ala Ala Gln Gln Asp Leu Arg Asn Ala Ser Leu Ala Ile Ser Asn
            100                 105                 110 tta agt gta gaa gac gaa ggc atc tat gaa tgt cag att gcc aca ttc     445
```

```
Leu Ser Val Glu Asp Glu Gly Ile Tyr Glu Cys Gln Ile Ala Thr Phe
        115                 120                 125 ccc aga ggc agt aga agc acc aat gcc tgg ctg aag gtg caa gcc cga      493
Pro Arg Gly Ser Arg Ser Thr Asn Ala Trp Leu Lys Val Gln Ala Arg
130                 135                 140 cct aag aac act gca gag gcc ctg gag ccc tct ccc acc ttg ata ctg      541
Pro Lys Asn Thr Ala Glu Ala Leu Glu Pro Ser Pro Thr Leu Ile Leu
145                 150                 155                 160 cag gat gtg gct aaa tgc atc tct gcc aat ggt cac cct cct gga cga      589
Gln Asp Val Ala Lys Cys Ile Ser Ala Asn Gly His Pro Pro Gly Arg
                165                 170                 175 atc tct tgg ccc tcg aat gtg aat gga agt cac cgt gaa atg aag gaa      637
Ile Ser Trp Pro Ser Asn Val Asn Gly Ser His Arg Glu Met Lys Glu
            180                 185                 190 cca ggg tcc cag ccg ggc acc acc aca gtt acc agc tac ctc tcc atg      685
Pro Gly Ser Gln Pro Gly Thr Thr Thr Val Thr Ser Tyr Leu Ser Met
        195                 200                 205 gta cct tct cgc cag gca gac ggc aag aac atc acc tgc acg gtg gag      733
Val Pro Ser Arg Gln Ala Asp Gly Lys Asn Ile Thr Cys Thr Val Glu
210                 215                 220 cat gaa agc tta cag gag ctg gac cag ctg ctg gtg acc ctt tcc caa      781
His Glu Ser Leu Gln Glu Leu Asp Gln Leu Leu Val Thr Leu Ser Gln
225                 230                 235                 240 ccc tat cca cct gaa aac gtg tcc atc tct ggc tat gac ggc aac tgg      829
Pro Tyr Pro Pro Glu Asn Val Ser Ile Ser Gly Tyr Asp Gly Asn Trp
                245                 250                 255 tat gtt ggc ctc act aac ttg acc ctg acc tgt gaa gct cac agc aaa      877
Tyr Val Gly Leu Thr Asn Leu Thr Leu Thr Cys Glu Ala His Ser Lys
            260                 265                 270 cca gcg cct gac atg gct gga tat aac tgg agc acg aac acg ggt gac      925
Pro Ala Pro Asp Met Ala Gly Tyr Asn Trp Ser Thr Asn Thr Gly Asp
        275                 280                 285 ttt ccc aac tct gtt aag cgc cag ggc aat atg ctt cta atc tcc acc      973
Phe Pro Asn Ser Val Lys Arg Gln Gly Asn Met Leu Leu Ile Ser Thr
290                 295                 300 gta gag gat ggt ctc aat aac acg gtc att gtg tgc gaa gtc acc aat     1021
Val Glu Asp Gly Leu Asn Asn Thr Val Ile Val Cys Glu Val Thr Asn
305                 310                 315                 320 gcc cta ggg tct ggg cag ggc caa gtg cac atc att gtt aaa gag aaa     1069
Ala Leu Gly Ser Gly Gln Gly Gln Val His Ile Ile Val Lys Glu Lys
                325                 330                 335 cct gag aat atg cag caa aat aca aga tta cac cta ggc tac atc ttt     1117
Pro Glu Asn Met Gln Gln Asn Thr Arg Leu His Leu Gly Tyr Ile Phe
            340                 345                 350 ctt atc gtc ttt gtc ctc gct gta gtc atc atc atc gca gca cta tac     1165
Leu Ile Val Phe Val Leu Ala Val Val Ile Ile Ile Ala Ala Leu Tyr
        355                 360                 365 act ata cga aga tgc agg cat ggt cgt gct ctg cag tcc aat ccc tca     1213
Thr Ile Arg Arg Cys Arg His Gly Arg Ala Leu Gln Ser Asn Pro Ser
370                 375                 380 gag agg gag aac gtc cag tat tca tct gtg aac ggc gac tgt aga ctg     1261
Glu Arg Glu Asn Val Gln Tyr Ser Ser Val Asn Gly Asp Cys Arg Leu
385                 390                 395                 400 aac atg gag cca aac agc aca agg tga cggtgctggg tagacagaac            1308
Asn Met Glu Pro Asn Ser Thr Arg
                405 taaggaactt gaaggcatag caactggaac cctactctca taaatgaaga agcctccaga   1368 gagactggct gctcagtgtg atgagcatag caagtttggg gggtctccca ggatgctgcc   1428
```

```
gaattccacg ttgtcaaaag gacccatgga ggccagtgtg ttggctcact cttgacatct    1488
cagcaagctg ggggggggg ggggagcata aagcgaggtt gagtctagct tgggctatag     1548
agcaaagccc tgtccataca caaacaagct aaggggcttt gagacggtca gaaactgaag    1608
tcttgctttg ggtaaggtaa atcctctacc gcatgtatgt gctagacttg aaagacttcc    1668
acacagacct ctttataagt tgactccatt ggggctatcc cctcctctct ggacaaggtc    1728
tctgtatgta gccaaggcta ggctcaaact cacagagata tgtctgcttc tacctcccca    1788
gtgctagagt tgaaagtatt tgtgccactg cacttttcta ggtcttcttt taatgaagta    1848
aagtatatat ttataaaaag ctatttagtt atatatatat atattttga gactatttca     1908
tagagcccaa gctaacctca aacttactat gtagccaaga gtgatggtaa actaatttat    1968
tttaatttat ttgtcttcaa ttttaaccat cacccaaccc ctgctcccctt ccatatcttc   2028
tttcaatcca tttcattgtc tttttcttcc cagacactat tctgacttac gtctccatta    2088
caaacatttt attgaactac ataaaaatgt gtgaaccaca aaaaaaaaat gtatttgtca    2148
aaattgtagt tgtctttctg aggctgacct gagttctctg ataccattct ctccagttgt    2208
atccagtttc ctgtaaacaa tgtgactttg tttttctcag tagctaaaac atcccaatta    2268
tgtgagtgta cactttcttt actcattcct ctgtgggcca ccagctgggt tggttccata    2328
tctgagctat tgtgcatgga attgtctctg tggtgggttt agtaaactcc caggaatgcc    2388
tgtacatgtt tgtagaggcc agaagaaggc acaaaatctt gagccaggct acatgcact    2448
tgtgagtagc cccacatagg tgctaagaac ccagttcagg tcctctgctg tgggatggtg    2508
ggctgtgcac agaaagcctg gtcccggtct agcaaaggtc tggaactccg gagccggtgg    2568
gctgtgattt acaccagcat gggatggaag gagttggacc tcgcctcctg ggcacctggc    2628
tcctgtcaca tagctacagc ctcccacagc ccccctatag ggaggtatgc agcatcaatc    2688
acatagtagc tgcactaagc cctcccacat gcaaataagg tttccccaaa ctctcagtcc    2748
aagccaatga aaagtacctg ctgtcaaacc ctaaatcatc cccaaaactc tgtaagtcct    2808
atcagggaat aaaatgtgtg tgaaaactaa                                     2838
```

<210> SEQ ID NO 21
<211> LENGTH: 408
<212> TYPE: PRT
<213> ORGANISM: Murine

<400> SEQUENCE: 21

```
Met Ala Gln Leu Ala Arg Ala Thr Arg Ser Pro Leu Ser Trp Leu Leu
1               5                   10                  15

Leu Leu Phe Cys Tyr Ala Leu Arg Lys Ala Gly Gly Asp Ile Arg Val
            20                  25                  30

Leu Val Pro Tyr Asn Ser Thr Gly Val Leu Gly Ser Thr Thr Leu
        35                  40                  45

His Cys Ser Leu Thr Ser Asn Glu Asn Val Thr Ile Thr Gln Ile Thr
    50                  55                  60

Trp Met Lys Lys Asp Ser Gly Gly Ser His Ala Leu Val Ala Val Phe
65                  70                  75                  80

His Pro Lys Lys Gly Pro Asn Ile Lys Glu Pro Glu Arg Val Lys Phe
                85                  90                  95

Leu Ala Ala Gln Gln Asp Leu Arg Asn Ala Ser Leu Ala Ile Ser Asn
            100                 105                 110

Leu Ser Val Glu Asp Glu Gly Ile Tyr Glu Cys Gln Ile Ala Thr Phe
        115                 120                 125
```

-continued

Pro Arg Gly Ser Arg Ser Thr Asn Ala Trp Leu Lys Val Gln Ala Arg
    130                 135                 140

Pro Lys Asn Thr Ala Glu Ala Leu Glu Pro Ser Pro Thr Leu Ile Leu
145                 150                 155                 160

Gln Asp Val Ala Lys Cys Ile Ser Ala Asn Gly His Pro Pro Gly Arg
                165                 170                 175

Ile Ser Trp Pro Ser Asn Val Asn Gly Ser His Arg Glu Met Lys Glu
            180                 185                 190

Pro Gly Ser Gln Pro Gly Thr Thr Val Thr Ser Tyr Leu Ser Met
        195                 200                 205

Val Pro Ser Arg Gln Ala Asp Gly Lys Asn Ile Thr Cys Thr Val Glu
    210                 215                 220

His Glu Ser Leu Gln Glu Leu Asp Gln Leu Leu Val Thr Leu Ser Gln
225                 230                 235                 240

Pro Tyr Pro Pro Glu Asn Val Ser Ile Ser Gly Tyr Asp Gly Asn Trp
                245                 250                 255

Tyr Val Gly Leu Thr Asn Leu Thr Leu Thr Cys Glu Ala His Ser Lys
            260                 265                 270

Pro Ala Pro Asp Met Ala Gly Tyr Asn Trp Ser Thr Asn Thr Gly Asp
        275                 280                 285

Phe Pro Asn Ser Val Lys Arg Gln Gly Asn Met Leu Leu Ile Ser Thr
    290                 295                 300

Val Glu Asp Gly Leu Asn Asn Thr Val Ile Val Cys Glu Val Thr Asn
305                 310                 315                 320

Ala Leu Gly Ser Gly Gln Gln Val His Ile Val Lys Glu Lys
                325                 330                 335

Pro Glu Asn Met Gln Gln Asn Thr Arg Leu His Leu Gly Tyr Ile Phe
            340                 345                 350

Leu Ile Val Phe Val Leu Ala Val Ile Ile Ala Ala Leu Tyr
        355                 360                 365

Thr Ile Arg Arg Cys Arg His Gly Arg Ala Leu Gln Ser Asn Pro Ser
    370                 375                 380

Glu Arg Glu Asn Val Gln Tyr Ser Ser Val Asn Gly Asp Cys Arg Leu
385                 390                 395                 400

Asn Met Glu Pro Asn Ser Thr Arg
                405

<210> SEQ ID NO 22
<211> LENGTH: 319
<212> TYPE: PRT
<213> ORGANISM: Murine

<400> SEQUENCE: 22

Asp Ile Arg Val Leu Val Pro Tyr Asn Ser Thr Gly Val Leu Gly Gly
1               5                   10                  15

Ser Thr Thr Leu His Cys Ser Leu Thr Ser Asn Glu Asn Val Thr Ile
            20                  25                  30

Thr Gln Ile Thr Trp Met Lys Lys Asp Ser Gly Gly Ser His Ala Leu
        35                  40                  45

Val Ala Val Phe His Pro Lys Lys Gly Pro Asn Ile Lys Glu Pro Glu
    50                  55                  60

Arg Val Lys Phe Leu Ala Ala Gln Gln Asp Leu Arg Asn Ala Ser Leu
65                  70                  75                  80

Ala Ile Ser Asn Leu Ser Val Glu Asp Glu Gly Ile Tyr Glu Cys Gln

```
                    85                  90                  95
Ile Ala Thr Phe Pro Arg Gly Ser Arg Ser Thr Asn Ala Trp Leu Lys
                100                 105                 110
Val Gln Ala Arg Pro Lys Asn Thr Ala Glu Ala Leu Glu Pro Ser Pro
                115                 120                 125
Thr Leu Ile Leu Gln Asp Val Ala Lys Cys Ile Ser Ala Asn Gly His
    130                 135                 140
Pro Pro Gly Arg Ile Ser Trp Pro Ser Asn Val Asn Gly Ser His Arg
145                 150                 155                 160
Glu Met Lys Glu Pro Gly Ser Gln Pro Gly Thr Thr Val Thr Ser
                165                 170                 175
Tyr Leu Ser Met Val Pro Ser Arg Gln Ala Asp Gly Lys Asn Ile Thr
                180                 185                 190
Cys Thr Val Glu His Glu Ser Leu Gln Glu Leu Asp Gln Leu Leu Val
                195                 200                 205
Thr Leu Ser Gln Pro Tyr Pro Pro Glu Asn Val Ser Ile Ser Gly Tyr
    210                 215                 220
Asp Gly Asn Trp Tyr Val Gly Leu Thr Asn Leu Thr Leu Thr Cys Glu
225                 230                 235                 240
Ala His Ser Lys Pro Ala Pro Asp Met Ala Gly Tyr Asn Trp Ser Thr
                245                 250                 255
Asn Thr Gly Asp Phe Pro Asn Ser Val Lys Arg Gln Gly Asn Met Leu
                260                 265                 270
Leu Ile Ser Thr Val Glu Asp Gly Leu Asn Asn Thr Val Ile Val Cys
                275                 280                 285
Glu Val Thr Asn Ala Leu Gly Ser Gly Gln Gly Gln Val His Ile Ile
                290                 295                 300
Val Lys Glu Lys Pro Glu Asn Met Gln Gln Asn Thr Arg Leu His
305                 310                 315

<210> SEQ ID NO 23
<211> LENGTH: 48
<212> TYPE: PRT
<213> ORGANISM: Artificial Sequence
<220> FEATURE:
<223> OTHER INFORMATION: VASP-His6 Tetramerizing Domain

<400> SEQUENCE: 23

Gly Ser Gly Gly Ser Asp Leu Gln Arg Val Lys Gln Glu Leu Leu Glu
1               5                   10                  15
Glu Val Lys Lys Glu Leu Gln Lys Val Lys Glu Glu Ile Ile Glu Ala
                20                  25                  30
Phe Val Gln Glu Leu Arg Gly Ser Gly Gly His His His His His His
                35                  40                  45

<210> SEQ ID NO 24
<211> LENGTH: 2207
<212> TYPE: DNA
<213> ORGANISM: Homo sapiens

<400> SEQUENCE: 24
cccctccctg tggggttcat tgggcatcc cctttctgct gcaggaacct ctcatcagac    60
cgcctgaggg aagcggcgcc cggagacccg ccccggcccg gtccacattc tccccaggaa   120
gccggactct atgggcggg acctggggg agcctgagcc gagcccggag ccagccccga    180 accccctgaac ctccagccag ggcgcccccg ggagcagcca gcccgtgggc gagccgcccg   240
```

```
cccgccgagc agccatgagc gagacggtca tctgttccag ccgggccact gtgatgcttt    300
atgatgatgg caacaagcga tggctccctg ctggcacggg tccccaggcc ttcagccgcg    360
tccagatcta ccacaacccc acggccaatt cctttcgcgt cgtgggccgg aagatgcagc    420
ccgaccagca ggtggtcatc aactgtgcca tcgtccgggg tgtcaagtat aaccaggcca    480
cccccaactt ccatcagtgg cgcgacgctc gccaggtctg gggcctcaac ttcggcagca    540
aggaggatgc ggcccagttt gccgccggca tggccagtgc cctagaggcg ttggaaggag    600
gtgggccccc tccaccccca gcacttccca cctggtcggt cccgaacggc ccctccccgg    660
aggaggtgga gcagcagaaa aggcagcagc ccggcccgtc ggagcacata gagcgccggg    720
tctccaatgc aggaggccca cctgctcccc ccgctggggg tccaccccca ccaccaggac    780
ctccccctcc tccaggtccc cccccacccc caggtttgcc cccttcgggg gtcccagctg    840
cagcgcacgg agcaggggga ggaccacccc ctgcaccccc tctcccggca gcacagggcc    900
ctggtggtgg gggagctggg gccccaggcc tggccgcagc tattgctgga gccaaactca    960
ggaaagtcag caagcaggag gaggcctcag gggggcccac agcccccaaa gctgagagtg   1020
gtcgaagcgg aggtggggga ctcatggaag agatgaacgc catgctggcc cggagaagga   1080
aagccacgca agttggggag aaaaccccca aggatgaatc tgccaatcag gaggagccag   1140
aggccagagt cccggcccag agtgaatctg tgcggagacc ctgggagaag aacagcacaa   1200
ccttgccaag gatgaagtcg tcttcttcgg tgaccacttc cgagacccaa ccctgcacgc   1260
ccagctccag tgattactcg gacctacaga gggtgaaaca ggagcttctg aagaggtga   1320 agaaggaatt gcagaaagtg aaagaggaaa tcattgaagc cttcgtccag gagctgagga   1380
agcggggttc tccctgacca cagggaccca gaagacccgc ttctcctttc cgcacacccg   1440
gcctgtcacc ctgctttccc tgcctctact tgacttggaa ttggctgaag acacaggaat   1500
gcatcgttcc cactccccat cccacttgga aaactccaag ggggtgtggc ttccctgctc   1560
acacccacac tggctgctga ttggctgggg aggcccccgc cctttctcc ctttggtcct   1620 tcccctctgc catcccttg gggccggtcc ctctgctggg gatgcaccaa tgaaccccac   1680
aggaaggggg aaggaaggag ggaatttcac attcccttgt tctagattca ctttaacgct   1740
taatgccttc aaagttttgg ttttttttaag aaaaaaaaat atatatatat ttgggttttg   1800
ggggaaaagg gaattttttt tttctctttg gttttgataa aatgggatgt gggagttttt   1860
aaatgctata gccctgggct tgccccattt ggggcagcta tttaagggga ggggatgtct   1920
caccgggctg ggggtgagat atccccccac cccagggact cccttccct ctggctcctt   1980 cccctttttct atgaggaaat aagatgctgt aacttttgg aacctcagtt ttttgatttt   2040
ttatttgggt aggttttggg gtccaggcca tttttttttac cccttggagg aaataagatg   2100
agggagaaag gagaagggga ggaaacttct cccctcccac cttcacctttt agcttcttga   2160 aaatgggccc ctgcagaata aatctgccag ttttataaaa aaaaaaa                  2207
```

<210> SEQ ID NO 25
<211> LENGTH: 380
<212> TYPE: PRT
<213> ORGANISM: homo sapiens

<400> SEQUENCE: 25

```
Met Ser Glu Thr Val Ile Cys Ser Ser Arg Ala Thr Val Met Leu Tyr
1               5                   10                  15

Asp Asp Gly Asn Lys Arg Trp Leu Pro Ala Gly Thr Gly Pro Gln Ala
            20                  25                  30
```

```
Phe Ser Arg Val Gln Ile Tyr His Asn Pro Thr Ala Asn Ser Phe Arg
        35                  40                  45

Val Val Gly Arg Lys Met Gln Pro Asp Gln Gln Val Ile Asn Cys
 50                  55                  60

Ala Ile Val Arg Gly Val Lys Tyr Asn Gln Ala Thr Pro Asn Phe His
 65                  70                  75                  80

Gln Trp Arg Asp Ala Arg Gln Val Trp Gly Leu Asn Phe Gly Ser Lys
                 85                  90                  95

Glu Asp Ala Ala Gln Phe Ala Ala Gly Met Ala Ser Ala Leu Glu Ala
            100                 105                 110

Leu Glu Gly Gly Pro Pro Pro Pro Ala Leu Pro Thr Trp Ser
           115                 120                 125

Val Pro Asn Gly Pro Ser Pro Glu Val Glu Gln Gln Lys Arg Gln
 130                 135                 140

Gln Pro Gly Pro Ser Glu His Ile Glu Arg Arg Val Ser Asn Ala Gly
145                 150                 155                 160

Gly Pro Pro Ala Pro Ala Gly Gly Pro Pro Pro Pro Gly Pro
                165                 170                 175

Pro Pro Pro Pro Gly Pro Pro Pro Gly Leu Pro Pro Ser Gly
            180                 185                 190

Val Pro Ala Ala His Gly Ala Gly Gly Pro Pro Ala Pro
            195                 200                 205

Pro Leu Pro Ala Ala Gln Gly Pro Gly Gly Gly Ala Gly Ala Pro
 210                 215                 220

Gly Leu Ala Ala Ala Ile Ala Gly Ala Lys Leu Arg Lys Val Ser Lys
225                 230                 235                 240

Gln Glu Glu Ala Ser Gly Gly Pro Thr Ala Pro Lys Ala Glu Ser Gly
                245                 250                 255

Arg Ser Gly Gly Gly Gly Leu Met Glu Glu Met Asn Ala Met Leu Ala
                260                 265                 270

Arg Arg Arg Lys Ala Thr Gln Val Gly Glu Lys Thr Pro Lys Asp Glu
            275                 280                 285

Ser Ala Asn Gln Glu Glu Pro Glu Ala Arg Val Pro Ala Gln Ser Glu
 290                 295                 300

Ser Val Arg Arg Pro Trp Glu Lys Asn Ser Thr Thr Leu Pro Arg Met
305                 310                 315                 320

Lys Ser Ser Ser Val Thr Thr Ser Glu Thr Gln Pro Cys Thr Pro
                325                 330                 335

Ser Ser Ser Asp Tyr Ser Asp Leu Gln Arg Val Lys Gln Glu Leu Leu
            340                 345                 350

Glu Glu Val Lys Lys Glu Leu Gln Lys Val Lys Glu Glu Ile Ile Glu
            355                 360                 365

Ala Phe Val Gln Glu Leu Arg Lys Arg Gly Ser Pro
 370                 375                 380

<210> SEQ ID NO 26
<211> LENGTH: 4
<212> TYPE: PRT
<213> ORGANISM: Artificial Sequence
<220> FEATURE:
<223> OTHER INFORMATION: Linker

<400> SEQUENCE: 26

Gly Ser Gly Gly
1
```

<210> SEQ ID NO 27
<211> LENGTH: 8
<212> TYPE: PRT
<213> ORGANISM: Artificial Sequence
<220> FEATURE:
<223> OTHER INFORMATION: Tag

<400> SEQUENCE: 27

Asp Tyr Lys Asp Asp Asp Asp Lys
1               5

<210> SEQ ID NO 28
<211> LENGTH: 6
<212> TYPE: PRT
<213> ORGANISM: Artificial Sequence
<220> FEATURE:
<223> OTHER INFORMATION: Tag

<400> SEQUENCE: 28

His His His His His His
1               5

<210> SEQ ID NO 29
<211> LENGTH: 726
<212> TYPE: DNA
<213> ORGANISM: murine

<400> SEQUENCE: 29

| | | | | | |
|---|---|---|---|---|---|
| atgcatggct | ggctgctcct | ggtctgggtc | cagggggctga | tacaggctgc | cttcctcgct | 60 |
| acaggagcca | cagcaggcac | gatagataca | aagaggaaca | tctctgcaga | ggaaggtggc | 120 |
| tctgtcatct | acagtgtca | cttctcctct | gacacagctg | aagtgaccca | agtcgactgg | 180 |
| aagcagcagg | accagcttct | ggccatttat | agtgttgacc | tggggtggca | tgtcgcttca | 240 |
| gtcttcagtg | atcgggtggt | cccaggcccc | agcctaggcc | tcaccttcca | gtctctgaca | 300 |
| atgaatgaca | cggagagta | cttctgtacc | tatcatacgt | atcctggtgg | gatttacaag | 360 |
| gggagaatat | tcctgaaggt | ccaagaaagc | tcagtggctc | agttccagac | tgccccgctt | 420 |
| ggaggaacca | tggctgctgt | gctgggactc | atttgcttaa | tggtcacagg | agtgactgta | 480 |
| ctggctagaa | agaagtctat | tagaatgcat | tctatagaaa | gtggccttgg | gagaacagaa | 540 |
| gcggagccac | aggaatggaa | cctgaggagt | ctctcatccc | ctggaagccc | tgtccagaca | 600 |
| caaactgccc | ctgctggtcc | ctgtggagag | caggcagaag | atgactatgc | tgacccacag | 660 |
| gaatacttta | atgtcctgag | ctacagaagc | ctagagagct | tcattgctgt | atcgaagact | 720 |
| ggctaa | | | | | | 726 |

<210> SEQ ID NO 30
<211> LENGTH: 43
<212> TYPE: DNA
<213> ORGANISM: Artificial Sequence
<220> FEATURE:
<223> OTHER INFORMATION: primer

<400> SEQUENCE: 30
tccacaggtg tccagggaat tcaccatgca tggctggctg ctc          43

<210> SEQ ID NO 31
<211> LENGTH: 36
<212> TYPE: DNA
<213> ORGANISM: Artificial Sequence
<220> FEATURE:

<223> OTHER INFORMATION: primer

<400> SEQUENCE: 31
aggcgcgcct ctagattagc cagtcttcga tacagc                              36

<210> SEQ ID NO 32
<211> LENGTH: 414
<212> TYPE: DNA
<213> ORGANISM: Artificial Sequence
<220> FEATURE:
<223> OTHER INFORMATION: oligonucleotide

<400> SEQUENCE: 32
atgcatggct ggctgctcct ggtctgggtc caggggctga tacaggctgc cttcctcgct    60
acaggagcca cagcaggcac gatagataca aagaggaaca tctctgcaga ggaaggtggc   120
tctgtcatct tacagtgtca cttctcctct gacacagctg aagtgaccca agtcgactgg   180
aagcagcagg accagcttct ggccatttat agtgttgacc tggggtggca tgtcgcttca   240
gtcttcagtg atcgggtggt cccaggcccc agcctaggcc tcaccttcca gtctctgaca   300
atgaatgaca cgggagagta cttctgtacc tatcatacgt atcctggtgg gatttacaag   360
gggagaatat tcctgaaggt ccaagaaagc tcagtggctc agttccagac tgcc         414

<210> SEQ ID NO 33
<211> LENGTH: 43
<212> TYPE: DNA
<213> ORGANISM: Artificial Sequence
<220> FEATURE:
<223> OTHER INFORMATION: Primer

<400> SEQUENCE: 33
tccacaggtg tccagggaat tcaccatgca tggctggctg ctc                     43

<210> SEQ ID NO 34
<211> LENGTH: 46
<212> TYPE: DNA
<213> ORGANISM: Artificial Sequence
<220> FEATURE:
<223> OTHER INFORMATION: Primer

<400> SEQUENCE: 34
agggcttgat tgtgggagat ctgggctcgg cagtctggaa ctgagc                  46

<210> SEQ ID NO 35
<211> LENGTH: 61
<212> TYPE: DNA
<213> ORGANISM: Artificial Sequence
<220> FEATURE:
<223> OTHER INFORMATION: Primer

<400> SEQUENCE: 35
ccactttgcc tttctctcca caggtgtcca gggaattcgc aagatgagga tatttgctgt    60
c                                                                    61

<210> SEQ ID NO 36
<211> LENGTH: 57
<212> TYPE: DNA
<213> ORGANISM: Artificial Sequence
<220> FEATURE:
<223> OTHER INFORMATION: Primer

<400> SEQUENCE: 36
gcatggagga cagggcttga ttgtgggaga tctgggctct tcatttggag gatgtgc      57

<210> SEQ ID NO 37
<211> LENGTH: 33
<212> TYPE: DNA
<213> ORGANISM: Artificial Sequence
<220> FEATURE:
<223> OTHER INFORMATION: Primer

<400> SEQUENCE: 37
gcatgaattc gcaagatgcg ctggtgtctc ctc                         33

<210> SEQ ID NO 38
<211> LENGTH: 34
<212> TYPE: DNA
<213> ORGANISM: Artificial Sequence
<220> FEATURE:
<223> OTHER INFORMATION: Primer

<400> SEQUENCE: 38
atgcagatct gggctcaatc tggaacctgg cacc                        34

<210> SEQ ID NO 39
<211> LENGTH: 414
<212> TYPE: DNA
<213> ORGANISM: Artificial Sequence
<220> FEATURE:
<223> OTHER INFORMATION: Primer

<400> SEQUENCE: 39
atgcatggct ggctgctcct ggtctgggtc caggggctga tacaggctgc cttcctcgct    60
acaggagcca cagcaggcac gatagataca aagaggaaca tctctgcaga ggaaggtggc   120
tctgtcatct acagtgtca cttctcctct gacacagctg aagtgaccca agtcgactgg   180
aagcagcagg accagcttct ggccatttat agtgttgacc tggggtggca tgtcgcttca   240
gtcttcagtg atcgggtggt cccaggcccc agcctaggcc tcaccttcca gtctctgaca   300
atgaatgaca cgggagagta cttctgtacc tatcatacgt atcctggtgg gatttacaag   360
gggagaatat tcctgaaggt ccaagaaagc tcagtggctc agttccagac tgcc          414

<210> SEQ ID NO 40
<211> LENGTH: 44
<212> TYPE: DNA
<213> ORGANISM: Artificial Sequence
<220> FEATURE:
<223> OTHER INFORMATION: Primer

<400> SEQUENCE: 40
ccacaggtgt ccagggaatt cgcaagatgc atggctggct gctc              44

<210> SEQ ID NO 41
<211> LENGTH: 37
<212> TYPE: DNA
<213> ORGANISM: Artificial Sequence
<220> FEATURE:
<223> OTHER INFORMATION: Primer

<400> SEQUENCE: 41
ctccaccaga tcccttgcgg gcagtctgga actgagc                      37

<210> SEQ ID NO 42
<211> LENGTH: 420
<212> TYPE: DNA
<213> ORGANISM: Artificial Sequence
<220> FEATURE:

<223> OTHER INFORMATION: Primer

<400> SEQUENCE: 42

| | | | | | |
|---|---|---|---|---|---|
| atgcgctggt | gtctcctcct | gatctgggcc | caggggctga | ggcaggctcc | cctcgcctca | 60 |
| ggaatgatga | caggcacaat | agaaacaacg | gggaacattt | ctgcagagaa | aggtggctct | 120 |
| atcatcttac | aatgtcacct | ctcctccacc | acggcacaag | tgacccaggt | caactgggag | 180 |
| cagcaggacc | agcttctggc | catttgtaat | gctgacttgg | ggtggcacat | ctccccatcc | 240 |
| ttcaaggatc | gagtggcccc | aggtcccggc | ctgggcctca | ccctccagtc | gctgaccgtg | 300 |
| aacgatacag | gggagtactt | ctgcatctat | cacacctacc | ctgatgggac | gtacactggg | 360 |
| agaatcttcc | tggaggtcct | agaaagctca | gtggctgagc | acggtgccag | gttccagatt | 420 |

<210> SEQ ID NO 43
<211> LENGTH: 45
<212> TYPE: DNA
<213> ORGANISM: Artificial Sequence
<220> FEATURE:
<223> OTHER INFORMATION: Tag

<400> SEQUENCE: 43
ggtctgaacg acatcttcga agctcagaaa atcgaatggc acgaa          45

<210> SEQ ID NO 44
<211> LENGTH: 18
<212> TYPE: DNA
<213> ORGANISM: Artificial Sequence
<220> FEATURE:
<223> OTHER INFORMATION: Tag

<400> SEQUENCE: 44
catcaccatc accatcac          18

<210> SEQ ID NO 45
<211> LENGTH: 43
<212> TYPE: DNA
<213> ORGANISM: Artificial Sequence
<220> FEATURE:
<223> OTHER INFORMATION: Primer

<400> SEQUENCE: 45
cacaggtgtc cagggaattc gcaagatgcg ctggtgtctc ctc          43

<210> SEQ ID NO 46
<211> LENGTH: 123
<212> TYPE: DNA
<213> ORGANISM: Artificial Sequence
<220> FEATURE:
<223> OTHER INFORMATION: Primer

<400> SEQUENCE: 46

| | | | | | |
|---|---|---|---|---|---|
| aggcgcgcct | ctagattagt | gatggtgatg | gtgatgtcca | ccagatcctt | cgtgccattc | 60 |
| gattttctga | gcttcgaaga | tgtcgttcag | acctccacca | gatccaatct | ggaacctggc | 120 |
| acc | | | | | | 123 |

<210> SEQ ID NO 47
<211> LENGTH: 27
<212> TYPE: DNA
<213> ORGANISM: Artificial Sequence
<220> FEATURE:
<223> OTHER INFORMATION: Primer

<400> SEQUENCE: 47

-continued ggagtgactg tactggctag aaagaag                                        27

<210> SEQ ID NO 48
<211> LENGTH: 23
<212> TYPE: DNA
<213> ORGANISM: Artificial Sequence
<220> FEATURE:
<223> OTHER INFORMATION: Primer

<400> SEQUENCE: 48
gagactcctc aggttccatt cct                                            23

<210> SEQ ID NO 49
<211> LENGTH: 23
<212> TYPE: DNA
<213> ORGANISM: Artificial Sequence
<220> FEATURE:
<223> OTHER INFORMATION: Primer

<400> SEQUENCE: 49
agctcagtgg ctgagcacgg tgc                                            23

<210> SEQ ID NO 50
<211> LENGTH: 103
<212> TYPE: DNA
<213> ORGANISM: Artificial Sequence
<220> FEATURE:
<223> OTHER INFORMATION: Primer

<400> SEQUENCE: 50
acgcttccgt agatctggtt ccggaggctc cggtggctcc gacctacaga gggtgaaaca    60
ggagcttctg gaagaggtga agaaggaatt gcagaagtga aag                     103

<210> SEQ ID NO 51
<211> LENGTH: 103
<212> TYPE: DNA
<213> ORGANISM: Artificial Sequence
<220> FEATURE:
<223> OTHER INFORMATION: Primer

<400> SEQUENCE: 51
aaggcgcgcc tctagatcag tgatggtgat ggtgatggcc accggaaccc ctcagctcct    60
ggacgaaggc ttcaatgatt tcctctttca ctttctgcaa ttc                     103

<210> SEQ ID NO 52
<211> LENGTH: 47
<212> TYPE: DNA
<213> ORGANISM: Artificial Sequence
<220> FEATURE:
<223> OTHER INFORMATION: Primer

<400> SEQUENCE: 52
ctcagccagg aaatccatgc cgagttgaga cgcttccgta gatctgg                  47

<210> SEQ ID NO 53
<211> LENGTH: 47
<212> TYPE: DNA
<213> ORGANISM: Artificial Sequence
<220> FEATURE:
<223> OTHER INFORMATION: Primer

<400> SEQUENCE: 53
ggggtggggt acaaccccag agctgtttta aggcgcgcct ctagatc                  47

<210> SEQ ID NO 54
<211> LENGTH: 290
<212> TYPE: PRT
<213> ORGANISM: Artificial Sequence
<220> FEATURE:
<223> OTHER INFORMATION: VASP tetramerization domain

<400> SEQUENCE: 54

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290
```

<210> SEQ ID NO 55
<211> LENGTH: 64
<212> TYPE: DNA
<213> ORGANISM: Artificial Sequence
<220> FEATURE:
<223> OTHER INFORMATION: primer

<400> SEQUENCE: 55
caggtgtcca gggaattcat ataggccggc caccatgcgc tggtgtctcc tcctgatctg    60

-continued

| | |
|---|---|
| ggcc | 64 |

<210> SEQ ID NO 56
<211> LENGTH: 33
<212> TYPE: DNA
<213> ORGANISM: Artificial Sequence
<220> FEATURE:
<223> OTHER INFORMATION: primer

<400> SEQUENCE: 56

| | |
|---|---|
| agtctgatgg tgggggcgaa cctggcaccg tgc | 33 |

<210> SEQ ID NO 57
<211> LENGTH: 33
<212> TYPE: DNA
<213> ORGANISM: Artificial Sequence
<220> FEATURE:
<223> OTHER INFORMATION: primer

<400> SEQUENCE: 57

| | |
|---|---|
| gcacggtgcc aggttcgccc ccaccatcag act | 33 |

<210> SEQ ID NO 58
<211> LENGTH: 63
<212> TYPE: DNA
<213> ORGANISM: Artificial Sequence
<220> FEATURE:
<223> OTHER INFORMATION: primer

<400> SEQUENCE: 58

| | |
|---|---|
| aaccccagag ctgttttaag gcgcgcctct agactagaaa ccccttgtt cttcaactcc | 60 |
| atg | 63 |

<210> SEQ ID NO 59
<211> LENGTH: 64
<212> TYPE: DNA
<213> ORGANISM: Artificial Sequence
<220> FEATURE:
<223> OTHER INFORMATION: primer

<400> SEQUENCE: 59

| | |
|---|---|
| caggtgtcca gggaattcat ataggccggc caccatgcgc tggtgtctcc tcctgatctg | 60 |
| ggcc | 64 |

<210> SEQ ID NO 60
<211> LENGTH: 63
<212> TYPE: DNA
<213> ORGANISM: Artificial Sequence
<220> FEATURE:
<223> OTHER INFORMATION: primer

<400> SEQUENCE: 60

| | |
|---|---|
| aaccccagag ctgttttaag gcgcgcctct agactagaaa ccccttgtt cttcaactcc | 60 |
| atg | 63 |

<210> SEQ ID NO 61
<211> LENGTH: 1133
<212> TYPE: DNA
<213> ORGANISM: Artificial Sequence
<220> FEATURE:
<223> OTHER INFORMATION: human zB7R1mFc2

<400> SEQUENCE: 61

| | |
|---|---|
| gaattcgcaa gatgcgctgg tgtctcctcc tgatctgggc ccaggggctg aggcaggctc | 60 |

```
ccctcgcctc aggaatgatg acaggcacaa tagaaacaac ggggaacatt tctgcagaga      120
aaggtggctc tatcatctta caatgtcacc tctcctccac cacggcacaa gtgacccagg      180
tcaactggga gcagcaggac cagcttctgg ccatttgtaa tgctgacttg gggtggcaca      240
tctccccatc cttcaaggat cgagtggccc caggtcccgg cctgggcctc accctccagt      300
cgctgaccgt gaacgataca ggggagtact tctgcatcta tcacacctac cctgatggga      360
cgtacactgg gagaatcttc ctggaggtcc tagaaagctc agtggctgag cacggtgcca      420
ggttccagat tgagcccaga tctcccacaa tcaagccctg tcctccatgc aaatgcccag      480
cacctaacct cgagggtgga ccatccgtct tcatcttccc tccaaagatc aaggatgtac      540
tcatgatctc cctgagcccc atagtcacat gtgtggtggt ggatgtgagc gaggatgacc      600
cagatgtcca gatcagctgg tttgtgaaca acgtggaagt acacacagct cagacacaaa      660
cccatagaga ggattacaac agtactctcc gggtggtcag tgccctcccc atccagcacc      720
aggactggat gagtggcaaa gctttcgcat gcgcggtcaa caacaaagac ctcccagcgc      780
ccatcgagag aaccatctca aaacccaaag gtcagtaag agctccacag gtatatgtct       840
tgcctccacc agaagaagag atgactaaga acaggtcac tctgacctgc atggtcacag       900
acttcatgcc tgaagacatt tacgtggagt ggaccaacaa cgggaaaaca gagctaaact      960
acaagaacac tgaaccagtc ctggactctg atggttctta cttcatgtac agcaagctga     1020
gagtggaaaa gaagaactgg gtggaaagaa atagctactc ctgttcagtg gtccacgagg     1080
gtctgcacaa tcaccacacg actaagagct ctcccggac tccgggtaaa taa             1133
```

<210> SEQ ID NO 62
<211> LENGTH: 605
<212> TYPE: DNA
<213> ORGANISM: Artificial Sequence
<220> FEATURE:
<223> OTHER INFORMATION: hzB7R1VASPpZMP21

<400> SEQUENCE: 62

```
gaattcgcaa gatgcgctgg tgtctcctcc tgatctgggc ccaggggctg aggcaggctc       60
ccctcgcctc aggaatgatg acaggcacaa tagaaacaac ggggaacatt tctgcagaga      120
aaggtggctc tatcatctta caatgtcacc tctcctccac cacggcacaa gtgacccagg      180
tcaactggga gcagcaggac cagcttctgg ccatttgtaa tgctgacttg gggtggcaca      240
tctccccatc cttcaaggat cgagtggccc caggtcccgg cctgggcctc accctccagt      300
cgctgaccgt gaacgataca ggggagtact tctgcatcta tcacacctac cctgatggga      360
cgtacactgg gagaatcttc ctggaggtcc tagaaagctc agtggctgag cacggtgcca      420
ggttccagat tgagcccaga tctggttccg gaggctccgg tggctccgac ctacagaggg      480
tgaaacagga gcttctggaa gaggtgaaga aggaattgca gaaagtgaaa gaggaaatca      540
ttgaagcctt cgtccaggag ctgaggggtt ccggtggcca tcaccatcac catcactgat      600
ctaga                                                                  605
```

<210> SEQ ID NO 63
<211> LENGTH: 1116
<212> TYPE: DNA
<213> ORGANISM: Artificial Sequence
<220> FEATURE:
<223> OTHER INFORMATION: murine zB7R1mFc2

<400> SEQUENCE: 63

```
atgcatggct ggctgctcct ggtctgggtc caggggctga tacaggctgc cttcctcgct      60
acaggagcca cagcaggcac gatagataca aagaggaaca tctctgcaga ggaaggtggc     120
tctgtcatct tacagtgtca cttctcctct gacacagctg aagtgaccca gtcgactgg     180 aagcagcagg accagcttct ggccatttat agtgttgacc tggggtggca tgtcgcttca     240
gtcttcagtg atcgggtggt cccaggcccc agcctaggcc tcaccttcca gtctctgaca     300
atgaatgaca cggagagta cttctgtacc tatcatacgt atcctggtgg gatttacaag     360
gggagaatat tcctgaaggt ccaagaaagc tcagtggctc agttccagac tgccgagccc     420
agatctccca caatcaagcc ctgtcctcca tgcaaatgcc cagcacctaa cctcgagggt     480
ggaccatccg tcttcatctt ccctccaaag atcaaggatg tactcatgat ctccctgagc     540
cccatagtca catgtgtggt ggtggatgtg agcgaggatg acccagatgt ccagatcagc     600
tggtttgtga caacgtgga agtacacaca gctcagacac aaacccatag agaggattac     660
aacagtactc tccgggtggt cagtgccctc cccatccagc accaggactg gatgagtggc     720
aaagctttcg catgcgcggt caacaacaaa gacctcccag cgcccatcga gagaaccatc     780
tcaaaaccca agggtcagt aagagctcca caggtatatg tcttgcctcc accagaagaa     840
gagatgacta agaaacaggt cactctgacc tgcatggtca cagacttcat gcctgaagac     900
atttacgtgg agtggaccaa cacgggaaa acagagctaa actacaagaa cactgaacca     960
gtcctggact ctgatggttc ttacttcatg tacagcaagc tgagagtgga aaagaagaac    1020
tgggtggaaa gaaatagcta ctcctgttca gtggtccacg agggtctgca caatcaccac    1080
acgactaaga gcttctcccg gactccgggt aaataa                                1116
```

<210> SEQ ID NO 64
<211> LENGTH: 582
<212> TYPE: DNA
<213> ORGANISM: Artificial Sequence
<220> FEATURE:
<223> OTHER INFORMATION: murine zB7R1VASPpZMP21

<400> SEQUENCE: 64

```
atgcatggct ggctgctcct ggtctgggtc caggggctga tacaggctgc cttcctcgct      60
acaggagcca cagcaggcac gatagataca aagaggaaca tctctgcaga ggaaggtggc     120
tctgtcatct tacagtgtca cttctcctct gacacagctg aagtgaccca gtcgactgg     180 aagcagcagg accagcttct ggccatttat agtgttgacc tggggtggca tgtcgcttca     240
gtcttcagtg atcgggtggt cccaggcccc agcctaggcc tcaccttcca gtctctgaca     300
atgaatgaca cggagagta cttctgtacc tatcatacgt atcctggtgg gatttacaag     360
gggagaatat tcctgaaggt ccaagaaagc tcagtggctc agttccagac tgccgagccc     420
agatctggtt ccggaggctc cggtggctcc gacctacaga gggtgaaaca ggagcttctg     480
gaagaggtga agaaggaatt gcagaaagtg aaagaggaaa tcattgaagc cttcgtccag     540
gagctgaggg gttccggtgg ccatcaccat caccatcact ga                         582
```

<210> SEQ ID NO 65
<211> LENGTH: 27
<212> TYPE: DNA
<213> ORGANISM: Artificial Sequence
<220> FEATURE:
<223> OTHER INFORMATION: primer

<400> SEQUENCE: 65

```
ggagtgactg tactggctag aaagaag                                           27
```

-continued

<210> SEQ ID NO 66
<211> LENGTH: 23
<212> TYPE: DNA
<213> ORGANISM: Artificial Sequence
<220> FEATURE:
<223> OTHER INFORMATION: primer

<400> SEQUENCE: 66
gagactcctc aggttccatt cct                                               23

<210> SEQ ID NO 67
<211> LENGTH: 24
<212> TYPE: DNA
<213> ORGANISM: Artificial Sequence
<220> FEATURE:
<223> OTHER INFORMATION: primer

<400> SEQUENCE: 67
ccttgggaga acagaagcgg agcc                                              24

<210> SEQ ID NO 68
<211> LENGTH: 470
<212> TYPE: PRT
<213> ORGANISM: homo sapiens

<400> SEQUENCE: 68

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Glu Pro Arg
225                 230                 235                 240

Ser Pro Thr Ile Lys Pro Cys Pro Pro Cys Lys Cys Pro Ala Pro Asn

```
                     245                 250                 255
Leu Glu Gly Gly Pro Ser Val Phe Ile Phe Pro Pro Lys Ile Lys Asp
            260                 265                 270

Val Leu Met Ile Ser Leu Ser Pro Ile Val Thr Cys Val Val Val Asp
        275                 280                 285

Val Ser Glu Asp Asp Pro Asp Val Gln Ile Ser Trp Phe Val Asn Asn
    290                 295                 300

Val Glu Val His Thr Ala Gln Thr Gln Thr His Arg Glu Asp Tyr Asn
305                 310                 315                 320

Ser Thr Leu Arg Val Val Ser Ala Leu Pro Ile Gln His Gln Asp Trp
                325                 330                 335

Met Ser Gly Lys Ala Phe Ala Cys Ala Val Asn Asn Lys Asp Leu Pro
            340                 345                 350

Ala Pro Ile Glu Arg Thr Ile Ser Lys Pro Lys Gly Ser Val Arg Ala
        355                 360                 365

Pro Gln Val Tyr Val Leu Pro Pro Pro Glu Glu Glu Met Thr Lys Lys
    370                 375                 380

Gln Val Thr Leu Thr Cys Met Val Thr Asp Phe Met Pro Glu Asp Ile
385                 390                 395                 400

Tyr Val Glu Trp Thr Asn Asn Gly Lys Thr Glu Leu Asn Tyr Lys Asn
                405                 410                 415

Thr Glu Pro Val Leu Asp Ser Asp Gly Ser Tyr Phe Met Tyr Ser Lys
            420                 425                 430

Leu Arg Val Glu Lys Lys Asn Trp Val Glu Arg Asn Ser Tyr Ser Cys
        435                 440                 445

Ser Val Val His Glu Gly Leu His Asn His His Thr Thr Lys Ser Phe
    450                 455                 460

Ser Arg Thr Pro Gly Lys
465                 470

<210> SEQ ID NO 69
<211> LENGTH: 371
<212> TYPE: PRT
<213> ORGANISM: murine

<400> SEQUENCE: 69

Met His Gly Trp Leu Leu Leu Val Trp Val Gln Gly Leu Ile Gln Ala
1               5                   10                  15

Ala Phe Leu Ala Thr Gly Ala Thr Ala Gly Thr Ile Asp Thr Lys Arg
            20                  25                  30

Asn Ile Ser Ala Glu Glu Gly Gly Ser Val Ile Leu Gln Cys His Phe
        35                  40                  45

Ser Ser Asp Thr Ala Glu Val Thr Gln Val Asp Trp Lys Gln Gln Asp
    50                  55                  60

Gln Leu Leu Ala Ile Tyr Ser Val Asp Leu Gly Trp His Val Ala Ser
65                  70                  75                  80

Val Phe Ser Asp Arg Val Val Pro Gly Pro Ser Leu Gly Leu Thr Phe
                85                  90                  95

Gln Ser Leu Thr Met Asn Asp Thr Gly Glu Tyr Phe Cys Thr Tyr His
            100                 105                 110

Thr Tyr Pro Gly Gly Ile Tyr Lys Gly Arg Ile Phe Leu Lys Val Gln
        115                 120                 125

Glu Ser Ser Val Ala Gln Phe Gln Thr Ala Glu Pro Arg Ser Pro Thr
    130                 135                 140
```

-continued

```
Ile Lys Pro Cys Pro Pro Cys Lys Cys Pro Ala Pro Asn Leu Glu Gly
145                 150                 155                 160

Gly Pro Ser Val Phe Ile Phe Pro Pro Lys Ile Lys Asp Val Leu Met
            165                 170                 175

Ile Ser Leu Ser Pro Ile Val Thr Cys Val Val Val Asp Val Ser Glu
            180                 185                 190

Asp Asp Pro Asp Val Gln Ile Ser Trp Phe Val Asn Asn Val Glu Val
        195                 200                 205

His Thr Ala Gln Thr Gln Thr His Arg Glu Asp Tyr Asn Ser Thr Leu
    210                 215                 220

Arg Val Val Ser Ala Leu Pro Ile Gln His Gln Asp Trp Met Ser Gly
225                 230                 235                 240

Lys Ala Phe Ala Cys Ala Val Asn Asn Lys Asp Leu Pro Ala Pro Ile
            245                 250                 255

Glu Arg Thr Ile Ser Lys Pro Lys Gly Ser Val Arg Ala Pro Gln Val
            260                 265                 270

Tyr Val Leu Pro Pro Pro Glu Glu Glu Met Thr Lys Lys Gln Val Thr
            275                 280                 285

Leu Thr Cys Met Val Thr Asp Phe Met Pro Glu Asp Ile Tyr Val Glu
    290                 295                 300

Trp Thr Asn Asn Gly Lys Thr Glu Leu Asn Tyr Lys Asn Thr Glu Pro
305                 310                 315                 320

Val Leu Asp Ser Asp Gly Ser Tyr Phe Met Tyr Ser Lys Leu Arg Val
            325                 330                 335

Glu Lys Lys Asn Trp Val Glu Arg Asn Ser Tyr Ser Cys Ser Val Val
            340                 345                 350

His Glu Gly Leu His Asn His His Thr Thr Lys Ser Phe Ser Arg Thr
            355                 360                 365

Pro Gly Lys
        370
```